US012098382B2

(12) United States Patent
Perez et al.

(10) Patent No.: US 12,098,382 B2
(45) Date of Patent: *Sep. 24, 2024

(54) RECOMBINANT INFLUENZA VIRUSES AND CONSTRUCTS AND USES THEREOF

(71) Applicant: University of Maryland, College Park, College Park, MD (US)

(72) Inventors: Daniel R. Perez, Olney, MD (US); Hongjun Chen, Hyattsville, MD (US); Yibin Cai, Hyattsville, MD (US); Lindomar Jose Pena, College Park, MD (US); Matthew Angel, Greenbelt, MD (US)

(73) Assignee: University of Marylnd, College Park, College Park, MD (US)

( * ) Notice: Subject to any disclaimer, the term of this patent is extended or adjusted under 35 U.S.C. 154(b) by 401 days.

This patent is subject to a terminal disclaimer.

(21) Appl. No.: 17/333,904

(22) Filed: May 28, 2021

(65) Prior Publication Data

US 2022/0119839 A1 Apr. 21, 2022

Related U.S. Application Data

(63) Continuation of application No. 13/903,891, filed on May 28, 2013, now Pat. No. 11,028,408.

(51) Int. Cl.
| | | |
|---|---|---|
| *C12N 15/86* | (2006.01) | |
| *A61K 39/12* | (2006.01) | |
| *A61K 39/145* | (2006.01) | |
| *C12N 7/00* | (2006.01) | |
| *A61K 39/00* | (2006.01) | |

(52) U.S. Cl.
CPC .............. *C12N 15/86* (2013.01); *A61K 39/12* (2013.01); *A61K 39/145* (2013.01); *C12N 7/00* (2013.01); *A61K 2039/525* (2013.01); *A61K 2039/543* (2013.01); *A61K 2039/70* (2013.01); *C12N 2760/16122* (2013.01); *C12N 2760/16134* (2013.01); *C12N 2760/16143* (2013.01); *C12N 2760/16151* (2013.01); *C12N 2760/16162* (2013.01)

(58) Field of Classification Search
None
See application file for complete search history.

(56) References Cited

U.S. PATENT DOCUMENTS

| 11,028,408 B2 * | 6/2021 | Perez .................... C12N 15/86 |
| 2012/0020997 A1 | 1/2012 | Hoffman et al. |

FOREIGN PATENT DOCUMENTS

WO  WO-2013/177595 A2  11/2013

OTHER PUBLICATIONS

Hoffman, et al. (2000) "A Dna transfection system for generation of influenza A virus from eight plasmids", Proceedings of the National Academy of Science, USA, 97(11): 6108-13. (Year: 2000).*
Pena, et al. (2013) "Influenza Viruses with Rearranged Genomes as Live-Attenuated Vaccines", Journal of Viriology, 87(9): 5118-5127. (Year: 2013).*
Arias, C.F. et al. 2009. Molecular anatomy of 2009 influenza virus A (H1N1). Archives of medical research 40:643-654.
Banner, D. et al. 2012. The current state of H5N1 vaccines and the use of the ferret model for influenza therapeutic and prophylactic development. J Infect Dev Ctries 6:465-469.
Basler, C. F. et al. 2008. Progress in identifying virulence determinants of the 1918 H1N1 and the Southeast Asian H5N1 influenza A viruses. Antiviral Res 79: 166-178.
Belshe, R. B. et al. 1998. The efficacy of live attenuated, cold-adapted, trivalent, intranasal influenza virus vaccine in children. N Engl J Med 338:1405-1412.
Belshe, R. B. et al. 2007. Live attenuated versus inactivated influenza vaccine in infants and young children. N Engl J Med 356: 685-696.
Cai et al., Glutamic Acid to Valine Substitution at Position 59 in PA Enhances Growth of Live-Attenuated Influenza Vaccines in Eggs and Mammalian Cells. University of Maryland (pp. 1-16).
Chen et al., Partial and full PCR-based reverse genetics strategy for influenza viruses. PLoS One, 2012, vol. 7(9): e-46378, Epub Sep. 28, 2012.
Chen, W. et al. 2001. A novel influenza A virus mitochondrial protein that induces cell death. Nat Med 7:1306-1312.
De Felipe, P. 2004. Skipping the co-expression problem: the new 2A "Chysel" technology. Genet Vaccines Ther 2:13.
Deng, T. et al. 2006. Different de novo initiation strategies are used by influenza virus RNA polymerase on its cRNA and viral RNA promoters during viral RNA replication. Journal of virology 80:2337-2348.
Draper, S. J. et al. 2010. Viruses as vaccine vectors for infectious diseases and cancer. Nature reviews. Microbiology 8:62-73.
El Sahly, H. M. et al. 2008. Pandemic H5N1 influenza vaccine development: an update. Expert Rev Vaccines 7:241-247.
Feng, L. 2009. The mouse Pol I terminator is more efficient than the hepatitis delta virus ribozyme in generating influenza-virus-like RNAs with precise 3' ends in a plasmid-only-based virus rescue system. Archives of Virology 154:1151-1156.
Fodor, E. et al. 1999. Rescue of influenza A virus from recombinant Dna. J. Virol. 73:9679-9682.
Fouchier, R.A. et al. 2005. Characterization of a novel influenza A virus hemagglutinin subtype (H16) obtained from black-headed gulls. J Virol 79:2814-2822.
Fujii, K. et al. 2005. Importance of both the coding and the segment 401 specific noncoding regions of the influenza A virus NS segment for its efficient incorporation into virions. J Virol 79(6):3766-3774.

(Continued)

*Primary Examiner* — Robert M Kelly
(74) *Attorney, Agent, or Firm* — BALLARD SPAHR LLP

(57) ABSTRACT

Disclosed are compositions and methods comprising one or more recombinant influenza viruses. Recombinant influenza viruses with mutated polymerases and/or rearranged genomes are disclosed. Constructs comprising different influenza nucleic acid sequences are also provided. Methods of inducing protecting immunity with the recombinant influenza viruses are disclosed. Also disclosed are methods of plasmid-free production of influenza virus comprising amplicons comprising one or more of influenza genes.

10 Claims, 24 Drawing Sheets

Specification includes a Sequence Listing.

(56) References Cited

OTHER PUBLICATIONS

Gao, Q. et al. 2010. A nine-segment influenza A virus carrying subtype H1 and H3 hemagglutinins. J Virol 84: 8062-8071.

Gao, Q. et al. Rewiring the RNAs of influenza virus to prevent reassortment. Proc Natl Acad Sci USA 106: 15891-15896.

Garulli, B. et al. 2004. Mucosal and systemic immune responses to a human immunodeficiency virus type 1 epitope induced upon vaginal infection with a recombinant influenza A virus. J Virol 78(2): 1020-1025.

Golden, W.T. et al. 2005. A rapid, simple, and humane method for submandibular bleeding of mice using a lancet. Lab Anim (NY) 34:39-43.

Hickman, D. et al. 2008. An avian live attenuated master backbone for potential use in epidemic and pandemic influenza vaccines. J Gen Virol 89: 2682-2690.

Hoffmann et al., Unidirectional RNA polymerase I-polymerase II transcription system for the generation of influenza A virus from eight plasmids. J Gen Virol. 2000, vol. 81 (pp. 2843-2847).

Hoffmann, E. et al. 2000. "Ambisense" approach for the generation of influenza A virus: vRNA and mRNA synthesis from one template. Virology 267:310-317.

Hoffmann, E. et al. 2000. A DNA transfection system for generation of influenza A virus from eight plasmids. Proc Natl Acad Sci USA 97: 6108:6113.

Hoffmann, E. et al. 2001. Universal primer set for the full-length amplification of all influenza A viruses. Arch Virol 146: 2275-2289.

Honda, A. et al. 1997. The molecular anatomy of influenza virus RNA polymerase. Biological chemistry 378: 483-488.

Honda, A. et al. 2002. Minimum molecular architectures for transcription and replication of the influenza virus. Proc Natl Acad Sci USA 99:13166-13171.

Huang, Y.W. et al. 2004. The reverse genetics systems for human and animal RNA viruses. Sheng wu gong cheng xue bao=Chinese journal of biotechnology 20:311-318.

Jin, H. et al. 2003. Multiple amino acid residues confer temperature sensitivity to human influenza virus vaccine strains (FluMist) derived from cold-adapted A/Ann Arbor/6/60. Virology 306:18-24.

Johnson, P.R. et al. 1985. Comparison of long-term systemic and secretory antibody responses in children given live, attenuated, or inactivated influenza A vaccine. J Med Virol 17:325-335.

Kawaguchi, A. et al. 2007. De novo replication of the influenza virus RNA genome is regulated by DNA replicative helicase, MCM. The EMBO journal 26:4566-4575.

Kimble, J.B. et al. 2011. Compatibility of H9N2 avian influenza surface genes and 2009 pandemic H1N1 internal genes for transmission in the ferret model. Proc Natl Acad Sci USA 108: 12084-12088.

Lee et al. Activation of influenza virus RNA polymerase by the 5' and 3' terminal duplex of genomic RNA. Nucleic Acids Res. 2003, vol. 31 (6), (pp. 1624-1632).

Liang, Y. et al. 2005. cis-Acting packaging signals in the influenza virus PB1, PB2, and PA genomic RNA segments. J Virol 79: 10348-10355.

Lopez-Turiso, J.A. et al. 1990. The synthesis of influenza virus negative-strand RNA takes place in insoluble complexes present in the nuclear matrix fraction. Virus research 16:325-337.

Mahmood, K. 2008. H5N1 VLP vaccine induced protection in ferrets against lethal challenge with highly pathogenic H5N1 influenza viruses. Vaccine 26: 5393-5399.

Martinez-Sobrido, L. et al. 2007. Recombinant influenza virus vectors. Future Virology 2:401-416.

Massin, P. et al. 2005. Cloning of the chicken RNA polymerase I promoter and use for reverse genetics of influenza A viruses in avian cells. Journal of virology 79: 13811-13816.

Matsuoka, Y. et al. 2009. The ferret model for influenza. Curr Protoc Microbiol Chapter 15: Unit 15G 12.

Neumann, G. et al. 1999. Generation of influenza A viruses entirely from clone cDNAs. Proceedings of the National Academy of Sciences of the United States of America 96: 9345-9350.

Neumann, G. et al. 2000. Influenza A virus NS2 protein mediates vRNP nuclear export through NES-independent interaction with hCRM1. Embo J 19:6751-6758.

Pena, L. et al. 2011. Modifications in the polymerase genes of a swine-like triple-reassortant influenza virus to generate live attenuated vaccines against 2009 pandemic H1N1 viruses. J Virol 85:456-469.

Perales, B. et al. 1997. The influenza A virus PB2 polymerase subunit is required for the replication of viral RNA. J Virol 71:1381-1385.

Perez, D. R. et al. 1998. The matrix 1 protein of influenza A virus inhibits the transcriptase activity of a model influenza reporter genome in vivo. Virology 249:52-61.

Perez, D. R. et al. 2001. Functional analysis of PA binding by influenza a virus PB1: effects on polymerase activity and viral infectivity. Jounral of virology 75:8127-8136.

Perez, D.R. et al. 2003. Role of quail in the interspecies transmission of H9 influenza A viruses: molecular changes on HA that correspond to adaptation from ducks to chickens. J Virol 77:3148-3156.

Petrovsky, N. 2010. Lessons learned from the 2009 H1N1 pandemic. Human Vaccines 6(10):780-783.

Reed et al. 1938. A simple method for estimating fifty percent endpoints. Am J. Hyg. 27:493-497.

Robb, N.C. et al. 2009. NS2/NEP protein regulates transcription and replication of the influenza virus RNA genome. J Gen Virol 90: 1398-1407.

Robertson, J. S. et al. The development of vaccine viruses against pandemic A (H1N1) influenza. Vaccine 29: 1836-1843.

Shao, H. et al. 2011. A novel monoclonal antibody effective against lethal challenge with swine-lineage and 2009 pandemic H1N1 influenza viruses in mice. Virology.

Solorzano, A. et al. 2010. Alternative live-attenuated influenza vaccines based on modifications in the polymerase genes protect against epidemic and pandemic flu. J Virol 84:4587-4596.

Song, H. et al. 2007. A new generation of modified live attenuated avian influenza viruses using two-strategy combination as potential vaccine candidates. J Virol 81: 9238-9248.

Suguitan, A. L. et al. 2006. Live, attenuated influenza H5N1 candidate vaccines provide broad cross-protection in mice and ferrets. PLoS A Med 3:e360.

Suphaphiphat, P. et al. 2010. Human RNA polymerase I-driven reverse genetics for influenza a virus in canine cells. Journal of virology 84(7):3721-3725.

Treanor, J. J. et al. 2006. Safety and immunogenicity of an inactivated subvirion influenza A (H5N1) vaccine. N Engl J Med 354: 1343-1351.

Vreede, F.T. et al. 2007. Influenza virion-derived viral ribonucleoproteins synthesize both mRNA and cRNA in vitro. Journal of virology 81:2196-2204.

Wan, H. et al. 2008. Replication and transmission of H9N2 influenza viruses in ferrets: evaluation of pandemic potential. PLoS One 3:e2923.

Wang, Z. et al. 2007. Cloning of the canine RNA polymerase I promoter and establishment of reverse genetics for influenza A and B in MDCK cells. Virology Journal 4:102.

Webby, R. J. et al. 2007. Influenza viruses in animal wildlife populations. Current topics in microbiology and immunology 315:67-83.

WHO. 2010, posting date. Antigenic and genetic characteristics of influenza A (H5N1) and influenza A (H9N2) viruses and candidate vaccine viruses developed for potential use in human vaccines. [Online].

WHO. 2011, posting date. Manual for the laboratory diagnosis and virological surveillance of influenza [Online].

Yamanaka, K. et al. 1991. In vivo analysis of the promoter structure of the influenza virus RNA genome using a transfection system with an engineered RNA. Proc Natl Acad Sci USA 88:5369-5373.

Ye, J. et al. 2010. Intranasal delivery of an IgA monoclonal antibody effective against sublethal H5N1 influenza virus infection in mice. Clin Vaccine Immunol 17:1363-1370.

Ye, J. et al. 2010. Variations in the hemagglutinin of the 2009 H1N1 pandemic virus: potential for strains with altered virulence phenotype? PLoS Pathog. 6:e1001145.

(56) References Cited

OTHER PUBLICATIONS

Zell, R. et al. 2006. Influenza A virus PB1-F2 gene. Emerging infectious diseases 12:1607-1608; author reply 1608-1609.
Zhang, J. 2012. Advances and future challenges in recombinant adenoviral vectored H5N1 influenza vaccines. Viruses 4: 2711-2735.
Zheng, D. et al. 2012. Development of live-attenuated influenza vaccines against outbreaks of H5N1 influenza. Viruses 4:3589-3605.
International Search Report and Written Opinion issued Dec. 20, 2013 by the International Searching Authority for PCT Application PCT/US2013/042932 filed May 28, 2013 and published as WO 2013/177595 on Nov. 28, 13 (Inventor—Daniel Perez // Applicant—University of Maryland) (11 pages).
International Preliminary Report on Patentability was issued on Nov. 25, 2014 by the International Searching Authority for PCT Application PCT/US2013/042932 filed May 28, 2013 and published as WO 2013/177595 on Nov. 28, 13 (Inventor—Daniel Perez // Applicant—University of Maryland) (7 pages).

\* cited by examiner

A

HA Titer in Egg Embryos 4 dpi mPA: 2ma-Ca/04 H1N1:mPA:5WF10att
PA:  2ma-Ca/04H1N1:6WF10att

TCID50 (in MDCK) result of viruses from inoculation of egg embryos at 4 dpi

Viral Titer (log10 TCID50/ml)

mPA    PA mPA: 2ma-Ca/04 H1N1:mPA:5WF10att
PA:  2ma-Ca/04H1N1:6WF10att

Viral Titer during infection in MDCK cells

- mPA
- PA

Y-axis: Viral Titer (log10 TCID50/ml)
X-axis: Hours Post-Infection (0, 24, 48, 72, 96, 120)

mPA: 2ma-Ca/04 H1N1:mPA:5WF10att
PA: 2ma-Ca/04H1N1:6WF10att

FIG. 2A

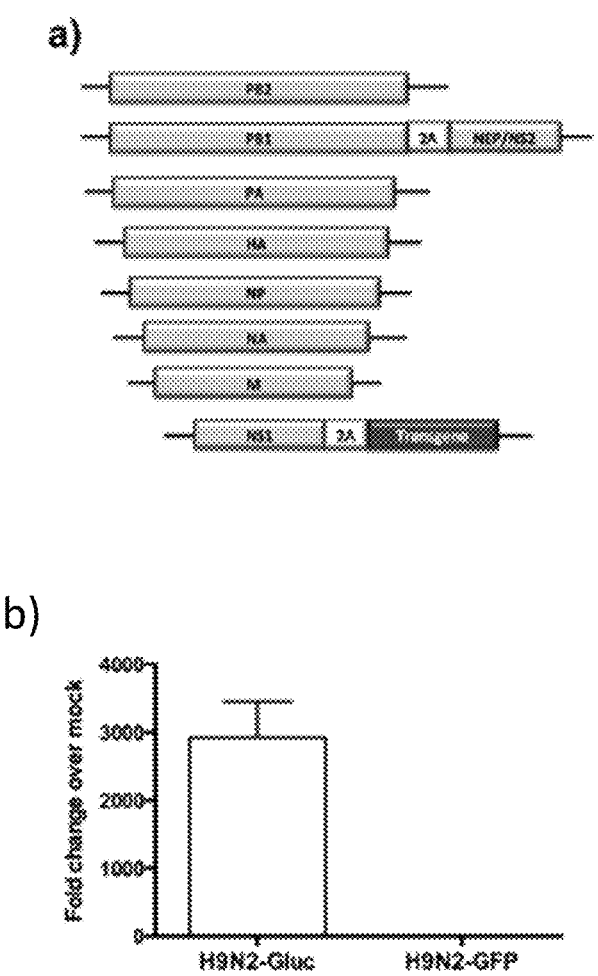
FIG. 5A, FIG. 5B,

SEQUENCE LISTING

```
<160> NUMBER OF SEQ ID NOS: 50

<210> SEQ ID NO 1
<211> LENGTH: 60
<212> TYPE: DNA
<213> ORGANISM: Artificial Sequence
<220> FEATURE:
<223> OTHER INFORMATION: synthetic construct; 5' end of viral RNA
``` segment 8 of H9N2

<400> SEQUENCE: 1
agagataaga actttctcgt ttcagcttat ttaatgataa aaacaccct tgtttctact    60

<210> SEQ ID NO 2
<211> LENGTH: 83
<212> TYPE: DNA
<213> ORGANISM: Artificial Sequence
<220> FEATURE:
<223> OTHER INFORMATION: 5' end of viral RNA segment 2 of H9N2

<400> SEQUENCE: 2
gatctgttcc accattgaag agctcggacg gcaagggaag tgaatttggc ttgtccttca    60
tgaaaaaatg ccttgtttct act    83

<210> SEQ ID NO 3
<211> LENGTH: 57
<212> TYPE: DNA
<213> ORGANISM: Foot-and-mouth disease virus

<400> SEQUENCE: 3
cttctgaact tcgacctcct caagttggcg ggtgacgttg agtccaaccc cgggccc    57

<210> SEQ ID NO 4
<211> LENGTH: 13
<212> TYPE: DNA
<213> ORGANISM: Artificial Sequence
<220> FEATURE:
<223> OTHER INFORMATION: synthetic construct; Uni12 primer

<400> SEQUENCE: 4
agcaaaagca agg    13

<210> SEQ ID NO 5
<211> LENGTH: 25
<212> TYPE: DNA
<213> ORGANISM: Artificial Sequence
<220> FEATURE:
<223> OTHER INFORMATION: synthetic construct; UTR-H1 forward primer

<400> SEQUENCE: 5
agcaaaagca ggggataatt gaatc    25

<210> SEQ ID NO 6
<211> LENGTH: 27
<212> TYPE: DNA
<213> ORGANISM: Artificial Sequence
<220> FEATURE:
<223> OTHER INFORMATION: synthetic construct; UTR-H1 Reverse primer

<400> SEQUENCE: 6
tagtagaaac aagggtgttt tttccgt    27

<210> SEQ ID NO 7
<211> LENGTH: 47
<212> TYPE: DNA
<213> ORGANISM: Artificial Sequence
<220> FEATURE:
<223> OTHER INFORMATION: synthetic construct; hT1Frag forward primer

<400> SEQUENCE: 7
accggagtac tggtcgacct ccgaagttgg gggggagcaa aagcagg    47

```
<210> SEQ ID NO 8
<211> LENGTH: 49
<212> TYPE: DNA
<213> ORGANISM: Artificial Sequence
<220> FEATURE:
<223> OTHER INFORMATION: synthetic construct; pT1HF primer

<400> SEQUENCE: 8
accggagtac tggtcgacct ccgaagttgg gggggagcaa aagcagggg            49

<210> SEQ ID NO 9
<211> LENGTH: 22
<212> TYPE: DNA
<213> ORGANISM: Artificial Sequence
<220> FEATURE:
<223> OTHER INFORMATION: synthetic construct; SwHA-931 reverse primer

<400> SEQUENCE: 9
tctgaaatgg gaggctggtg tt                                         22

<210> SEQ ID NO 10
<211> LENGTH: 24
<212> TYPE: DNA
<213> ORGANISM: Artificial Sequence
<220> FEATURE:
<223> OTHER INFORMATION: synthetic construct; SwHA-752 forward primer

<400> SEQUENCE: 10
tagagccggg agacaaaata acat                                       24

<210> SEQ ID NO 11
<211> LENGTH: 46
<212> TYPE: DNA
<213> ORGANISM: Artificial Sequence
<220> FEATURE:
<223> OTHER INFORMATION: synthetic construct; polHR primer

<400> SEQUENCE: 11
gtcggcattt tgggccgccg ggttattata gaaacaaggg tgtttt               46

<210> SEQ ID NO 12
<211> LENGTH: 40
<212> TYPE: DNA
<213> ORGANISM: Artificial Sequence
<220> FEATURE:
<223> OTHER INFORMATION: synthetic construct; pol1Frag reverse primer

<400> SEQUENCE: 12
gtcggcattt tgggccgccg ggttattagt agaaacaagg                      40

<210> SEQ ID NO 13
<211> LENGTH: 23
<212> TYPE: DNA
<213> ORGANISM: Artificial Sequence
<220> FEATURE:
<223> OTHER INFORMATION: synthetic construct; UTR-N1 forward primer

<400> SEQUENCE: 13
agcaaaagca ggagtttaaa atg                                        23

<210> SEQ ID NO 14
<211> LENGTH: 25
<212> TYPE: DNA
<213> ORGANISM: Artificial Sequence
<220> FEATURE:
<223> OTHER INFORMATION: synthetic construct; UTR-N1 reverse primer
```

```
<400> SEQUENCE: 14
tagtagaaac aaggagtttt tttca                                           25

<210> SEQ ID NO 15
<211> LENGTH: 50
<212> TYPE: DNA
<213> ORGANISM: Artificial Sequence
<220> FEATURE:
<223> OTHER INFORMATION: synthetic construct; hT1N1 forward primer

<400> SEQUENCE: 15
accggagtac tggtcgacct ccgaagttgg gggggagcaa aagcaggagt               50

<210> SEQ ID NO 16
<211> LENGTH: 21
<212> TYPE: DNA
<213> ORGANISM: Artificial Sequence
<220> FEATURE:
<223> OTHER INFORMATION: synthetic construct; N1-562F primer

<400> SEQUENCE: 16
caagtgcttg tcatgatggc a                                               21

<210> SEQ ID NO 17
<211> LENGTH: 24
<212> TYPE: DNA
<213> ORGANISM: Artificial Sequence
<220> FEATURE:
<223> OTHER INFORMATION: synthetic construct; SwNA-763R primer

<400> SEQUENCE: 17
ttacttggtc catcggtcat taca                                            24

<210> SEQ ID NO 18
<211> LENGTH: 51
<212> TYPE: DNA
<213> ORGANISM: Artificial Sequence
<220> FEATURE:
<223> OTHER INFORMATION: synthetic construct; polN1 reverse primer

<400> SEQUENCE: 18
gtcggcattt tgggccgccg ggttattagt agaaacaagg agttttttc a              51

<210> SEQ ID NO 19
<211> LENGTH: 42
<212> TYPE: DNA
<213> ORGANISM: Artificial Sequence
<220> FEATURE:
<223> OTHER INFORMATION: synthetic construct; indoH5-dv forward primer

<400> SEQUENCE: 19
acagccctca aactgaaaact agaggactat ttggagctat ag                      42

<210> SEQ ID NO 20
<211> LENGTH: 32
<212> TYPE: DNA
<213> ORGANISM: Artificial Sequence
<220> FEATURE:
<223> OTHER INFORMATION: synthetic construct; indoH5-dv reverse primer

<400> SEQUENCE: 20
tctagtttca gtttgagggc tgtttctgag cc                                  32

<210> SEQ ID NO 21
<211> LENGTH: 27
```

```
<212> TYPE: DNA
<213> ORGANISM: Artificial Sequence
<220> FEATURE:
<223> OTHER INFORMATION: synthetic construct; polF primer

<400> SEQUENCE: 21 ataacccgg cggcccaaaa tgccgac                                            27

<210> SEQ ID NO 22
<211> LENGTH: 31
<212> TYPE: DNA
<213> ORGANISM: Artificial Sequence
<220> FEATURE:
<223> OTHER INFORMATION: synthetic construct; hPol1 reverse primer

<400> SEQUENCE: 22
atgctgacaa cgtccccggc ccggcgctgc t                                      31

<210> SEQ ID NO 23
<211> LENGTH: 24
<212> TYPE: DNA
<213> ORGANISM: Artificial Sequence
<220> FEATURE:
<223> OTHER INFORMATION: synthetic construct; K9pol1 forward primer

<400> SEQUENCE: 23
acctacctgg caacaaaaaa tgtt                                              24

<210> SEQ ID NO 24
<211> LENGTH: 21
<212> TYPE: DNA
<213> ORGANISM: Artificial Sequence
<220> FEATURE:
<223> OTHER INFORMATION: synthetic construct; K9pol1 reverse primer

<400> SEQUENCE: 24
gcctgcctcc ggagaactttt g                                                21

<210> SEQ ID NO 25
<211> LENGTH: 48
<212> TYPE: DNA
<213> ORGANISM: Artificial Sequence
<220> FEATURE:
<223> OTHER INFORMATION: synthetic construct; kTiUni12 forward primer

<400> SEQUENCE: 25
gcggggacag ctggtcgacc ggatccacca ggagggagca aaagcagg                    48

<210> SEQ ID NO 26
<211> LENGTH: 37
<212> TYPE: DNA
<213> ORGANISM: Artificial Sequence
<220> FEATURE:
<223> OTHER INFORMATION: synthetic construct; kPolUTR reverse primer

<400> SEQUENCE: 26 aacattttttt gttgccaggt aggtagtaga aacaagg                               37

<210> SEQ ID NO 27
<211> LENGTH: 20
<212> TYPE: DNA
<213> ORGANISM: Artificial Sequence
<220> FEATURE:
<223> OTHER INFORMATION: synthetic construct; PB2-1643 forward primer

<400> SEQUENCE: 27
```

```
tcaatgatgt gggagattaa                                          20

<210> SEQ ID NO 28
<211> LENGTH: 26
<212> TYPE: DNA
<213> ORGANISM: Artificial Sequence
<220> FEATURE:
<223> OTHER INFORMATION: synthetic construct; PB2-1811 reverse primer

<400> SEQUENCE: 28
aacccactgt attggcctct aatggc                                   26

<210> SEQ ID NO 29
<211> LENGTH: 20
<212> TYPE: DNA
<213> ORGANISM: Artificial Sequence
<220> FEATURE:
<223> OTHER INFORMATION: synthetic construct; PB1-1240 forward primer

<400> SEQUENCE: 29
ggaatgatga tgggcatgtt                                          20

<210> SEQ ID NO 30
<211> LENGTH: 24
<212> TYPE: DNA
<213> ORGANISM: Artificial Sequence
<220> FEATURE:
<223> OTHER INFORMATION: synthetic construct; PB1-1531 reverse primer

<400> SEQUENCE: 30
ggaagctcca tgctgaaatt ggca                                     24

<210> SEQ ID NO 31
<211> LENGTH: 23
<212> TYPE: DNA
<213> ORGANISM: Artificial Sequence
<220> FEATURE:
<223> OTHER INFORMATION: synthetic construct; PA-892 forward primer

<400> SEQUENCE: 31
ttaagcattg aggacccaag tca                                      23

<210> SEQ ID NO 32
<211> LENGTH: 26
<212> TYPE: DNA
<213> ORGANISM: Artificial Sequence
<220> FEATURE:
<223> OTHER INFORMATION: synthetic construct; PA-1314 reverse primer

<400> SEQUENCE: 32
gggtcagtga gagaaaactc catgct                                   26

<210> SEQ ID NO 33
<211> LENGTH: 21
<212> TYPE: DNA
<213> ORGANISM: Artificial Sequence
<220> FEATURE:
<223> OTHER INFORMATION: synthetic construct; HA-760 forward primer

<400> SEQUENCE: 33
tgaactatta ctggaccttg c                                        21

<210> SEQ ID NO 34
<211> LENGTH: 21
<212> TYPE: DNA
<213> ORGANISM: Artificial Sequence
```

```
<220> FEATURE:
<223> OTHER INFORMATION: synthetic construct; HA-1274 reverse primer

<400> SEQUENCE: 34
gttgaattct tacccacag c                                              21

<210> SEQ ID NO 35
<211> LENGTH: 20
<212> TYPE: DNA
<213> ORGANISM: Artificial Sequence
<220> FEATURE:
<223> OTHER INFORMATION: synthetic construct; NP-1116 forward primer

<400> SEQUENCE: 35
gctttccact agaggagttc                                               20

<210> SEQ ID NO 36
<211> LENGTH: 22
<212> TYPE: DNA
<213> ORGANISM: Artificial Sequence
<220> FEATURE:
<223> OTHER INFORMATION: synthetic construct; NP-1441 reverse primer

<400> SEQUENCE: 36
gctcgaagac tccccgcccc tg                                            22

<210> SEQ ID NO 37
<211> LENGTH: 24
<212> TYPE: DNA
<213> ORGANISM: Artificial Sequence
<220> FEATURE:
<223> OTHER INFORMATION: synthetic construct; NA-743 forward primer

<400> SEQUENCE: 37
caagatcgaa aagggaagg ttac                                           24

<210> SEQ ID NO 38
<211> LENGTH: 22
<212> TYPE: DNA
<213> ORGANISM: Artificial Sequence
<220> FEATURE:
<223> OTHER INFORMATION: synthetic construct; NA-905 reverse primer

<400> SEQUENCE: 38
gaaccatgcc agttgtctct gc                                            22

<210> SEQ ID NO 39
<211> LENGTH: 21
<212> TYPE: DNA
<213> ORGANISM: Artificial Sequence
<220> FEATURE:
<223> OTHER INFORMATION: synthetic construct; M-741 forward primer

<400> SEQUENCE: 39
cctatcagaa acgaatgggg g                                             21

<210> SEQ ID NO 40
<211> LENGTH: 21
<212> TYPE: DNA
<213> ORGANISM: Artificial Sequence
<220> FEATURE:
<223> OTHER INFORMATION: synthetic construct; M-915 reverse primer

<400> SEQUENCE: 40
ctccttccgt agaaggccct c                                             21
```

```
<210> SEQ ID NO 41
<211> LENGTH: 21
<212> TYPE: DNA
<213> ORGANISM: Artificial Sequence
<220> FEATURE:
<223> OTHER INFORMATION: synthetic construct; NS-469 forward primer

<400> SEQUENCE: 41
gggctttcac cgaagaggga g                                              21

<210> SEQ ID NO 42
<211> LENGTH: 20
<212> TYPE: DNA
<213> ORGANISM: Artificial Sequence
<220> FEATURE:
<223> OTHER INFORMATION: synthetic construct; NS-887 reverse primer

<400> SEQUENCE: 42
agaaacaagg gtgtttttta                                                20

<210> SEQ ID NO 43
<211> LENGTH: 22
<212> TYPE: DNA
<213> ORGANISM: Artificial Sequence
<220> FEATURE:
<223> OTHER INFORMATION: synthetic construct; pCMV forward primer

<400> SEQUENCE: 43
agggcgacac ggaaatgttg aa                                             22

<210> SEQ ID NO 44
<211> LENGTH: 24
<212> TYPE: DNA
<213> ORGANISM: Artificial Sequence
<220> FEATURE:
<223> OTHER INFORMATION: synthetic construct; pBGH reverse primer

<400> SEQUENCE: 44
cagacaatgc gatgcaattt cctc                                           24

<210> SEQ ID NO 45
<211> LENGTH: 24
<212> TYPE: DNA
<213> ORGANISM: Artificial Sequence
<220> FEATURE:
<223> OTHER INFORMATION: synthetic construct; pT12 forward primer

<400> SEQUENCE: 45
ctagcagtta accggagtac tggt                                           24

<210> SEQ ID NO 46
<211> LENGTH: 47
<212> TYPE: DNA
<213> ORGANISM: Artificial Sequence
<220> FEATURE:
<223> OTHER INFORMATION: synthetic construct; pT1Frag reverse primer

<400> SEQUENCE: 46
cctgcttttg ctcccccca acttcggagg tcgaccagta ctccggt                   47

<210> SEQ ID NO 47
<211> LENGTH: 25
<212> TYPE: DNA
<213> ORGANISM: Artificial Sequence
<220> FEATURE:
<223> OTHER INFORMATION: synthetic construct; pDP2066 forward primer
```

```
<400> SEQUENCE: 47
ataattctct tactgtcatg ccatc                                          25

<210> SEQ ID NO 48
<211> LENGTH: 25
<212> TYPE: DNA
<213> ORGANISM: Artificial Sequence
<220> FEATURE:
<223> OTHER INFORMATION: synthetic construct; pDP2416 reverse primer

<400> SEQUENCE: 48
aacatttccg tgtcgccctt attcc                                          25

<210> SEQ ID NO 49
<211> LENGTH: 8
<212> TYPE: PRT
<213> ORGANISM: Artificial Sequence
<220> FEATURE:
<223> OTHER INFORMATION: synthetic construct; polybasic amino acid
      signal sequence

<400> SEQUENCE: 49

Arg Glu Arg Arg Lys Arg Arg Arg
1               5

<210> SEQ ID NO 50
<211> LENGTH: 8
<212> TYPE: PRT
<213> ORGANISM: Artificial Sequence
<220> FEATURE:
<223> OTHER INFORMATION: synthetic construct; polybasic cleavage site

<400> SEQUENCE: 50

Arg Glu Arg Arg Arg Lys Lys Arg
1               5
```

RECOMBINANT INFLUENZA VIRUSES AND CONSTRUCTS AND USES THEREOF

CROSS-REFERENCE TO RELATED APPLICATIONS

This application claims priority to U.S. application Ser. No. 13/903,891, filed May 28, 2013, which claims benefit of U.S. Provisional Application No. 61/672,138, filed Jul. 16, 2012; U.S. Provisional Application No. 61/651,960, filed May 25, 2012; and U.S. Provisional Application No. 61/728,074, filed Nov. 19, 2012. All of these applications are hereby incorporated herein by reference in their entirety.

STATEMENT REGARDING FEDERALLY SPONSORED RESEARCH

This invention was made with government support under HHSN266200700010C awarded by the NIH. The government has certain rights in the invention.

REFERENCE TO SEQUENCE LISTING

The Sequence Listing submitted May 28, 2013 as a text file named "36429_0005U1_Sequence_Listing.txt," created on May 27, 2021, and having a size of 11,117 bytes is hereby incorporated by reference pursuant to 37 C.F.R. § 1.52(e)(5).

FIELD OF THE INVENTION

The disclosed invention is generally in the field of molecular biology and specifically in the area of virology.

BACKGROUND

Type A Influenza (Flu) viruses, also known as influenza A viruses (IAVs), belong to the family Orthomyxoviridae and their genome consists of eight segments of single-stranded RNA of negative polarity [Webby R J, et al. (2007) Cur.r Top. Microbiol. Immunol. 315: 67-83; Yamanaka K, et al. (1991) Proc Natl Acad Sci USA 88:5369-5373; Lopez-Turiso J A, et al. (1990) Virus Res 16: 325-337.]. The virus has an envelope with a host-derived lipid bilayer and covered with about 500 projecting glycoprotein spikes with hemagglutinating and neuraminidase activities. These activities correspond to the two major surface viral glycoproteins: the hemagglutinin (HA) and neuraminidase (NA), present as homotrimers and homotetramers, respectively. Within the envelope, a matrix protein (M1) and a nucleocapsid (NP) protein protect the viral RNA (Lamb, 1989). The type designation (A, B, or C) is based upon the antigenic features of the M1 and NP proteins. Approximately half of the total genome encodes for the three viral polymerase proteins (segments 1, 2 and 3; (Palese et al., 1977). Segment 5 encodes the NP protein. The three-polymerase subunits (PB1, PB2, and PA), the NP and the vRNA are associated in virions and infected cells in the form of viral ribonucleoprotein particles (vRNPs). Segments 4 and 6 encode for the HA and NA genes, respectively. The two smallest segments (7 and 8) encode two genes each with overlapping reading frames, which are generated by splicing of the co-linear mRNA molecules (Lamb and Lai, 1980; Lamb and Lai, 1984; Lamb et al., 1981). In addition to M1, segment 7 encodes for the proton pump transmembrane protein (M2), which has ion channel activity and is embedded in the viral envelope. Segment 8 encodes for NS1, a nonstructural protein that blocks the host's antiviral response, and the nuclear export protein (NS2 or NEP) a structural component of the viral particle. NEP/NS2 interacts with the cellular export machinery and participates in the assembly of virus particles. Recently, NEP/NS2 has also been implicated in playing a role in the regulation of influenza virus transcription and replication. Thus, the eight RNA segments encode for 10-12 viral proteins, including two surface glycoproteins, HA and NA, M2, M1, NS2/NEP, NS1 and, in some influenza viruses (from an alternative translation start site in segment 1) the PB1-F2, an apoptosis modulatory protein [Arias C F, et al. (2009) Arch Med Res 40: 643-654; Zell R, (2006) Emerg Infect Dis 12: 1607-1608; author reply 1608-1609; Chen W, et al. (2001) Nat Med 7:1306-1312.]. Additional viral protein products include PB1-N40, derived from an alternative start site within the PB1 ORF, resulting in a protein product that lacks the first 39 aa of PB1, and PA-X, derived from the PA mRNA and consists of the N-terminal 191 aa of PA fused to 61 aa that result from +1 frameshifting [Jagger B W, et al. (2012) Science 337: 199-204; Yewdell J W, Ince W L (2012) Science 337: 164-165.].

The present invention provides compositions and methods for manipulating the influenza virus or parts of the influenza virus to provide better vaccines, increased viral protein expression, an influenza viral vector and a quicker and easier method for producing recombinant influenza.

BRIEF SUMMARY

Disclosed are methods and compositions involving recombinant influenza nucleic acid sequences. Disclosed are recombinant proteins comprising a mutated influenza virus RNA-dependent RNA polymerase. The mutated influenza virus RNA-dependent RNA polymerase can have a mutated PA polymerase subunit. The mutated PA polymerase subunit can be an amino acid mutation at position 59. The amino acid mutation at position 59 can be E→V.

Disclosed are constructs comprising a nucleic acid sequence wherein the nucleic acid sequence comprises a rearranged influenza viral genome segment. A nucleic acid sequence can be DNA or RNA, of either polarity, and may include modified nucleotides.

A rearranged influenza viral genome segment can have an NS1 nucleic acid sequence operably linked to an exogenous sequence. The NS1 nucleic acid sequence can be full length NS1 or a partial NS1 gene sequence. The rearranged influenza viral genome segment can have a PB1 nucleic acid sequence operably linked to a NS2 nucleic acid sequence. The constructs can have a cleavage site between the NS1 and exogenous or between the PB1 and NS2 sequences. The cleavage site can be a 2A-like-cis-acting hydrolase element (CHYSEL) site. The CHYSEL site can be a FMDV 2A cleavage site.

Disclosed are vaccines comprising one or more of the disclosed recombinant viruses. A vaccine of the present invention may comprise a live or killed virus, or may comprise a vaccine composition comprising antigenic or bioactive peptides of one or more recombinant viruses disclosed herein or one or more epitopes antigenic or bioactive peptides of one or more recombinant viruses disclosed herein, or combinations of virus, peptides or epitopes. Vaccine compositions may comprise an adjuvant, such as alum, or immunostimulatory compounds. Disclosed are recombinant influenza viruses, compositions comprising recombinant influenza viruses, and pharmaceutical compositions comprising recombinant influenza viruses, or antigenic or bioactive peptides of one or more recombinant viruses disclosed herein, or vaccine compositions, or combinations thereof.

A recombinant influenza virus of the present invention may comprise a mutated influenza virus RNA-dependent RNA polymerase. A recombinant influenza virus of the present invention may comprise a genome that encodes for any of the mutations found in the disclosed recombinant proteins. Furthermore, a recombinant influenza virus may comprise any of the disclosed recombinant proteins.

A recombinant influenza virus of the present invention may comprise a rearranged genome. A rearranged genome may have at least eight segments, for example, a rearranged genome may comprise a NS2 nucleic acid sequence removed from segment 8 of the genome. A NS2 nucleic acid sequence may be operably linked to the PB1 gene. A rearranged genome may comprise an exogenous nucleic acid sequence operably linked to a NS1 sequence. A NS1 sequence may comprise a truncated NS1 sequence. An exogenous sequence may be downstream of the truncated NS1 gene. An exogenous sequence may be a H5N1 hemagglutinin (HA) gene.

Recombinant influenza viruses comprising both a mutated polymerase and a rearranged genome are disclosed.

A rearranged genome comprising nucleic acid sequences encoding PB1 and NS2 may have a cleavage site between the PB1 and NS2 nucleic acid sequences or between an exogenous sequence and a NS1 nucleic acid sequence. A cleavage site may be a 2A-like-cis-acting hydrolase element (CHYSEL) site. A CHYSEL site may be a foot-and-mouth disease virus 2A autoproteolytic (FMDV 2A) site.

Disclosed are amplicons comprising a termination sequence, a viral nucleic acid sequence, and a promoter sequence. A viral nucleic acid sequence may be an influenza virus nucleic acid sequence. An influenza nucleic acid sequence may be a hemagglutinin nucleic acid sequence or a neuraminidase nucleic acid sequence.

A termination sequence of the disclosed amplicons may be a t1 sequence. A promoter sequence may be a pol1 promoter.

Disclosed are methods of immunizing a subject against infection by, or reducing the response to infection by, an influenza virus comprising administering an effective amount of one or more of the disclosed recombinant influenza viruses, vaccines or compositions of the present invention. Such methods may comprise administering non-recombinant influenza virus, or wild-type influenza virus and administering one or more recombinant influenza viruses of the present invention. Such administration may be made concurrently or sequentially, and may comprise one or more compositions comprising wild-type and recombinant influenza viruses.

Also disclosed are methods of increasing an antibody response to influenza viral proteins or epitopes comprising administering to a subject an effective amount any of the disclosed recombinant influenza viruses, vaccines or compositions of the present invention.

A recombinant virus of the present invention may be administered in a composition or vaccine.

Disclosed are methods of increasing influenza viral protein production comprising administering to a subject an effective amount of a composition comprising any of the disclosed recombinant influenza viruses, vaccines or compositions of the present invention.

Disclosed herein are methods of increasing influenza viral particle production comprising transfecting cells with a construct comprising a gene that encodes any of the disclosed recombinant proteins in combination with influenza gene sequences, for example, hemagglutinin (HA), neuraminidase (NA), matrix (M1), nucleocapsid (NP), NS1 or NS2. In particular, a recombinant protein may be a mutated polymerase.

Disclosed are methods of inducing a protective immune response against influenza virus infection and disease comprising administering an effective amount of a composition comprising one or more of the disclosed recombinant influenza viruses. In some aspects a recombinant influenza virus is a virus with a rearranged genome. A rearranged genome may have an exogenous sequence. An exogenous sequence may be an immune modulator or a H5N1 HA gene.

In some aspects, a protective immune response may protect against H5N1.

Disclosed are methods of modulating influenza polymerase activity. Methods of modulating influenza polymerase activity may involve rearranging the influenza genome. A rearranged genome may have a NS2 nucleic acid sequence operably linked to a PB1 nucleic acid sequence. A reduction of influenza polymerase activity may result in a decrease in viral reproduction and the amount of virus particles synthesized.

Disclosed are methods of producing an amplicon comprising a) amplifying a first fragment, wherein the first fragment comprises a fragment of a viral nucleic acid sequence and a termination sequence; b) amplifying a second fragment, wherein the second fragment comprises a fragment of a viral nucleic acid sequence; c) amplifying a third fragment, wherein the third fragment comprises a promoter sequence; and d) combining the three fragments to form an amplicon comprising a termination sequence, a viral nucleic acid sequence, and a promoter sequence. For example, the viral nucleic acid sequence is an influenza viral sequence or an influenza rearranged genomic sequence as disclosed herein.

Methods of producing an amplicon may have a viral nucleic acid sequence that is an influenza nucleic acid sequence. The influenza nucleic acid sequence may be a hemagglutinin nucleic acid sequence or neuraminidase nucleic acid sequence.

A fragment of an influenza nucleic acid sequence in the first fragment and second fragment may have sequences from the same hemagglutinin gene or neuraminidase nucleic acid sequence. The first fragment may be amplified using a forward primer and reverse primer, wherein the forward primer comprises a termination sequence. A termination sequence may be a t1 signal sequence.

Disclosed herein are methods for plasmid-free influenza replication. Such methods may be used for identifying influenza virus, such in identifying the types of influenza virus found in samples from humans or animals or birds. Plasmid-free methods are faster than methods comprising steps for cloning or plasmid production. Plasmid-free methods may overcome plasmid methods where particular proteins, such as HA or N, may be difficult to clone or the clone reproduces at a low or poor level.

Disclosed are influenza viruses identified or produced by a method comprising transfecting cells with one or more amplicons produced by methods disclosed herein along with the remaining influenza nucleic acid segments required to produce an influenza virus. The remaining influenza nucleic acid segments may be present on plasmids or not. The remaining influenza nucleic acid segments may be from a different strain of influenza or the same influenza strain compared to the influenza gene or genes present on one or more amplicons. In an aspect, at least one other gene required for producing influenza virus may be present on an amplicon. An amplicon may have a hemagglutinin sequence. An amplicon may have a neurominidase sequence. The remaining influenza nucleic acid segments required to produce influenza virus may be chosen from the known influenza proteins, including, but not limited to, hemagglutinin, neuraminidase, matrix, nucleocapsid, PB1, PB2, PA, NS1, or NS2.

Also disclosed are combinations of disclosed recombinant viruses and constructs and methods of the using these combinations. For example, disclosed are recombinant influenza viruses having a rearranged genome and a mutated influenza virus RNA-dependent RNA polymerase. A mutated influenza virus RNA-dependent RNA polymerase may have a mutated PA polymerase subunit. A mutated PA polymerase subunit may have an amino acid mutation at position 59. The amino acid mutation at position 59 may be E→V.

Additional advantages of the disclosed method and compositions will be set forth in part in the description which follows, and in part will be understood from the description, or can be learned by practice of the disclosed method and compositions. The advantages of the disclosed method and compositions will be realized and attained by means of the elements and combinations particularly pointed out in the appended claims. It is to be understood that both the foregoing general description and the following detailed description are exemplary and explanatory only and are not restrictive of the invention as claimed.

BRIEF DESCRIPTION OF THE DRAWINGS

The accompanying drawings, which are incorporated in and constitute a part of this specification, illustrate several embodiments of the disclosed method and compositions and together with the description, serve to explain the principles of the disclosed method and compositions.

FIGS. 1A and 1B show the comparison of (A) HA titers and (B) viral replications of 2 ma-Ca/04 H1N1:mPA (E59V): 5WF10att and 2 ma-Ca/04 H1N1:6WF10att by inoculating 10-day-old embryonated eggs with 100 TCID50 of the viruses.

FIGS. 2A and 2B show the comparison of (A) HA titers and (B) viral replications of 2 ma-Ca/04 H1N1:mPA (E59V): 5WF10att and 2 ma-Ca/04 H1N1:6WF10att by infecting MDCK cell with MOI=0.005.

FIGS. 5A and 5B show rearranged H9N2 influenza A viruses expressing foreign genes. (a) Schematic representation of rearranged influenza viruses. NEP/NS2 protein is expressed from a single ORF (solid box) downstream of the PB1 gene, whereas the foreign gene of interest is expressed downstream of a C-terminal truncated NS1 (expressing only the first 99 amino acids) gene. The packaging signals span both the untranslated region (solid line) and part of the ORF at both ends of each RNA segment. Recombinant H9N2 viruses were made expressing either the enhanced green-fluorescent protein (eGFP), or the secreted Gaussia luciferase (Gluc) (b) or the H5 HA ORF. The viruses were rescued by reverse genetics and used to infect MDCK cells. At 24 hpi, GFP expression was detected by confocal microscopy and Gluc was detected in tissue culture supernatant by a luciferase assay using the Biolux™ Gaussia luciferase Assay Kit (NEB) (b). Expression of the H9 and the H5 HA proteins was confirmed by IFA and TEM using monoclonal antibodies specific for these antigens and compared to wt H5N1 or H9N2 viruses, respectively. TEM, black dots correspond to immunogold reactions for either H5 or H9 HA proteins, please note incorporation of H5 HA into virus particles.

FIGS. 6A-6F show the in vitro characterization and in vivo attenuation of rearranged influenza vectors. (a) Minigenome assay. 293-T cells were grown to 80% confluence in 6 well plates and were transfected with 1 μg each of the influenza driven-luciferase reporter plasmid (GLuc) and PB2, PB1, PA and NP plasmids and incubated at different temperatures as shown. pCMV/SEAP, which encodes secreted alkaline phosphatase was cotransfected into the cells to normalize transfection efficiency. The WT PB1 and an attenuated PB1 gene (PB1 att) were used here as a controls. At 24 hours post-transfection, the supernatant was harvested and assayed for both luciferase and phosphatase activities. Normalized polymerase activities (mean±SE) were determined from three independent experiments. (b) Multicycle step growth curve. MDCK cells were seeded in 6-well plates and infected in triplicate with each of the viruses described in Table 1 at a multiplicity of infection (MOI) of 0.01. Supernatants were harvested at the indicated time points and titrated in MDCK cells by TCID50. Data are shown as the mean±SE. (c) Safety studies in mice. Body weight changes following intranasal inoculation of BALB/c mice (n=10) with 105 EID50/mice of the recombinant viruses. (d) Viral replication in the respiratory tract of mice. BALB/c mice (n=4) were inoculated with 105 EID50 and viral titers in the indicated organs at 3 dpi were determined by TCID50. The lower limit of detection (0.6 TCID50/mL) of the assay is indicated by the dashed horizontal line. (e and f) Attenuation in ferrets. Ferrets (n=3) were intranasally inoculated with 106 EID50/animal with the recombinant viruses and body temperature (e) and body weight (f) were recorded daily. Data are shown as the mean±SE.

FIGS. 9A-9C show the protective efficacy of the H9N2-H5 rearranged influenza vector in ferrets. 3-6 month-old female ferrets (n=3) were vaccinated intranasally with 105 EID50/ferret of the recombinant viruses and boosted 2 weeks later using the same viruses and dose. Two weeks after boost, ferrets were challenged with 106 EID50/ferret (equivalent to 10,000 FLD50) of A/NietNam/1203/2004 (H5N1) and protection was evaluated. Nasal washes were collected daily for nine days following challenge to assess challenge virus shedding (a) Survival upon challenge (b) Virus shedding in nasal secretions (mean±SEM of log 10 TCID50/mL)). The lower limit of detection is 0.6 TCID50/mL. Names on the top of each chart indicate the vaccine treatment group. Numbers on the legend indicate the animal identification number. A) percent body weight; B) percent survival; C) virus titers (mean±SEM of log 10 TCID50/gram) in nasal secretions.

FIG. 13 shows a Table with virus rescue with Flu PCR amplicons in 293T/MDCK co-cultured cells.

FIG. 14 shows a Table with virus rescue with H1N1pdm PCR amplicons in Vero cells.

FIG. 15 shows a Table with Flu PCR amplicons rescued with the VN1203 backbone in MDCK cells.

DETAILED DESCRIPTION

Figure 2B:
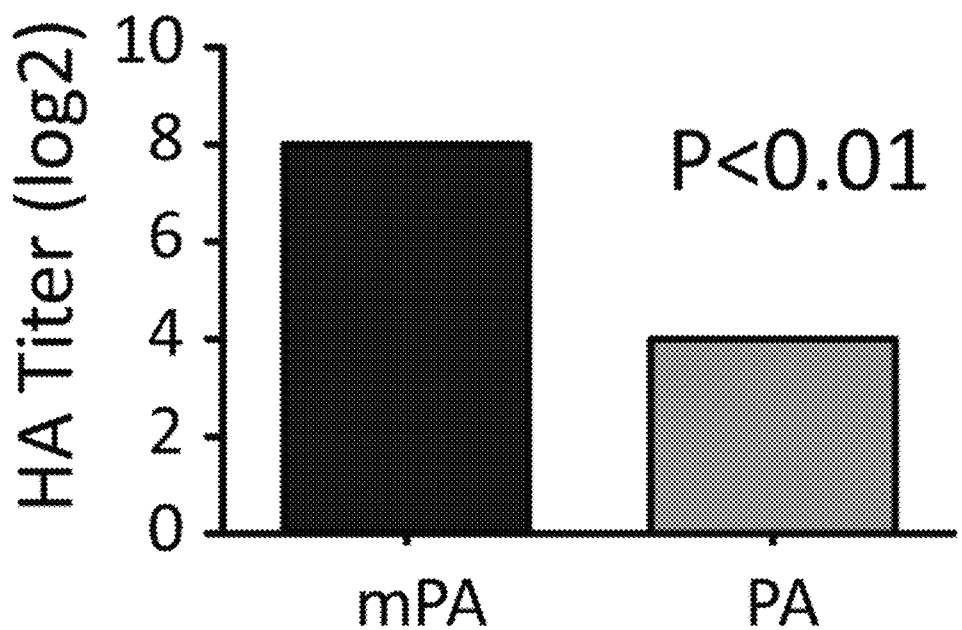

The disclosed method and compositions can be understood more readily by reference to the following detailed description of particular embodiments and the Example included therein and to the Figures and their previous and following description.

A. Influenza Virus

1. Constructs

Disclosed are recombinant influenza viruses having a mutation in the RNA-dependent RNA polymerase, a rearranged genome or a combination thereof.

i. Mutation in Polymerase

The influenza virus RNA-dependent RNA polymerase, composed of PB1, PB2 and PA subunits, is responsible for viral RNA transcription and replication. The synthesized viral mRNA utilizes short capped primers derived from the mRNA of host cells using a 'cap-snatching' mechanism: the PB2 subunit binds to the 5'-cap of the cellular mRNA molecule, the endonuclease activity of PA subunit cleaves and obtains a 10-13 nucleotides long, capped RNA, which is then used as a primer for viral mRNA synthesis by the PB1 subunit (Plotch, 1981; Li, 2001). Recent structure and enzymology studies indicated that N-terminal 209 amino acids of PA are responsible for endonuclease activity (Dias, 2009). Manganese ions play important role in stabilizing the active site. The crystal structure study demonstrated that PA is a type II restriction endonuclease, and the active site binds to two manganese ions similar to other two-metal-dependent endonucleases (Dias, 2009). Based on the crystal structure, E59 is likely to participate or modulate the coordination with maganese (Viadiu, 1998; Horton 2004).

Mutating the PA subunit of the influenza subunit can be advantageous. In particular, the amino acid mutation at position 59 in the PA subunit can be useful in recombinant influenza vaccines. Mutation at position 59 modulates the activity of the influenza polymerase. For example, an E59V substitution may (a) increase the amplification efficiency of influenza virus in mammalian cells and embryonated eggs, for example, for vaccine production, (b) achieve relative high viral protein contents and viral particle amounts without any further adaptation, and (c) improve the antibody response of an immunized host due to a higher dose of antigen delivery.

a. Recombinant Proteins

The present invention comprises recombinant proteins comprising a mutated influenza virus RNA-dependent RNA polymerase. A mutated influenza virus RNA-dependent RNA polymerase may comprise a mutated PA polymerase subunit. The PB1 and PB2 subunits may be wild type or may also contain mutations. If mutations are present in other subunits, the mutations may or may not modulate the effects of a mutated PA polymerase subunit.

In one aspect, a mutated PA polymerase subunit may comprise an amino acid mutation at position 59. For example, the amino acid mutation at position 59 can be E→V. For example, the amino acid mutation at position 59 can be E→A. The glutamic acid at position 59 can be substituted with valine or other known amino acids. One of skill in the art can determine the effect of one or more amino acid substitutions on the functions of a polymerase subunit.

Disclosed recombinant proteins comprising a mutated influenza virus RNA-dependent RNA polymerase may increase viral protein expression. An increase in viral protein expression can lead to an increase in virus production. For example, an E→V mutation at position 59 of the PA polymerase subunit may result in increased viral protein expression and an increase in virus production.

Disclosed recombinant proteins comprising a PA polymerase subunit mutated at position 59 may comprise an amino acid mutation at one or more other positions. When other mutations are present in the PA polymerase subunit or other locations in influenza proteins, these mutations may or may not modulate the effects of the mutation at position 59 in the PA polymerase.

b. Nucleic Acid Sequence of PA Subunit

Disclosed are isolated nucleic acid sequences that encode for a mutated PA polymerase subunit. Isolated nucleic acid sequences may comprise any of the codons that code for Valine at position 59 of the PA polymerase. An isolated nucleic acid sequence can be DNA or RNA, of positive or negative orientation.

Vectors containing the nucleic acid sequences that encode for a PA polymerase mutated at position 59 are disclosed. The vectors can be viral or non-viral.

ii. Rearranged Viral Genome Segments

Disclosed are constructs comprising a nucleic acid sequence wherein the nucleic acid sequence comprises a rearranged influenza viral genome segment. The nucleic acid sequence can be DNA or RNA, of positive or negative polarity. Any of influenza genome segments 1, 2, 3, 4, 5, 6, 7 or 8 can be rearranged. A rearranged genome segment may comprise at least one sequence that is found on that genome segment in a wild type virus. In some instances, the at least one sequence that is found on that segment in a wild type virus is only a partial sequence. For example, a construct containing a rearranged genome segment eight may comprise at least a partial sequence of NS1.

Disclosed constructs may be a linear or circular nucleic acid. In some aspects, the construct is a vector, such as but not limited to a plasmid.

a. Constructs Containing NS1 and Exogenous Nucleic Acid Sequences

The influenza genome can be rearranged so that a foreign gene or an exogenous nucleic acid sequence of interest can be expressed downstream of the NS1 gene under the transcriptional control of the NS1 promoters. Because the NS1 gene is expressed very early during the viral life cycle and at high levels, exogenous nucleic acid sequences or foreign genes expressed co-translationally with the NS1 protein achieve high levels of expression in cells.

Disclosed constructs comprising one or more rearranged influenza viral genome segments may comprise an NS1 nucleic acid sequence operably linked to an exogenous sequence. In one aspect, the NS1 nucleic acid sequence can be full length NS1. In one aspect, the NS1 nucleic acid sequence can be a partial NS1 gene sequence.

An exogenous sequence can be any nucleic acid sequence. In some aspects, an exogenous sequence can be an influenza nucleic acid sequence. An exogenous sequence can be an influenza sequence from a different or the same strain of influenza. For example, an exogenous sequence can be from an H5 strain and the NS1 sequence can be from an H9 strain.

An exogenous sequence may be an immune modulator for immunoprophylactic and therapeutic purposes. An immune modulator may be protective antigens derived from pathogenic organisms (viruses, bacteria, parasites, fungi and helminthes) or cancer cells. An exogenous sequence can be located downstream of an influenza gene, for example, the NS1 gene. Recombinant and wild-type genomic (not rearranged) segments may be used to produce recombinant influenza virus. For example, 6:2 virus reassortants can be made using 6 gene segments (PB2, PA, HA, NP, NA, M) from the strain of interest and 2 rearranged gene segments (PB1-NS2 and NS1-exogenous sequence). In like manner, 7:1 virus reassortants may be used, wherein in one genomic segment is rearranged and 7 genomic segments are wild-type. The present invention contemplates 7:1, 6:2, 5:3, 4:4 reassortants to produce recombinant influenza virus.

In some aspects, the exogenous sequence is a reporter gene. For example, a reporter gene such as enhanced green fluorescent protein (eGFP), turbo red fluorescent protein (TurboRFP), luciferase and others can be located downstream of an influenza gene, for example, the NS1 gene.

The presence of a reporter gene in the construct allows for production of recombinant virus expressing the reporter gene. The constructs or viruses can be used for studying influenza virus pathogenesis in vivo using bioluminescence imaging (BLI) or for studying influenza virus host-pathogen, influenza-bacteria and influenza-virus interaction in vivo.

In some aspects, a rearranged influenza genome comprises inclusion of the last 60 nucleotides (AGAGATAAGAACTTTCTCGTTTCAGCTTATTTAATGATAAAAAACACCCTTGTTTCT A CT; SEQ ID NO:1) corresponding to the 5' end of viral RNA segment 8 of the strain NGuinea fowl/Hong Kong/WF10/99 (H9N2) immediately downstream of stop codon of the foreign gene.

An exogenous sequence can be located downstream of either a full-length or a truncated influenza gene, for example, a NS1 gene, and may be generally under the transcriptional control of the influenza gene promoter or regulatory sequence(s). For example, an exogenous sequence may be located between two AarI cloning sites (or other compatible type I11 restriction endonucleases) so that there is no introduction of exogenous sequences between a 2A CHYSEL and the exogenous sequence.

b. Constructs Containing PB1 and NS2

An influenza genome may be rearranged wherein the NEP/NS2 protein may be expressed from a single open reading frame (ORF) downstream of the PB1 gene. Thus, the rearranged influenza viral genome segment may comprise a PB1 nucleic acid sequence operably linked to a NS2 nucleic acid sequence.

In some aspects, the rearranged genome includes the inclusion of the last 83 nucleotides (GATCTGTTCCACCATTGAAGAGCTCGGACGGCAAGGGAAGTGAATTTGGCTTGTC CTTCATGAAAAAATGCCTTGTTTCTACT; SEQ ID NO:2) corresponding to the 5' end of the viral RNA segment 2 of the strain A/Guinea fowl/Hong Kong/WF10/99 (H9N2) immediately downstream of stop codon of the NEP/NS2 protein.

Thus, a construct having NEP/NS2 expressed from a single long ORF under the control of the segment 2 promoters instead of being produced from a spliced mRNA from segment 8 is disclosed.

c. Cleavage Site in Constructs

Disclosed constructs may comprise a cleavage site between one or more of the nucleic acid sequences. For example, a construct may comprise a cleavage site between the NS1 and exogenous nucleic acid sequences. Disclosed are constructs having a cleavage site between the PB1 and NS2 sequences. Cleavage sites are known to those of skill in the art.

A cleavage site can be a cis-acting hydrolase element (CHYSEL) site. Examples of CHYSEL sites include but are not limited to a foot-and-mouth disease virus 2A autoproteolytic (FMDV 2A) cleavage site. The FMDV 2A sequence is CTTCTGAACTTCGACCTCCT-CAAGTTGGCGGGTGACGTTGAGTC-CAACCCCGGGCCC (SEQ ID NO:3). In some aspects, this sequence can be fused to the carboxyl terminus of the influenza sequence, for example, PB1 sequence. Another sequence, such as NS2, can be inserted after the FMDV 2A sequence resulting in the expression of PB1 with a 2A CHYSEL fused at its carboxyl terminus and NS2 following the cleavage site. Cleavage at the CHYSEL site results in the release of a NS2 protein.

d. Packaging Signals

Disclosed constructs may comprise one or more influenza virus packaging signals. The packaging signals can be present at the 5' and/or 3' ends of the nucleic acid sequence that contains the rearranged viral genome.

A construct of the present invention may comprise one or more genomic segments wherein a genomic segment may comprise one or more of the following elements, including but not limited to, a wild-type influenza gene, a rearranged gene not found on that genomic segment in a wild-type influenza segment, a cleavage site, and one or more packaging signals.

iii. Amplicons

Disclosed are amplicons comprising a termination sequence, an influenza nucleic acid sequence, and a promoter sequence.

a. Termination Sequence

A termination sequence present in a disclosed amplicon may comprise a t1 sequence.

b. Influenza Nucleic Acid Sequence

The influenza nucleic acid sequence of a disclosed amplicon can be any influenza nucleic acid sequence. In some aspects, the influenza nucleic acid sequence encodes one of the two major surface glycoproteins. For example, the influenza nucleic acid sequence can be a hemagglutinin nucleic acid sequence or a neuraminidase nucleic acid sequence.

c. Promoter Sequence

A promoter included in a disclosed amplicon may be any promoter. In some aspects, a promoter sequence can be a polI promoter.

iv. Combination of Mutated Polymerase and Rearranged Viral Genome

Disclosed are constructs comprising a sequence of any of the disclosed mutated polymerases in combination with a rearranged genome segment. A rearranged genome segment can be any of the influenza genome segments. For example, the influenza genome segment can be the segment that contains nucleic acid sequences for the PA polymerase subunit.

2. Recombinant Viruses i. Mutation in Polymerase

Disclosed are recombinant influenza viruses comprising a mutated influenza virus RNA-dependent RNA polymerase. A recombinant influenza virus may comprise a mutated PA polymerase subunit. In some aspects, a mutated PA subunit can have a mutation at position 59. For example, the mutation at position 59 can be an E→V mutation. Any of the mutations described herein can be present in the PA subunit.

Also provided are recombinant influenza viruses comprising a nucleic acid sequence wherein the nucleic acid sequence encodes for a mutation at amino acid 59 of the PA polymerase subunit.

ii. Rearranged Viral Genome Segments

Disclosed are recombinant influenza viruses comprising at least one rearranged influenza genome segment. A rearranged genome segment may comprise rearrangement of any of influenza genome segments 1, 2, 3, 4, 5, 6, 7 or 8. A recombinant influenza virus may comprise one or more of segments 1-8 rearranged.

The recombinant influenza viruses can have a rearranged genome that contains at least eight segments. A rearranged influenza genome may comprise a NS2 nucleic acid sequence, wherein the NS2 nucleic acid sequence is removed from RNA segment 8 of the genome. In some aspects, the NS2 nucleic acid sequence can be operably linked to the PB1 gene found on its normal/wild-type genomic segment. In some aspects, a rearranged genome comprises an exogenous sequence operably linked to an influenza gene sequence, for example, a NS1 sequence. A NS1 sequence can be a truncated sequence. An exogenous sequence can be located downstream of a truncated NS1 sequence.

An exogenous sequence may comprise any nucleic acid sequence. For example, the exogenous sequence can be a nucleic acid sequence from a different influenza strain. In some aspects, the exogenous sequence can be a H5N1 hemagglutinin (HA) sequence or a neuraminidase sequence. In some aspects, the exogenous sequence is a nucleic acid sequence from a virus other than influenza. Recombinant viruses that have a rearranged genome and carry an exogenous sequence can act as a viral vector.

In some aspects, recombinant influenza viruses containing a rearranged genome may comprise both a PB1-NS2 rearrangement and a NS1-exogenous sequence rearrangement.

Disclosed recombinant influenza viruses may comprise a rearranged genome wherein a cleavage site is present within one or more rearranged genome segments. For example, a cleavage site can be present on the rearranged genome segment that contains PB1 and NS2 wherein the cleavage site is located between the PB1 and NS2 nucleic acid sequences. A rearranged genome segment may comprise a cleavage site between the exogenous sequence and the NS1 nucleic acid sequence. In some aspects, the cleavage site can be a CHYSEL site. CHYSEL sites include but are not limited to a foot-and-mouth disease virus 2A autoproteolytic (FMDV 2A) site.

A recombinant influenza virus may comprise a rearranged genome segment having the NS1 sequence operably linked to an exogenous sequence, wherein the exogenous sequence is located between two AarI cloning sites.

Influenza viruses generated having these rearranged genomes can function as improved vaccines against influenza infection and disease and other pathogenic agents as well as facilitate studies regarding influenza pathogenesis in biological systems.

Recombinant influenza viruses with a rearranged genome can be attenuated viruses. Attenuation of the influenza virus may be achieved through fusion of a cleavage site, through introduction of temperature-sensitive (ts) mutations in the PB2 (N265S) and PB1(K391E, E581G, and A661T) genes, through introduction of mutations in PB1 that interferes with PB1-PA interaction (such as T6D), or through truncations in NS1.

iii. Produced with Amplicons

Disclosed are recombinant influenza viruses produced by a method of transfecting cells with one or more of the disclosed amplicons. A recombinant virus can be produced using amplicons comprising one or more of the viral genes. For example, nucleic acid sequences of each of the eight viral genome segments can be provided using amplicons or a combination of amplicons and plasmids.

In some aspects, the recombinant influenza viruses can be produced by using one amplicon comprising the nucleic acid sequence of an influenza viral gene sequence, which is used in combination with the remaining seven genes required to produce influenza virus wherein those remaining seven genes may be present on plasmids used for reverse genetics. The present invention contemplates the use of one or more amplicons comprising the nucleic acid sequence of one or more influenza viral gene sequences to produce influenza virus. A plasmid-free method of producing influenza virus is disclosed herein.

Disclosed recombinant influenza viruses may be produced using one or more amplicons comprising an amplicon having an influenza gene sequence from an influenza strain that is a strain different from one or more source strains of the remaining influenza gene sequences. For example, plasmids containing 7 influenza viral genome segments from an H9 influenza strain can be combined with an amplicon containing an H5 influenza genome sequence from the remaining genome segment. For example, seven different amplicons, each containing one of 7 influenza viral genome segments from an H9 influenza strain can be combined with an amplicon containing an H5 influenza genome sequence from the remaining genome segment. The present invention contemplates combinations of one or more amplicons, each comprising an influenza genome segment sequence, a portion of an influenza genome segment, or a rearranged influenza genome segment comprising influenza genes and/or exogeneous sequences, with one or more amplicons comprising wild-type influenza genomic segment sequences from the same or a different strain of influenza. The present invention contemplates combinations of one or more amplicons, each comprising an influenza genome segment sequence, a portion of an influenza genome segment, or a rearranged influenza genome segment comprising influenza genes and/or exogeneous sequences, with one or more amplicons comp an influenza genome segment sequence, a portion of an influenza genome segment, or a rearranged influenza genome segment comprising influenza genes and/or exogeneous sequences, from the same or a different strain of influenza.

Disclosed recombinant influenza viruses can be produced using one or more amplicons wherein each amplicon has at least one viral genome gene sequence.

Disclosed recombinant influenza viruses can be produced from a method comprising providing to an in vitro system a hemagglutinin nucleic acid sequence present on an amplicon. In some aspects, the remaining seven nucleic acid gene sequences required to produce influenza virus can be neuraminidase, matrix, nucleocapsid, PB1, PB2, PA, NS1, and NS2.

Disclosed recombinant influenza viruses produced by methods comprising using at least one amplicon may comprise an amplicon that contains a rearranged viral genome segment or a mutated polymerase sequence. In some aspects, the methods used to produce virus comprise a plurality of amplicons comprising an amplicon comprising at least one rearranged genome segment and an amplicon comprising a mutated polymerase. In some instances, a rearranged genome segment may comprise a mutated polymerase sequence.

iv. Combination

Disclosed are recombinant influenza viruses comprising a mutated influenza virus RNA-dependent RNA polymerase and a rearranged viral genome. One or more of the genome segments can be rearranged in combination with the presence of a mutated polymerase. The mutated influenza virus RNA-dependent RNA polymerase may comprise a mutated PA polymerase subunit. In some aspects, the mutated PA polymerase subunit includes an amino acid mutation at position 59. For example, the amino acid mutation at position 59 can be E→V.

Disclosed recombinant influenza viruses that contain a mutated influenza virus RNA-dependent RNA polymerase and a rearranged viral genome can increase viral protein expression.

3. Influenza Vaccines

Disclosed are vaccines comprising a recombinant influenza virus having a mutated RNA-dependent RNA polymerase. In some aspects, a vaccine may comprises a recombinant influenza virus having a mutated PA polymerase subunit. Disclosed vaccines may comprise a recombinant influenza virus comprising one or more of the disclosed mutant PA polymerase subunit nucleic acid sequences or mutant PA polymerase subunit proteins. Vaccines of the present invention comprise live or killed virus, pharmaceutical compositions comprising virus, viral peptides, viral epitopes or combinations thereof, and may further comprise immunogenic compounds, stimulants or adjuvants.

The present invention comprises vaccines comprising a recombinant influenza virus having at least one rearranged genome segment as disclosed herein. In some aspects, a vaccine may comprise a recombinant influenza virus having a mutated PA polymerase subunit and at least one rearranged genome segment. Disclosed vaccines may comprise a recombinant influenza virus having at least one rearranged genome segment comprising an exogenous sequence, wherein the exogenous sequence is from a strain of influenza different from the source strain for at least one other genome segment, or the exogenous sequence may be from a source other than influenza.

Vaccines may be provided with an adjuvant. Adjuvants, such as but not limited to alum can be used with vaccines of the present invention.

B. Methods of Immunizing or Inducing Protective Immunity

Disclosed are methods of immunizing or inducing a protective immune response in a subject against influenza virus by administering an effective amount of a recombinant influenza virus. A recombinant virus may comprise a mutated polymerase and/or a rearranged genome.

In some aspects, administering a recombinant influenza virus includes administering a vaccine composition comprising a recombinant influenza virus. The vaccine composition may comprise a recombinant virus as well as other agents such as but not limited to adjuvants or stabilizers. In some aspects, administering a recombinant influenza virus includes administering a composition comprising the recombinant influenza virus.

1. Using a Recombinant Influenza Virus Comprising a Polymerase Mutation

Disclosed are methods of immunizing or inducing a protective immune response in a subject against influenza virus comprising administering an effective amount of a recombinant influenza virus comprising a polymerase mutation.

Also disclosed are methods of increasing an antibody response to influenza viral proteins by administering to a subject an effective amount of a recombinant influenza virus comprising a polymerase mutation. For example, an antibody response may be increased by providing a higher-than-wild-type amount of one or more viral proteins.

Any of the disclosed recombinant influenza viruses comprising a polymerase mutation can be used for these methods. For example, a subject can be immunized with a vaccine that comprises a recombinant influenza virus comprising a mutated PA polymerase subunit. The specific mutation can be at position 59 of the PA subunit. In some aspects, an E→V mutation at position 59 is present. In some aspects, the glutamic acid at position 59 is substituted with any other amino acid that modulates the function and/or activity of the polymerase when compared to wild-type influenza virus polymerase.

2. Using a Recombinant Influenza Virus Having a Rearranged Genome

Disclosed are methods of immunizing or inducing a protective immune response a subject against influenza virus by administering an effective amount of a recombinant influenza virus having a rearranged genome.

Any of the disclosed recombinant influenza viruses having a rearranged genome can be administered in these methods. For example, a recombinant virus having an exogenous sequence operably linked to an influenza gene sequence, such as a NS1 sequence, can be used. An exogenous sequence can be any nucleic acid sequence. In some aspects, the exogenous sequence can be an immune modulator or a nucleic acid sequence from an influenza strain that is the same or different from the strain of the recombinant virus. The exogenous sequence may be a reporter or label sequence, or may be a sequence encoding a peptide or epitope of interest. For example, the nucleic acid sequence can be a H5N1 HA sequence and the strain of the recombinant virus can be H9. Thus, in some aspects, the protective immune response can protect against H5N1.

C. Methods of Increasing Viral Protein/Viral Particle Production

Disclosed are methods of increasing influenza viral protein production by administering to a subject an effective amount of a recombinant influenza virus comprising a mutated polymerase. An effective amount can be an amount of recombinant virus that results in an increase of viral protein production compared to a wild-type virus.

In some aspects, administering a recombinant influenza virus includes administering a composition comprising the recombinant influenza virus. Thus, active agents other than the recombinant influenza virus may be present in the composition. In some aspects, a recombinant influenza virus is the only active agent.

Disclosed are methods of increasing influenza viral particle production by transfecting cells with a construct that comprises a gene that encodes a recombinant protein, wherein the recombinant protein is a mutated polymerase, in combination with the gene sequences for hemagglutinin (HA), neuraminidase (NA), matrix (M1), nucleocapsid (NP), NS1 and NS2. The mutated polymerase can be mutated at the PA subunit. In some aspects, the mutated PA subunit is mutated at position 59. For example, the glutamic acid at position 59 can be valine.

A construct that comprises the gene sequences can be a plasmid or an amplicon. The gene sequences for other influenza gene, including but not limited to, HA, NA, M1, NP, NS1 and NS2, may be provided on plasmids or amplicons.

D. Methods of Modulating Polymerase Activity

Disclosed are methods of modulating influenza polymerase activity. Modulating of polymerase activity may be caused by a mutation of the nucleic acid sequence or the amino acid sequence of one or more influenza genes or regulatory sequences, or may be the result of rearrangement of viral protein sequences or regulatory sequences in the influenza viral genome. Modulating polymerase activity may comprise affecting polymerase activity to any extent or in any function that is different from wild type polymerase activity. For example, modulating can include increasing or decreasing polymerase activity, fidelity, binding and/or substrate utilization.

Disclosed are methods of increasing or decreasing influenza polymerase activity or functions by mutating the sequence of the polymerase. Disclosed polymerase mutations can be used to increase polymerase activity. For example, mutating the PA polymerase subunit can result in increased polymerase activity.

Disclosed are methods of modulating influenza polymerase activity or functions by rearranging the influenza genome. Any of the influenza genome segments 1, 2, 3, 4, 5, 6, 7 or 8 can be rearranged. The rearranged genome segments may comprise at least one sequence that is found on that genome segment in a wild type virus. In some instances, the at least one sequence that is found on that segment in a wild type virus is only a partial sequence. For example, a construct containing a rearranged genome segment eight can contain at least a partial sequence of an influenza sequence such as NS1.

Disclosed recombinant influenza viruses having a rearranged genome can be used to modulate polymerase activity. In some aspects, a recombinant virus having a genome segment comprising NS2 operably linked to PB1 can be used. In some aspects, a recombinant virus having NS1 operably linked to an exogenous sequence can be used.

A modulation of influenza polymerase activity can result in an increase or in a decrease in viral progeny production or other aspects of viral reproduction. Modulated polymerase activity may increase or decrease the amount of viral proteins produced. A change in the amount of viral proteins produced compared to wild-type levels can lead to a change in viral particle production.

E. Methods of Producing Amplicons

Disclosed are methods of producing an amplicon comprising the steps of a) amplifying a first fragment, wherein the first fragment comprises a fragment of a viral nucleic acid sequence and a termination sequence; b) amplifying a second fragment, wherein the second fragment comprises a fragment of a viral nucleic acid sequence; c) amplifying a third fragment, wherein the third fragment comprises a promoter sequence; and d) combining the three fragments to form an amplicon comprising a termination sequence, a viral nucleic acid sequence, and a promoter sequence. A termination sequence may be t1 signal sequence. Disclosed amplicons can be produced using these steps.

The viral nucleic acid sequence can be from any virus such as but not limited to influenza, adenovirus, adeno-associated virus and lentivirus. For example, the viral nucleic acid sequence can be an influenza nucleic acid sequence.

The fragment of a viral nucleic acid sequence in the first fragment and the viral nucleic acid sequence in the second fragment may comprise substantially all or a portion of the same nucleic acid sequence. In other words, the fragment of a viral nucleic acid sequence in the first fragment may comprise the same sequence as part of the nucleic acid sequence in the second fragment. For example, the first fragment and second fragment may comprise a viral nucleic acid sequence from the same viral gene or regulatory sequence.

In some aspects, the influenza nucleic acid sequence may comprise a hemagglutinin or neuraminidase nucleic acid sequence. The fragment of influenza nucleic acid sequence in the first fragment and the influenza nucleic acid sequence in the second fragment may comprise sequences from the same or a different (such as a different strain) hemagglutinin or neuraminidase gene sequence.

Disclosed methods comprise amplification of a first fragment, wherein the first fragment can be amplified using a forward primer and reverse primer, wherein the forward primer includes the termination sequence. The termination sequence in the amplicons may comprise a t1 signal sequence.

Disclosed methods of producing an amplicon may comprise a method of producing an amplicon that contains a rearranged viral genome segment or a mutated polymerase sequence. In some aspects, amplicons produced by methods herein have both a rearranged genome and a mutated polymerase.

F. Methods of Producing a Recombinant Virus Using Amplicons

Disclosed are methods of producing a recombinant virus using amplicons. The amplicons can be produced by the methods disclosed herein. Both RNA and DNA viruses can be produced using methods disclosed herein comprising amplicons. Methods of producing recombinant virus using amplicons can provide a faster and more reliable method of producing virus.

It is known that viruses, such as but not limited to influenza, adenovirus, adeno-associated and lentivirus, can be made using multiple plasmids each containing different viral genes required to make the virus. Thus, for example, when a new strain of influenza evolves, the genes particular for that new strain, for example the HA or NA genes, have to be cloned into appropriate plasmid backbones so that influenza viral vaccines containing the new strain can be produced. The steps of cloning the mutated genes can be time-consuming and in some instances can be very difficult. The use of methods of the present invention comprising amplicons to produce recombinant virus provides an alternate method that can be quicker and easier to perform. Methods of reproducing virus are not limited to the viruses disclosed herein, but may be used for reproduction, in vitro, of any DNA or RNA genome virus.

Methods of producing recombinant virus comprising amplicons comprising providing in an in vitro system for viral reproduction one or more amplicons coding for at least one viral gene. An amplicon for use in such system may comprise an RNA polymerase signal, a termination signal and at least a portion of one viral gene or regulatory sequence. The methods can involve using a combination of amplicons and plasmids coding for the viral genes. The methods may comprise using only amplicons for carrying the viral genes. A method for producing a virus comprises a) providing one or more amplicons, each of which comprises a gene or a portion of a gene of a virus to an in vitro cellular system comprising a polymerase capable of transcribing the amplicon viral genes and b) culturing the cells under circumstances that allow for virus production. The method can further comprise harvesting the virus from the cells or from the cell media. Those methods known in the art for producing viruses using plasmids can be used herein except for replacing the plasmids with the disclosed amplicons. Once the amplicons are in the cells, the remaining steps of producing the virus are the same as those known in the art for producing virus using plasmids.

G. Methods of Using a Recombinant Virus Expressing a Reporter Gene

Disclosed are methods for using one or more disclosed recombinant viruses expressing a reporter gene.

In some aspects, methods comprising recombinant influenza virus expressing a reporter gene may be useful for measuring or detecting influenza-specific neutralizing antibodies or for measuring or detection of replication of such an influenza virus in biological samples. For example, a reporter gene, such as a secreted luciferase gene (Gaussia luciferase-GLuc), can be positioned downstream of an influenza sequence, such as the NS1 gene, and under the regulatory control of the influenza gene or its regulatory sequences, and combinations of reassortants comprising wild-type and rearranged genome segments may be used to produce a recombinant virus or viral proteins. For example, 6:2 virus reassortants can be made comprising 6 wild type gene segments (PB2, PA, HA, NP, NA, M) from the strain of influenza of interest and 2 rearranged gene segments (PB1-NS2 and NS1-GLuc).

Disclosed are methods for studying influenza virus pathogenesis using in vivo bioluminescence imaging (BLI). A reporter gene can be positioned downstream of the NS1 gene and 6:2 virus reassortants are made using 6 wild type gene segments (PB2, PA, HA, NP, NA, M) from the strain of interest and 2 rearranged gene segments (PB1-NS2 and NS1-Luc).

Disclosed are methods for studying influenza virus host-pathogen, influenza-bacteria and influenza-virus interaction in vivo. A reporter gene such as enhanced green fluorescent protein (eGFP), turbo red fluorescent protein (TurboRFP) and other known reporter or label sequences can be positioned downstream of an influenza gene or regulatory sequences, such as the NS1 gene, and reassortants may be used to produce recombinant virus or viral proteins and nucleic acids. For example, 6:2 virus reassortants can be made using 6 wild type gene segments (PB2, PA, HA, NP, NA, M) from the strain of interest and 2 rearranged gene segments (PB1-NS2 and NS1-reporter). Interaction of influenza viruses expressing the reporter with host cells can be detected and quantified using known approaches such as microscopy, fluorescence activated cell sorting (FACS), and immunological techniques. Similarly, interaction of influenza virus expressing a reporter gene with either viral or bacterial pathogens expressing a different reporter gene can be detected and measured in vivo.

Disclosed are methods for high-throughput identification of host factors involved in influenza virus infection, for example, during multiple rounds of replication. A reporter gene, such as secreted luciferase gene (Gaussia luciferase-Gluc), may be positioned downstream of an influenza gene and/or regulatory sequences, for example, the NS1 gene and reassortants may be made. For example, 6:2 virus reassortants can be made using 6 wild type gene segments (PB2, PA, HA, NP, NA, M) from the influenza strain of interest along with 2 rearranged gene segments (PB1-NS2 and NS1-Gluc). Genome-wide RNA interference (RNAi) screens to identify host factors that are involved in or required for influenza virus replication can be easily detected using Gluc as the detected label.

Disclosed are methods for studying influenza virus co-infection and reassortment in in vitro, ex-vivo and in vivo systems. A suitable reporter gene may be positioned downstream of an influenza gene and/or regulatory sequences, for example, the NS1 gene and reassortants may be made. For example, 6:2 virus reassortants are made using 6 wild type gene segments (PB2, PA, HA, NP, NA, M) from the strain of interest and 2 rearranged gene segments (PB1-NS2 and NS1-reporter). Viruses expressing different reporter genes can be produced this way and studied in several biological systems. Alternatively, viruses expressing different domains of GFP can be used in co-infection experiments and intracellular assembly of the two GFP domains creates a molecular switch to detect infection of the same cell by different viruses.

H. Administration

Vaccines, compositions, constructs and viruses of the present invention disclosed herein can be for administration by oral, parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in unit dosage forms appropriate for each route of administration.

Administration to subjects usually involves the construct, virus or vaccine of interest to be formulated into a pharmaceutically acceptable carrier. Pharmaceutically acceptable carriers are well known in the art.

Administration of the disclosed compositions can be accomplished by any acceptable method which allows an effective amount of the recombinant influenza virus to achieve its intended effects. The particular mode selected will depend upon factors such as the particular formulation and the dosage required to induce an effective response.

I. Kits

Vaccines, compositions, constructs and viruses described herein as well as other materials can be packaged together in any suitable combination as a kit useful for performing, or aiding in the performance of, the disclosed method. It is useful if the kit components in a given kit are designed and adapted for use together in the disclosed method. For example disclosed are kits for producing amplicons, the kit comprising amplification primers. The kits also can contain nucleic acid sequences for some or all influenza genes, portions of sequences, and/or regulatory sequences.

J. Definitions

It is understood that the disclosed method and compositions are not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a recombinant influenza virus" includes a plurality of such viruses, reference to "the nucleic acid sequence" is a reference to one or more nucleic acid sequences and equivalents thereof known to those skilled in the art, and so forth.

As used herein the term "effective amount" or means a dosage sufficient to provide the desired pharmacologic and/or physiologic effect. For example, an effective amount of a recombinant influenza virus can increase viral protein production, increase viral particle production, and increase a subject's immune response. The precise dosage will vary according to a variety of factors such as subject-dependent variables (e.g., age, immune system health, etc.).

The term "exogenous sequence" refers to a sequence other than a sequence found in the host. For example, a recombinant influenza virus with a rearranged genome that contains an exogenous sequence means that the exogenous sequence is a sequence other than a sequence found in the host influenza virus. The exogenous sequence can be from a different strain of influenza virus.

The term "operably linked" refers to nucleic acid sequences placed into a functional relationship with another nucleic acid sequence. For example, a promoter is operably linked to a coding sequence if it affects the transcription of the sequence. Generally, "operably linked" means that the nucleic acid sequences being linked are contiguous and in reading frame. With respect to a rearranged viral genome segment having NS1 operably linked to an exogenous sequence means that expression of the NS1 sequence results in expression of the exogenous sequence.

The term "rearranged viral genome" refers to a viral genome that has been altered or rearranged so that at least one nucleic acid sequence is in a different order from that of the wild type sequence. A rearranged viral genome can include one or more rearranged viral genome segments.

The term "subject" refers to a mammal, including, but not limited to, humans, rodents such as mice and rats, other laboratory animals, cells, and cell lines.

"Optional" or "optionally" means that the subsequently described event, circumstance, or material may or may not occur or be present, and that the description includes instances where the event, circumstance, or material occurs or is present and instances where it does not occur or is not present.

Ranges can be expressed herein as from "about" one particular value, and/or to "about" another particular value. When such a range is expressed, also specifically contemplated and considered disclosed is the range from the one particular value and/or to the other particular value unless the context specifically indicates otherwise. Similarly, when values are expressed as approximations, by use of the antecedent "about," it will be understood that the particular value forms another, specifically contemplated embodiment that should be considered disclosed unless the context specifically indicates otherwise. It will be further understood that the endpoints of each of the ranges are significant both in relation to the other endpoint, and independently of the other endpoint unless the context specifically indicates otherwise. Finally, it should be understood that all of the individual values and sub-ranges of values contained within an explicitly disclosed range are also specifically contemplated and should be considered disclosed unless the context specifically indicates otherwise. The foregoing applies regardless of whether in particular cases some or all of these embodiments are explicitly disclosed.

Unless defined otherwise, all technical and scientific terms used herein have the same meanings as commonly understood by one of skill in the art to which the disclosed method and compositions belong. Although any methods and materials similar or equivalent to those described herein can be used in the practice or testing of the present method and compositions, the particularly useful methods, devices, and materials are as described. Publications cited herein and the material for which they are cited are hereby specifically incorporated by reference. Nothing herein is to be construed as an admission that the present invention is not entitled to antedate such disclosure by virtue of prior invention. No admission is made that any reference constitutes prior art. The discussion of references states what their authors assert, and applicants reserve the right to challenge the accuracy and pertinency of the cited documents. It will be clearly understood that, although a number of publications are referred to herein, such reference does not constitute an admission that any of these documents forms part of the common general knowledge in the art.

Throughout the description and claims of this specification, the word "comprise" and variations of the word, such as "comprising" and "comprises," means "including but not limited to," and is not intended to exclude, for example, other additives, components, integers or steps. In particular, in methods stated as comprising one or more steps or operations it is specifically contemplated that each step comprises what is listed (unless that step includes a limiting term such as "consisting of"), meaning that each step is not intended to exclude, for example, other additives, components, integers or steps that are not listed in the step.

Those skilled in the art will recognize, or be able to ascertain using no more than routine experimentation, many equivalents to the specific embodiments of the method and compositions described herein. Such equivalents are intended to be encompassed by the following claims.

It is to be understood that the disclosed method and compositions are not limited to specific synthetic methods, specific analytical techniques, or to particular reagents unless otherwise specified, and, as such, may vary. It is also to be understood that the terminology used herein is for the purpose of describing particular embodiments only and is not intended to be limiting.

Disclosed are materials, compositions, and components that can be used for, can be used in conjunction with, can be used in preparation for, or are products of the disclosed method and compositions. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited, each is individually and collectively contemplated. Thus, is this example, each of the combinations A-E, A-F, B-D, B-E, B-F, C-D, C-E, and C-F are specifically contemplated and should be considered disclosed from disclosure of A, B, and C; D, E, and F; and the example combination A-D. Likewise, any subset or combination of these is also specifically contemplated and disclosed. Thus, for example, the sub-group of A-E, B-F, and C-E are specifically contemplated and should be considered disclosed from disclosure of A, B, and C; D, E, and F; and the example combination A-D. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods, and that each such combination is specifically contemplated and should be considered disclosed.

EXAMPLES

A. Example 1: An Amino Acid Mutation in the PA Polymerase Subunit of Influenza Leads to Increased Viral Protein Expression: Implications for Vaccine Preparations An amino acid mutation in the PA polymerase of influenza virus can improve viral protein expression in infected cells and embryonated eggs. The mutation can occur at amino acid position 59 in which the highly conserved amino acid glutamic acid (E) is replaced by valine (V) or any other amino acid resulting in high levels of expression of viral proteins during infection. This phenotype can be used for improving antibody responses and/or improving antigenic protein content of influenza vaccines.

In particular, a mutation at position 59 of PA can render influenza viruses to produce higher content of viral proteins. Applying this mutation into recombinant influenza vaccines can largely increase the amount of antigenic protein; and in turn, improve the antibody response in the immunized host.

The PA E59V mutation improves the viral protein levels about 16-20 fold; and increases production of infectious viral particles by about 3-5 fold.

TABLE 1

Enhanced HA titers after serially propagated recombinant influenza virus ma-CA/04 H1N1:6WF10att in 10-day-old embryonated eggs 7 times.

| Passage | HA Titer (log2) |
|---|---|
| 1 | 5, 4, 3, 5, 5 |
| 2 | 5, 5, 5, 5, 6 |
| 3 | 6, 3, 7, 8, 7, 7 |
| 4 | 9, 6, 7, 7, 6 |
| 5 | 8, 9, 9, 9, 8 |
| 6 | 9, 9, 8, 11, 9, 6, 8 |
| 7 | 11, 9, 11, 9 |
| 8 | 10, 11, 8, 11, 10, 10, 10 |

With the purpose of evaluating a live attenuated influenza virus as a candidate vaccine against the pandemic swine-origin H1N1 virus, a 6+2 recombinant virus was designed and produced that carries the surface genes of A/California/04/09 (H1N1) and 6 internal genes from A/guinea fowl/Hong Kong/WF10/99 (H9N2) att strain. The new virus, labeled ma-Ca/04 H1N1:6WF10att, grew to low HA titers in 10-day-old embryonated chicken eggs (P1). After 7 additional passages (P8) in eggs, the HA titer of the virus was 30-fold higher than of P1. Sequencing results revealed there is only one single amino acid substitution, on PA: residue 59 changed from Glutamic acid to Valine.

10-day-old egg embryonated eggs were inoculated with 100 TCID50 of 2 ma-Ca/04 H1N1:mPA (E59V):5WF10att or 2 ma-Ca/04 H1N1:6WF10att, respectively; and 3 eggs for each group. The HA titers of the viruses in eggs were detected at 4-day post infection; and the viral titer were detected using TCID50 method in MDCK cells. The results showed HA titer and viral titer (at HA peak) of 2ma H1N1 (Ca/04):mPA (E59V):5WF10att were 20- and 4.6-fold higher than those of 2 ma H1N1 (Ca/04):6WF10att, respectively (FIG. 1).

MDCK cells in 6-well plates were inoculated in duplicates with 2 ma-Ca/04 H1N1:mPA (E59V):5WF10att or 2 ma-Ca/04 H1N1:6WF10att, respectively (MOI=0.005). Viral titers in supernatants were detected at 24, 48, 72, 96 and 120 h post infection (hpi) by TCID50 in MDCK cells (FIG. 2A). HA titers at the viral peak (96 hpi) were detected (FIG. 2B). The result shows that HA titer and viral titer at HA peak (4 day post-inoculation, MOI=0.005) of 2 ma H1N1 (Ca/04):mPA:5WF10att were 16- and 3.9-fold higher than those of 2 ma H1N1 (Ca/04):6WF10att, respectively.

Figure 3:
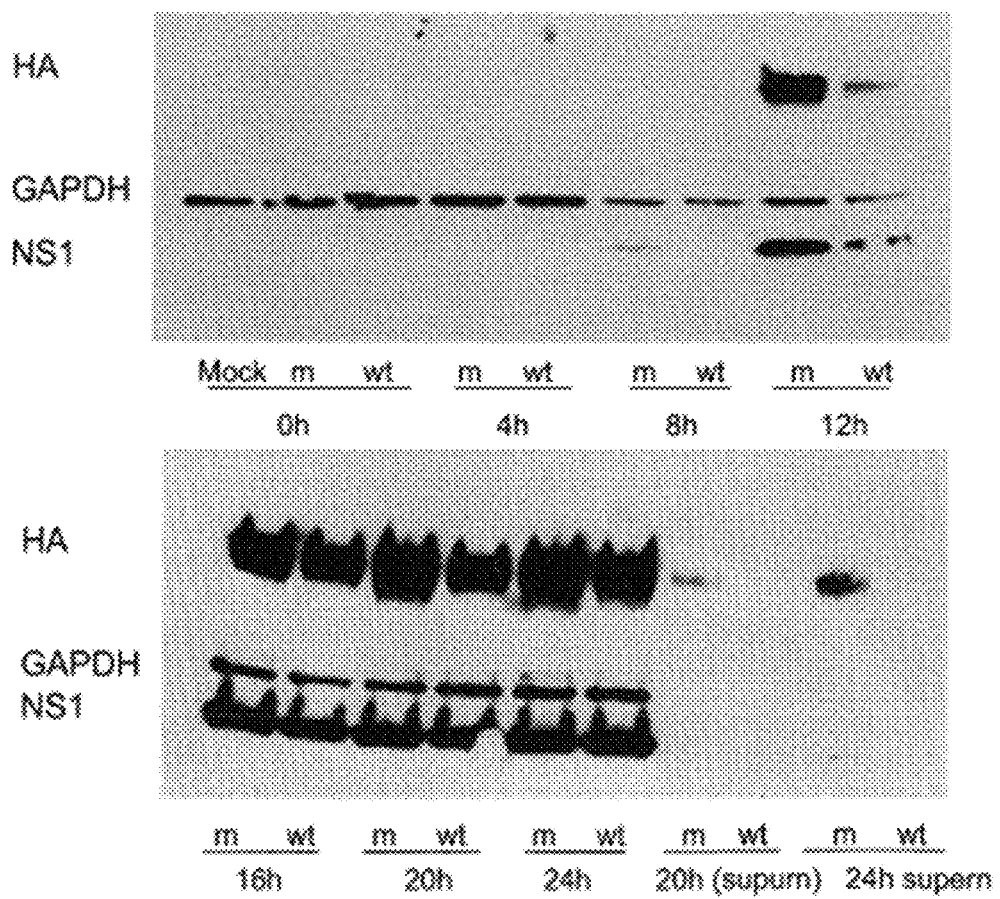
FIG. 3 shows the comparison of viral protein synthesis: HA and NS1 of 2 ma-Ca/04 H1N1:mPA (E59V):5WF10att (m) and 2 ma-Ca/04 H1N1:6WF10att (wt) at 0, 4, 8, 12, 16, 20, and 24 hpi in MDCK cells and at 20 and 24 h in the supernatants. Cellular GAPDH levels were used as internal control.
Figure 4A:
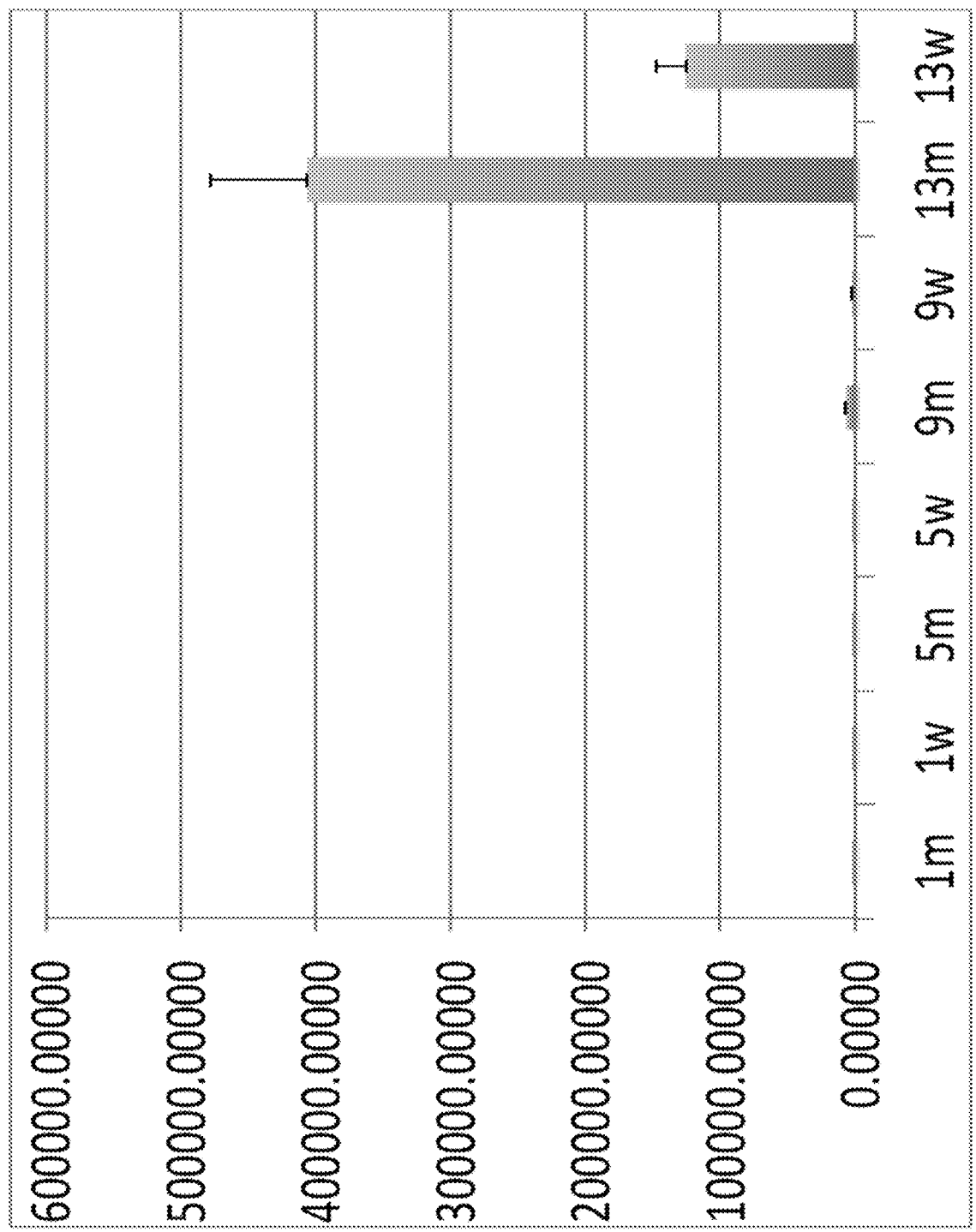
FIGS. 4A-E show the detection of HA and NP viral mRNA levels at early phase of infection in MDCK cells using real time RT PCR. The viral mRNA expression levels of HA (A) and NP (B) were detected using influenza virus segment specific tagged primers. Relative mRNA levels of HA (C) and NP (D) were calculated by comparing the expression level of 2 ma-Ca/04 H1N1:mPA (E59V): 5WF1att and 2 ma-Ca/04 H1N1:6WF10att at the indicated time points. The melting curve of real-time PCR products is shown in (E).
Figure 4B:
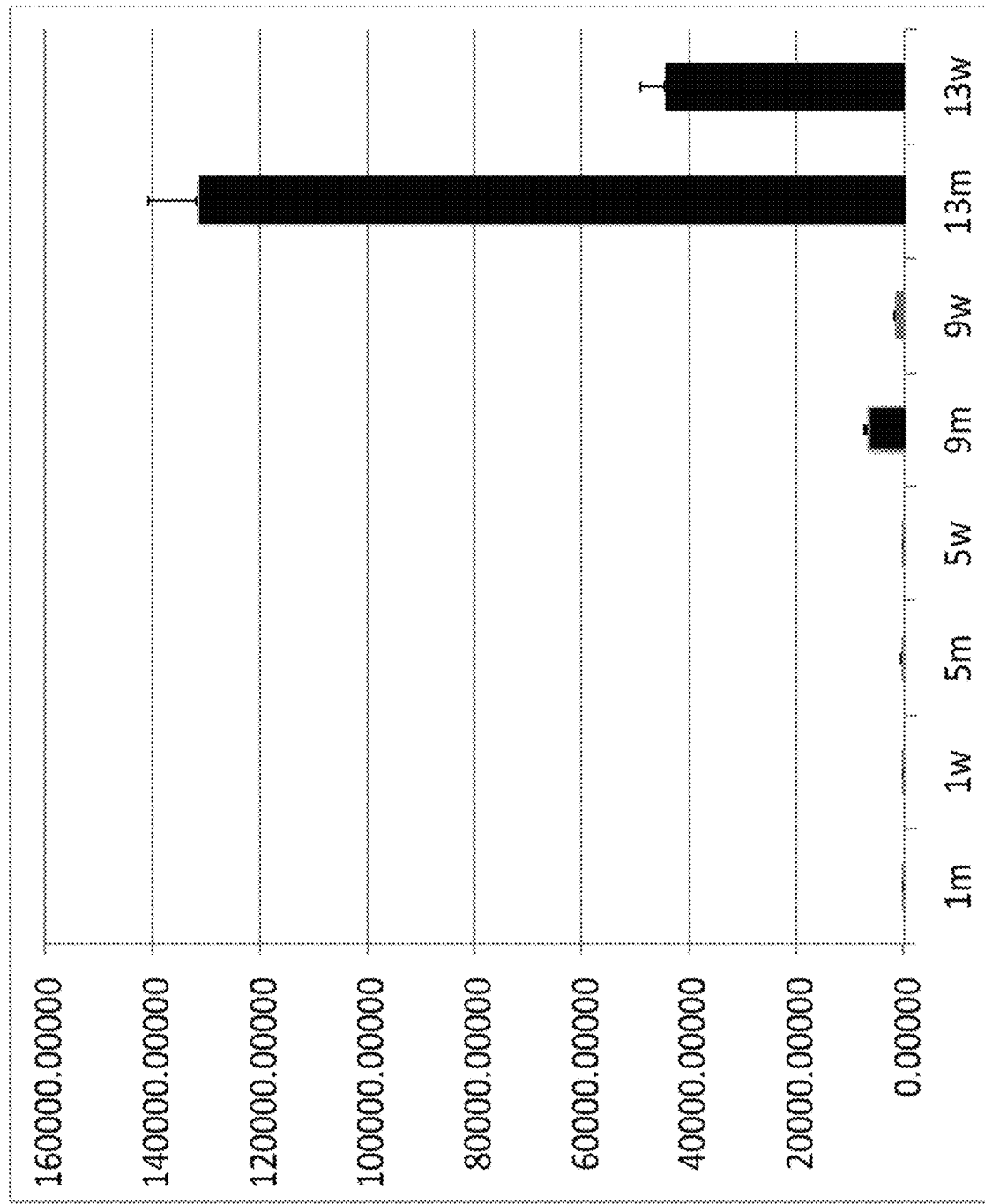
Figure 4C:
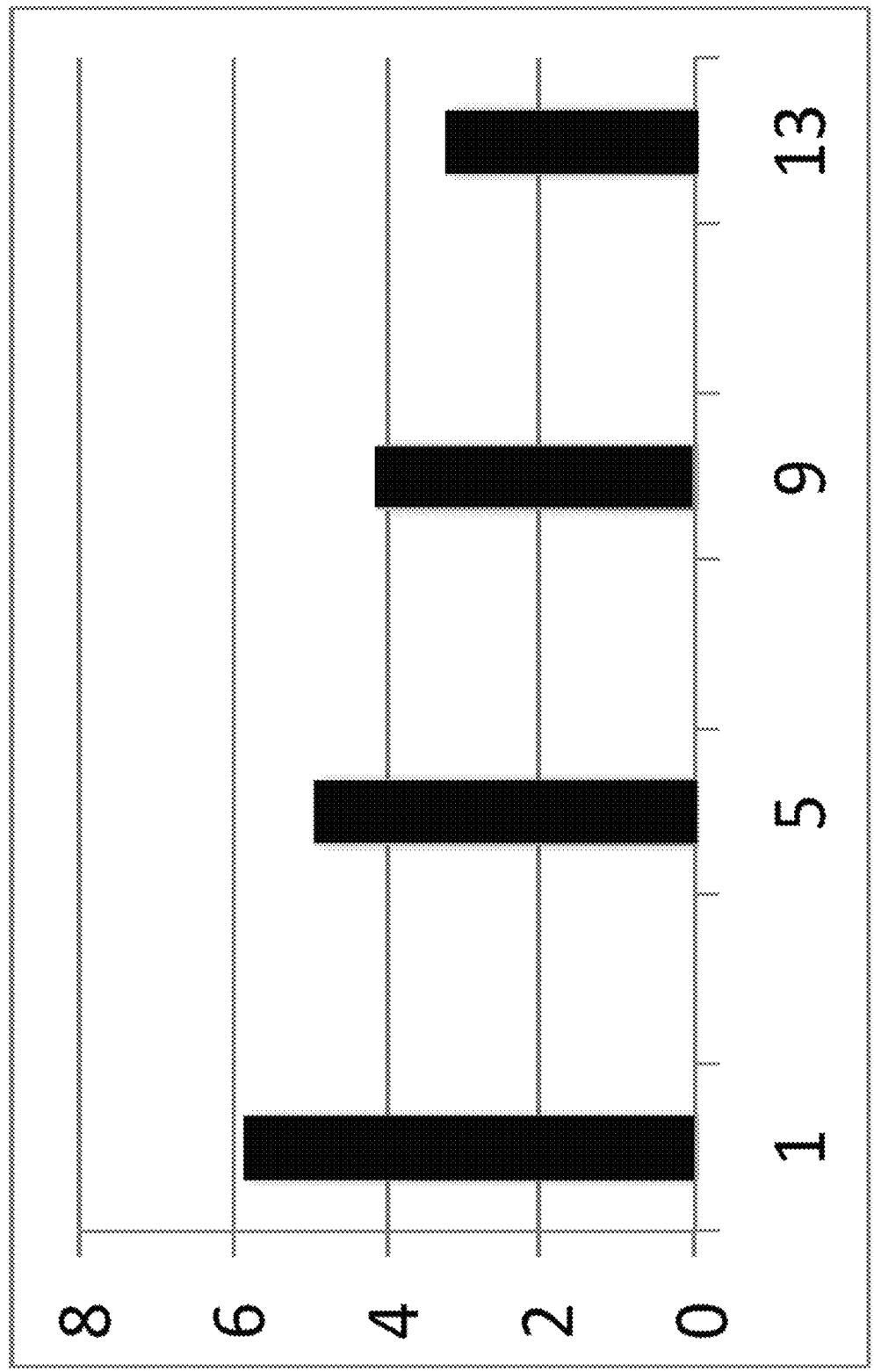
Figure 4D:
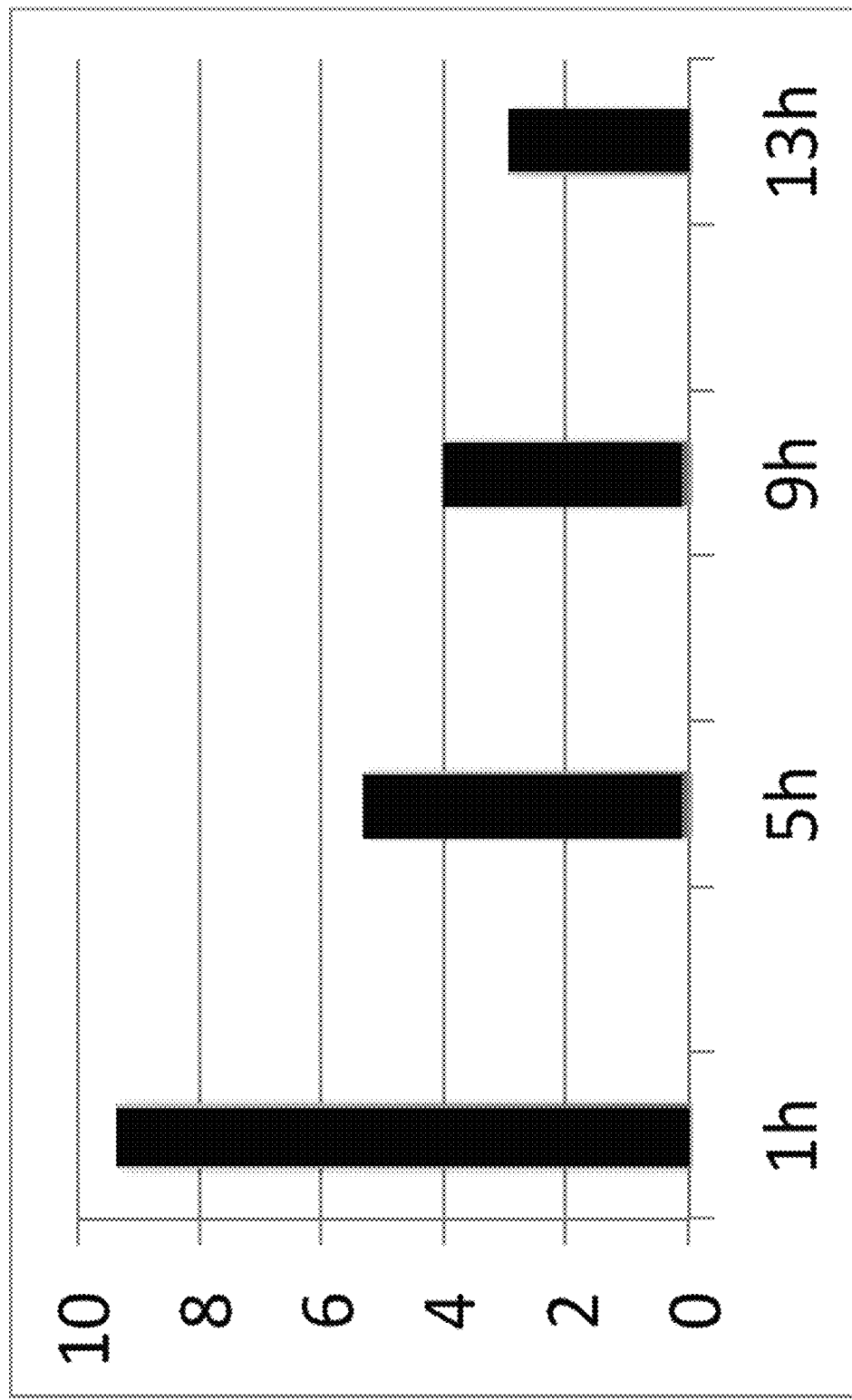
Figure 4E:
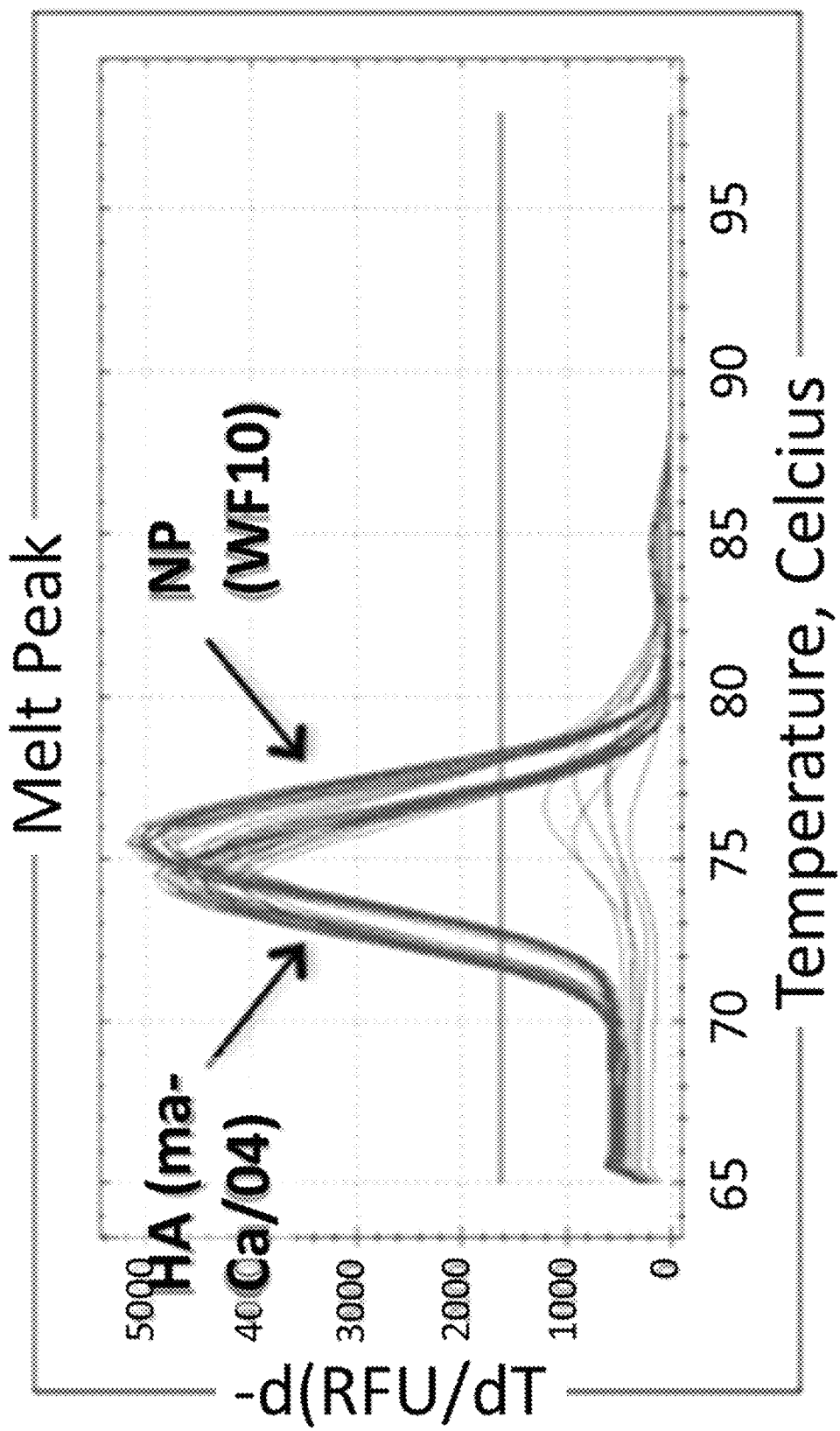

MDCK cells in 6-well plates were infected with 2 ma-Ca/04 H1N1:mPA (E59V):5WF10att or 2 ma-Ca/04 H1N1:6WF10att (MOI=0.1). The cell samples were collected every 4 h starting at 4 hpi until 24 hpi. Supernatant samples were collected at 20 and 24 hpi. Samples were treated with 2×SDS gel-loading buffer. Electrophoreses was performed on 10% SDS PAGE. The protein samples were transferred to nitrocellulose membrane, and the proteins detected using monoclonal antibodies against ma-Ca/04 H1N1 HA and WF10 NS1. The 2 ma-Ca/04H1N1:mPA:5WF10att synthesized viral proteins faster than 2 ma-Ca/04 H1N1:6WF10att (wt), which were readily observed in infected cells and supernatants (FIG. 3).

FIG. 4 shows that viral mRNAs were up regulated from 1 to 13 hpi in MDCK cells infected with both viruses. However, the virus possessing the mutated PA (E59V) showed increased mRNAs level in the early phase of infection compared to the virus with wt-PA: ma-Ca/04 (normalized to 0 in FIGS. 4C and D).

B. Example 2: Influenza Viruses with Rearranged Genomes as Live-Attenuated Vaccines The use of viral vectors for the delivery of traceable reporter genes and bioactive molecules has broad applications in the fields of gene therapy and infectious diseases. A number of live recombinant viral vectored vaccines have been licensed for veterinary use and many are in clinical development for humans (5). These vaccines combine positive features of DNA and live attenuated vaccines. Viral vectors deliver the nucleic acid encoding antigens into target host cells, with the added advantage of inducing more robust immune responses elicited by limited replication of the viral entity (5). Since the development of reverse genetic methods for segmented negative sense RNA viruses, influenza A viruses (IAV) have also been considered as potential vaccine vectors (14).

IAVs are single-stranded segmented RNA viruses of negative polarity that belong to the family Orthomyxoviridae. In IAVs, 8 RNA segments encode for 10-12 viral proteins, including two surface glycoproteins, hemagglutinin (HA), and neuraminidase (NA), which are the major targets for neutralizing antibody responses. The engineering of IAVs as vaccine vectors could offer several advantages: (i) IAVs induce strong immune responses systemically and at the mucosal surfaces (12), (ii) influenza replication does not have a DNA phase, eliminating safety concerns regarding integration of viral DNA into the host genome, (iii) IAVs have 16 HA and 9 NA subtypes that are antigenically distinct and which undergo constant antigenic drift making boost vaccinations feasible (8), and (iv) IAVs are well characterized with attenuated strains already used as vaccines for humans and livestock (3). Unfortunately, most IAV vectors developed to date contain a combination of either abortive replication and/or are either unstable, or tolerate only short gene inserts (21).

The avian H9N2s and the highly pathogenic avian influenza viruses (HPAIV) H5N1 pose a pandemic threat. The development of effective vaccines against these subtypes is an essential component of the WHO's global strategy for pandemic preparedness (30). Inactivated vaccines; particularly in the context of HPAIV H5N1, are poorly immunogenic and often require so the addition of an adjuvant and/or boosting to induce protective responses. LAIV vaccines provide broad cross-protective responses and do not require the use of adjuvants (3, 16). However, LAIVs using an H5 HA surface gene segment carry the potential for reassortment with seasonal and/or other influenza viruses (28, 29).

In this example, the IAV genome was rearranged and influenza vectors were generated that stably express foreign genes. Avian H9N2 IAV expressing enhanced green-fluorescent protein (eGFP), secreted Gaussia Luciferase (Gluc), and the entire HA ORF from a prototypic HPAIV H5N1 (A/NietNam/1203/04 (H5N1)) were successfully recovered. Expression of both HA proteins (H9 and H5) were detected in cells infected with the H9N2 virus expressing the H5 ORF (H9N2-H5). Notably, immunization of mice and ferrets with the H9N2-H5 virus protected against lethal H5N1 challenges. Because the H5 ORF expressed in this construct does not encode a functional genomic RNA, reassortment of the influenza H5 HA is very unlikely. Rearranged IAV vectors can be used for the development of improved vaccines against influenza and other pathogenic agents as well as facilitate studies of influenza pathogenesis in several biological systems.

1. Materials and Methods i. Ethics Statement.

Vaccination studies were conducted under BSL-2 conditions, whereas challenge with HPAIV H5N1 was performed under Animal Biosafety Level 3 (ABSL-3) conditions approved by the USDA. Animal studies were performed according to protocols approved by the Institutional Animal Care and Use Committee of the University of Maryland. Animal studies adhere strictly to the US Animal Welfare Act (AWA) laws and regulations.

ii. Viruses and Cell Lines.

Human embryonic kidney cells (293-T) were cultured in OptiMEM I (GIBCO, Grand Island, NY) containing 10% FBS and antibiotics. Madin-Darby canine kidney (MDCK) cells were maintained in modified Eagle's medium (MEM) (Sigma-Aldrich, St. Louis, (MO) supplemented with 5% fetal bovine serum (FBS) (Sigma-Aldrich) and antibiotics.

The H9N2 wt virus and the H9:pH1N1 reassortant have been previously described (17, 26). The HPAIV A/Nietnam/1203/04 (H5N1) [hereafter H5N1 wt] was a kind gift from Ruben Donis, CDC, Atlanta, Georgia, USA. Recombinant viruses used in this paper were generated from cloned cDNAs and are described below and in the Table 1. All the viruses were propagated in 7-10 day old embryonated hens eggs and titrated by at least one of the so following methods: egg infectious dose 50% (EID50), tissue culture infectious dose 50% (TCID50), or mouse lethal dose 50% (MLD50).

iii. Generation of Recombinant Viruses.

The eight plasmid reverse genetic system for H9N2 wt has been previously described and it is based in the bidirectional plasmid vector pDP2002 (26). The HA and NA genes from the H5N1 wt strain were cloned into pDP2002 vector. The ΔH5 HA plasmid encodes the HA segment from H5N1 wt, which has been further modified by the removal of the encoded polybasic cleavage site. To generate H9N2 wt with ∂NS1 (∂H9N2), the NS segment was modified so it encodes a C-terminus-truncated NS1 protein product comprising of amino acids 1 to 99 and an unmodified NEP/NS2 protein.

Rearrangement of the influenza genome was accomplished by expressing the NEP/NS2 protein from a single polypeptide downstream of the PB1 gene. Foreign genes of interest are cloned downstream of a full-length or truncated NS1 gene between two AarI cloning sites so that there is no introduction of exogenous sequences. Three nucleotide mutations were introduced in the full-length NS1 by site-directed mutagenesis to prevent residual splicing and/or NS2 expression. The splicing donor site was modified from G to A at position 56, and a stop-codon early in NS2 and out of frame with NS1, was inserted via C548A mutation (22). As an additional step, the branch point adenosine at position 509 was modified to cytosine. Processing of the PB1-NEP/NS2 and NS1-foreign gene proteins is achieved by the in incorporation of the foot-and-mouth disease virus (FMDV) 2A cis-acting hydrolase element (CHYSEL)(4) downstream of PB1 and NS1, respectively. The corresponding packaging signals previously determined for RNA segments 2 and 8 were maintained to achieve efficient vRNA incorporation into virions (7, 18). All the plasmid constructs and recovered recombinant viruses were fully sequenced to confirm their identities.

iv. Minigenome Assay.

The minigenome assay was performed as described previously (23). The PB1 attenuated plasmid (PB1 att) used here as a control, has been previously published and contains the K391E, E581G, and A661T mutations and an HA tag sequence fused in frame with the C-terminus of the PB1 protein (26).

v. Growth Kinetics.

MDCK cells were seeded in 6-well plates and infected in triplicate at MOI of 0.01. Following adsorption for 1 h, the monolayers were washed 3 times with PBS and 2 ml of OptiMEM media containing 1 μg/ml TPCK-trypsin was added. Plates were incubated at 37° C. and cell culture supernatant was harvested at 0, 12, 24, 48, 72, and 96 hpi. Viral titers were determined by TCID50 in MDCK cells.

vi. Immunoelectron Microscopy.

Recombinant viruses were purified by sucrose density gradient centrifugation. Purified viruses were adsorbed to formvar/silicon monoxide-coated nickel grids (Electron Microscopy Sciences, Hatfield, PA). The grids were blocked in PBS containing 0.2% BSA and incubated with in-house produced mouse monoclonal antibodies specific for the H5 or H9 HA. Grids were washed in blocking solution and incubated in goat anti-mouse IgG antiserum conjugated to 6 nm gold beads (Aurion, Costerweg 5, The Netherlands). The grids were then negatively stained with 2% phosphotungstic acid (PTA) for 3 min, dried, and examined under a transmission electron microscope.

vii. Mouse Studies.

Five-week-old female BALB/c mice (Charles River Laboratories, Frederick, MD) were anaesthetized with isofluorane prior to intranasal inoculation. Mice were vaccinated with 50 μl 105 egg infectious dose 50 (EID50) of the recombinant viruses diluted in PBS. A boost immunization was given in half of the animals 2 weeks after the first inoculation. Each experimental group contained 30 animals. Mice were divided into 4 groups as follows: a) PBS (negative control); b) H9N2-GFP (vector control); c) H9N2-H5 (test vaccine); and d) ΔH5N1 (positive control for the H5N1 vaccine). At 2 weeks post-vaccination (or 2 weeks post-boost for animals immunized twice), each group was divided into 3 subgroups (n=10) and intranasally challenged with either 20, 200, or 2000 mouse lethal dose 50% (MLD50) of the HPAIV A/Vietnam/1203/04 (H5N1) strain. Mice were bled using the submandibular bleeding method (11) prior to inoculation and at several time points after immunization to evaluate the immunogenicity of the vaccines. At 5 dpc, 3 mice from each subgroup were euthanized and their lungs were collected to measure levels of challenge virus. Tissue homogenates were prepared in PBS, clarified by centrifugation, and stored at −70° C. until use. Clinical signs of disease, body weight, and mortality were monitored daily throughout the experiment to evaluate vaccine safety and efficacy. Mice presenting ≥25% body weight loss were humanely euthanized and counted as have succumbed to the infection.

Alternatively, 5 groups of mice (n=8) consisting of the same treatment groups as above and an additional ∂H9N2 virus control were immunized twice intranasally (2 weeks apart) with 105 EID50/mouse. At 2 weeks post-boost, animals were challenged with 106 TCID50/mouse of the H9:pH1N1 reassortant virus (17). Four animals from each were euthanized at 3 dpc and the remaining 4 animals at 5 dpc for virus titration in the lungs.

viii. Ferret Studies.

Twelve female Fitch ferrets, 3 to 6 months-old, were purchased from Triple F Farms (Sayre, PA) and divided in 4 groups (n=3/group). Only IAV seronegative animals were used. Prior to vaccination, ferrets received a subcutaneous implantable temperature transponder (Bio Medic Data Systems, Seaford, DE) and were monitored for 5 to 7 days to measure body weight and establish baseline body temperatures. Ferrets were intranasally immunized twice 2 weeks apart with 500 μl containing 105 EID50 of the recombinant viruses diluted in PBS, as indicated above. At 2 weeks after boost, ferrets were challenged with a lethal dose ($10^6$ EID50) of the HPAIV H5N1 A/Vietnam/1203/2004 strain. Body weight changes, clinical signs of disease including fever and mortality were monitored daily throughout the experiment as parameters for vaccine evaluation. Nasal washes were collected for 7 days after each vaccination and for 9 dpc to quantify virus shedding. Blood samples were collected at 0, 14, and at 28 dpv. A final bleed was performed at 15 dpc.

ix. Chicken Studies.

Two-week-old specific-pathogen-free leghorn chickens were inoculated intravenously (n=2, Table 1) or through a combination of natural routes (n=5 intranasal, intraocular, oral, and intratracheal) with $10^7$ EID50 of the rearranged HPAIV H5N1. Morbidity and mortality was followed for 10 days after inoculation.

TABLE 1

| Viruses | Genome modification | Transgene | Virus subtype | Acronym |
|---|---|---|---|---|
| A/Guinea fowl/Hong Kong/WF 1099 (H9N2)[a] | none | none | H9N2 | wt H9N2 |
| A/VietNam/1203/04 (H5N1)[b] | none | none | H5N1 | wt H5N1 |
| Non-rearranged H9N2-∂NS1[c] | NS1 truncation | none | H9N2 | ∂H9N2 |
| Rearranged H9N2-∂NS1-GFP[d] | NS1 truncation and rearrangement | GFP | H9N2 | H9N2-GFP |
| Rearranged H9N2-∂NS1-GLuc[e] | NS1 truncation and rearrangement | GLuc | H9N2 | H9N2-GLuc |
| Rearranged H9N2-∂NS1-Δ5 Orf[f] | NS1 truncation, rearrangement, and modified cleavage site in HA | Modified H5 HA | H9N2-H5 | H9N2-H5 |
| Surface genes from ΔH5N1 in non-rearranged H9N2-∂NS1 backbone[g] | NS1 truncation and and modified cleavage site in HA | none | H5N1 | ΔH5N1 |
| Rearranged H5N1 WT[h] | rearrangement | GFP | H5N1 | none |
| H9:pH1N1 reassortant[i] | none | none | H9N1 | H9:pH1 N1 | x. Statistical Analysis.

Statistical analyses were performed using GraphPad Prism Software Version 5.00 (GraphPad Software Inc., San Diego, CA). Comparison between two treatment means was achieved using a two-tailed Student t-test, whereas multiple comparisons were carried out by analysis of variance (ANOVA) using Tukey's post hoc test, unless otherwise specified. The differences were considered statistically significant at $p<0.05$.

2. Results i. Generation of Influenza Virus Vectors with Rearranged Genomes Expressing Reporter Genes.

The IAV RNA segment 8 codes for two proteins: NS1, a nonstructural protein that inhibits the host's antiviral response; and NEP/NS2, a structural protein involved in viral assembly and gene regulation. NS1 is produced from an unspliced mRNA, whereas NEP/NS2 is expressed from a spliced mRNA (24). Here, reverse genetics was used to rearrange the genome of an avian IAV, A/Guinea Fowl/Hong Kong/WF10/99 (H9N2)(26)—herein referred to as wt H9N2. This strain was used because it grows well in eggs and tissue culture and has been shown to replicate in several animal species such as mice, chicken and ferrets without previous adaptation (13, 26). In addition, it was previously shown that LAIVs based on the wt H9N2 background have adequate attenuation and protection efficacy profiles (12, 25, 26).

Rearrangement of the influenza genome was accomplished by expressing the NEP/NS2 ORF from a single polypeptide downstream of the PB1 gene. Introducing the foot-and-mouth disease virus (FMDV) 2A autoproteolytic cleavage site between the PB1 and NEP/NS2 ORFs allowed co-translational release of the latter from the upstream PB1-2A chimeric protein (FIG. 5a). Removing the NEP/NS2 gene from RNA segment 8 resulted in additional cloning space in this segment. The expression of the transgene of interest was achieved by cloning it downstream of either a full-length or a truncated NS1 gene (expressing the first N-terminal 99 aa). The FMDV 2A was cloned between NS1 and the transgene to enable discrete expression of the foreign protein. To prevent any residual splicing activity, the donor site and branch point within full-length NS1 were mutated and a stop-codon was inserted early in the residual open reading frame of NS2 (22). The corresponding packaging signals previously determined for RNA segments 2 and 8 were maintained to optimize incorporation of the modified viral ribonucleoprotein particles (vRNPs) into virions (7, 18). As proof of principle for this approach, the GFP and the GLuc transgenes were cloned into this vector, ultimately resulting in virus rescue (FIG. 5, details of the virus constructs are described in Table 1). These recombinant IAVs reached titers in the order of 6-7 $\log_{10}$ EID50/ml after amplification in embryonated eggs and transgene expression was maintained up to 10 passages. Expression of both GFP and GLuc reporter genes was readily detected either in the cytoplasm or in the supernatant, respectively, of infected MDCK cells (FIG. 5b).

ii. The H5 HA Expressed from Segment 8 is Incorporated into the Envelope of the Rearranged H9N2 Vector.

A rearranged IAV vaccine vector was developed in which the HA ORF from A/Nietnam/1203/04 (H5N1) was cloned downstream of a truncated NS1 gene (NS1-99 aa) in the rearranged H9N2 vector. A ΔH5 HA was used with a monobasic cleavage site as previously described (1). The recombinant H9N2-H5 virus was successfully recovered and propagated in embryonated eggs. Cells infected with the H9N2-H5 virus expressed high levels of both HA subtypes as determined by immunofluorescence assay (IFA) using HA subtype specific monoclonal antibodies (mAb).

Previous studies have demonstrated the surface incorporation of two different HAs (H1 and H3 subtypes) by a recombinant influenza virus containing 9 RNA segments (8). Whether the H5 HA could be incorporated into virions was determined. The H9N2-H5 virus showed typical influenza virus morphology, consisting of pleomorphic particles and roughly spheroidal virions of approximately 100 nm in diameter. Immunogold electron microscopy using anti-H5 and anti-H9 specific mAb revealed that both HAs were incorporated into the envelope of the H9N2-H5 virus. As expected, H5 and H9 control viruses only reacted with the respective mAb (FIG. 5d). These results indicate that rearranged IAV vectors retained the typical virion morphology and that both HA proteins were incorporated into the eight-segmented H9N2-H5 rearranged vector.

iii. Genome Rearrangement Leads to Impaired Polymerase Activity and Reduced Viral Growth In Vitro.

Figures 6A, 6B:
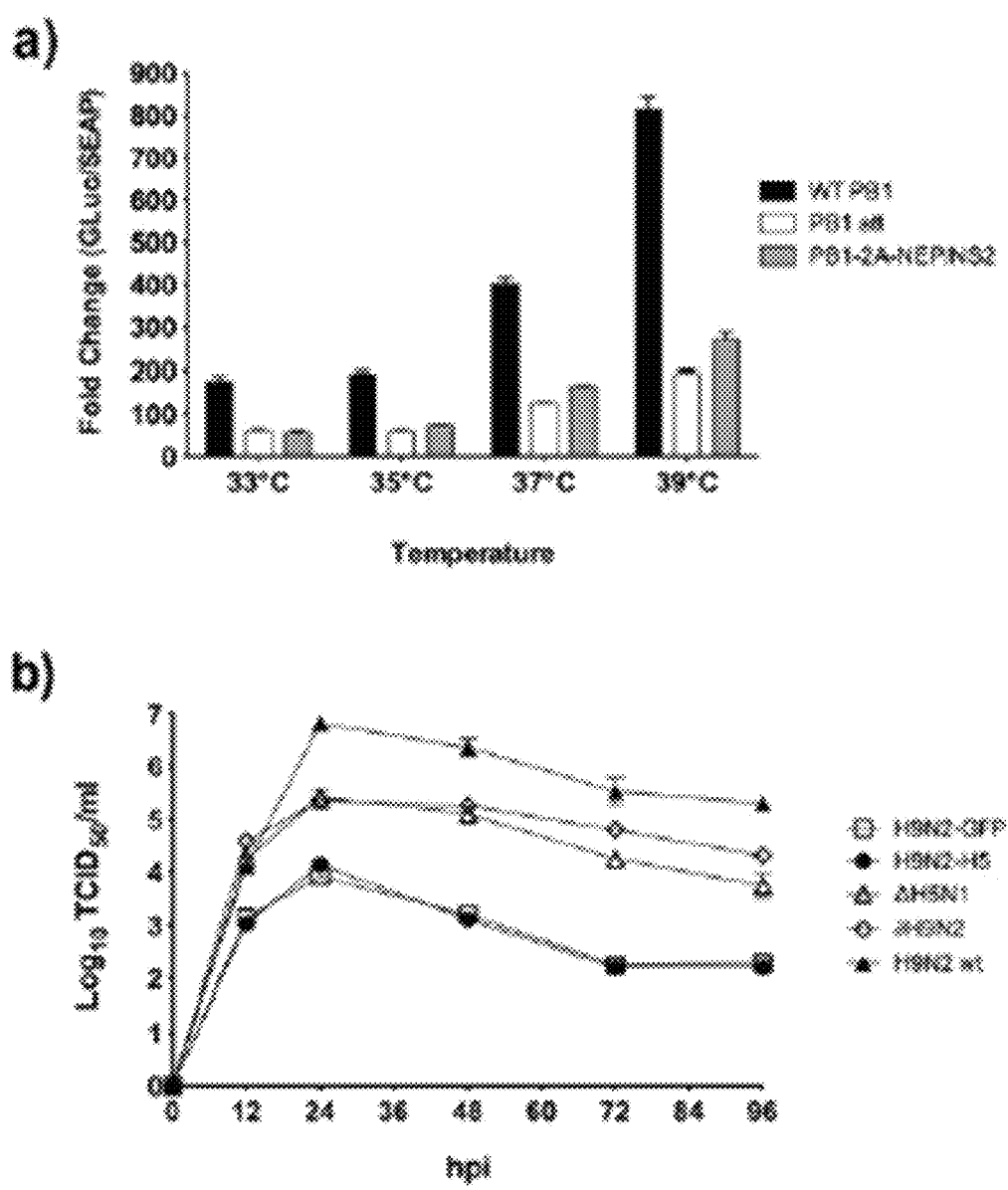

To study the effects of genome rearrangement in viral polymerase activity, a minigenome assay was performed as previously described (23). The presence of PB1-2A-NEP/NS2 led to significantly lower polymerase activities than that with the wt PB1 gene at different temperatures (FIG. 6a). These results indicate that the strategy used to rearrange the IAV genome decreases viral polymerase activity.

To evaluate whether the reduction in polymerase activity would result in decreased virus replication, the growth properties of the rearranged H9N2-GFP and H9N2-H5 viruses was evaluated in MDCK cells infected at multiplicity of infection (MOI) of 0.01. In agreement with the minigenome assay, rearranged viruses harboring a truncated NS1 had 10-100 fold reduction in virus titers compared to non-rearranged viruses containing the same NS1 deletion. Both wt and rearranged viruses reached maximum viral titers at 24 hours post-infection (hpi) (FIG. 6b). Together, these results indicate that rearranged viruses can undergo multiple cycles of replication in MDCK cells, although peak titers are at least 10-fold less compared to wt isogenic virus.

iv. Genome Rearrangement Strongly Attenuates Influenza Vectors In Vivo.

To evaluate the safety profile of the rearranged IAV vectors, studies were performed in mice, ferrets, and chickens. BALB/c mice were intranasally inoculated with $10^5$ EID50/mouse of either H9N2-GFP or H9N2-H5 rearranged vectors. Additional groups included a PBS control; a non-rearranged ΔH5N1 virus (containing the surface genes derived from a low pathogenic A/Vietnam/1203/04—polybasic cleavage site in HA removed—in the background of the NS1-truncated H9N2 wt virus); a non-rearranged ∂H9N2 virus (NS1-truncated H9N2 wt virus) and the wt H9N2 virus (Table 1).

Figures 6C, 6D:
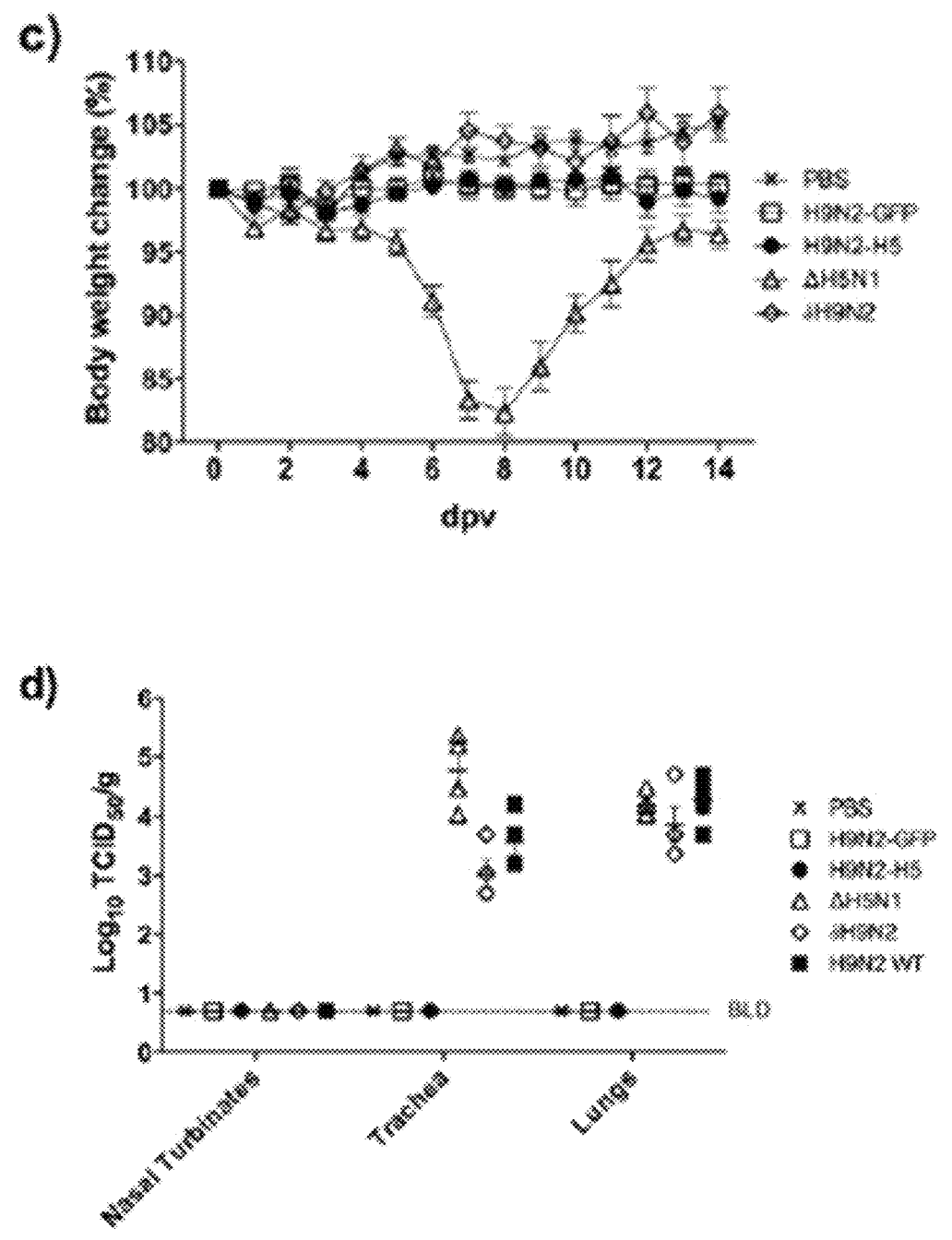
Figures 6E, 6F:
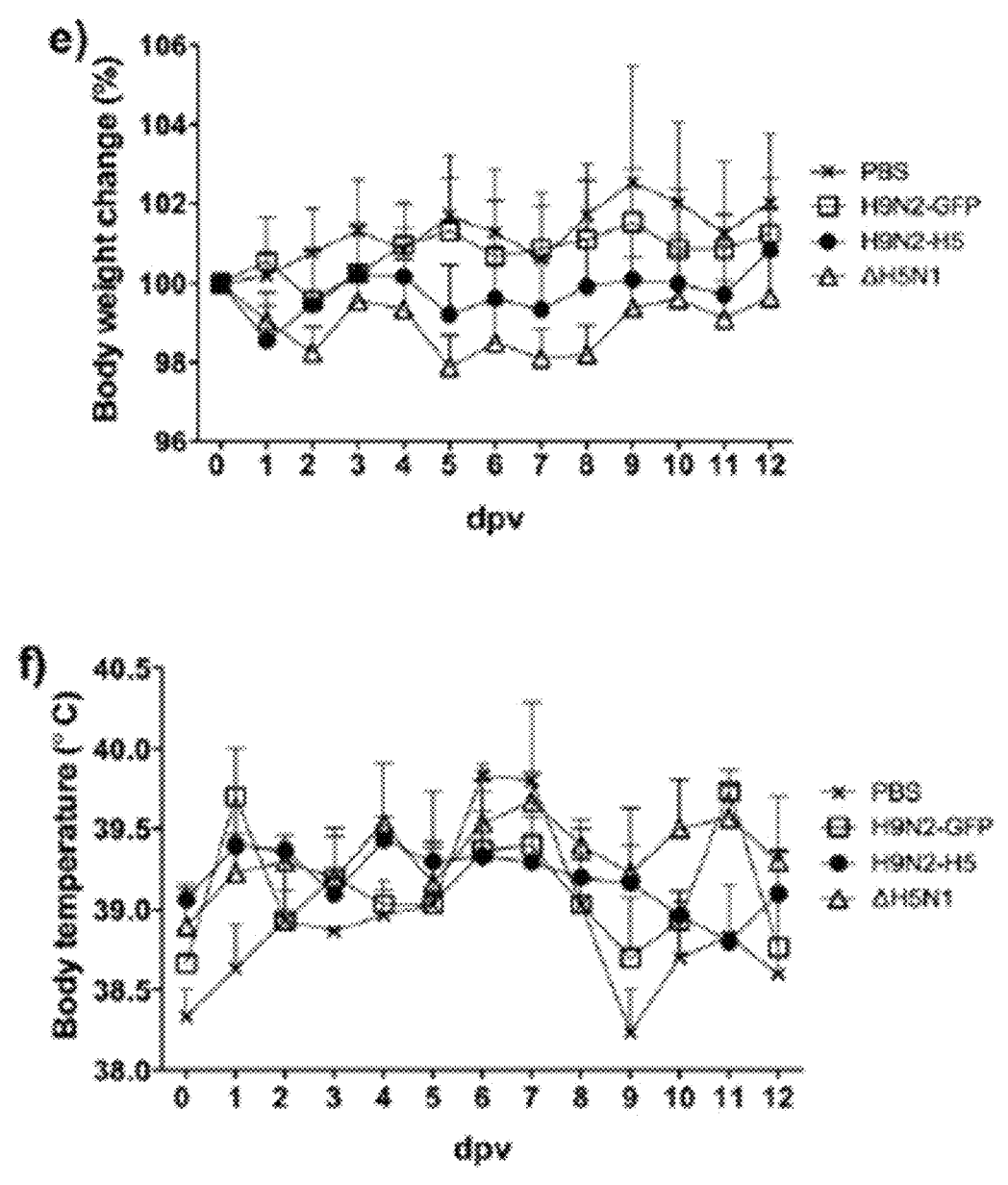

Vaccination of mice with the rearranged H9N2 vectors produced no clinical disease signs and there was no change in body weight. Conversely, mice inoculated with the ΔH5N1 virus showed significant body weight loss (≤20%) by 8 dpi, although they eventually recovered (FIG. 6c). In examining tissue tropism and viral replication at 3 dpi, the rearranged H9N2 vectors were not detected in the respiratory tract, whereas the ΔH5N1 and ∂H9N2 replicated to high virus titers in the respiratory tract of mice (FIG. 6d). A similar study conducted in ferrets confirmed the safety features of rearranged viruses as determined by the absence of clinical signs of disease (FIGS. 6e and f) and no detecT-able 4irus shedding upon vaccination.

Because the H5 HA is expressed from the H9N2-H5 virus as a chimeric HA segment with the packaging signals of the NS gene, the possibility of reassortment of the H5 HA is remote (9). Nevertheless, genetic reassortment could take place if a circulating IAV exchanges both RNA segments 2 and 8 with the rearranged IAV. Therefore, this question was addressed by rescuing an H5N1 virus containing 6 wt RNA segments (1, 3, 4, 5, 6, and 7) from the HPAIV A/Vietnam/1203/04 (H5N1) strain and 2 segments (PB1-2A-NEP/NS2 and NS1-2A-GFP, encoding a full-length NS1) derived from the rearranged H9N2 virus. The pathogenicity of the rearranged HPAIV H5N1 was evaluated in chickens. Leghorn chickens were inoculated intravenously or through natural routes with a total of $10^7$ EID50 of the rearranged HPAIV H5N1 and followed clinically. None of the chickens died or developed clinical signs of disease upon inoculation. This indicates that even if the rearranged virus reasserted with a HPAIV H5N1, the resulting virus would be completely attenuated. Together, these results indicate that rearranged-based IAV vectors exhibits desirable safety features in three animal species.

v. Rearranged H9N2-H5 Virus Provides Protection Against Lethal H5N1 Challenge.

Figures 7A, 7B, 7C:
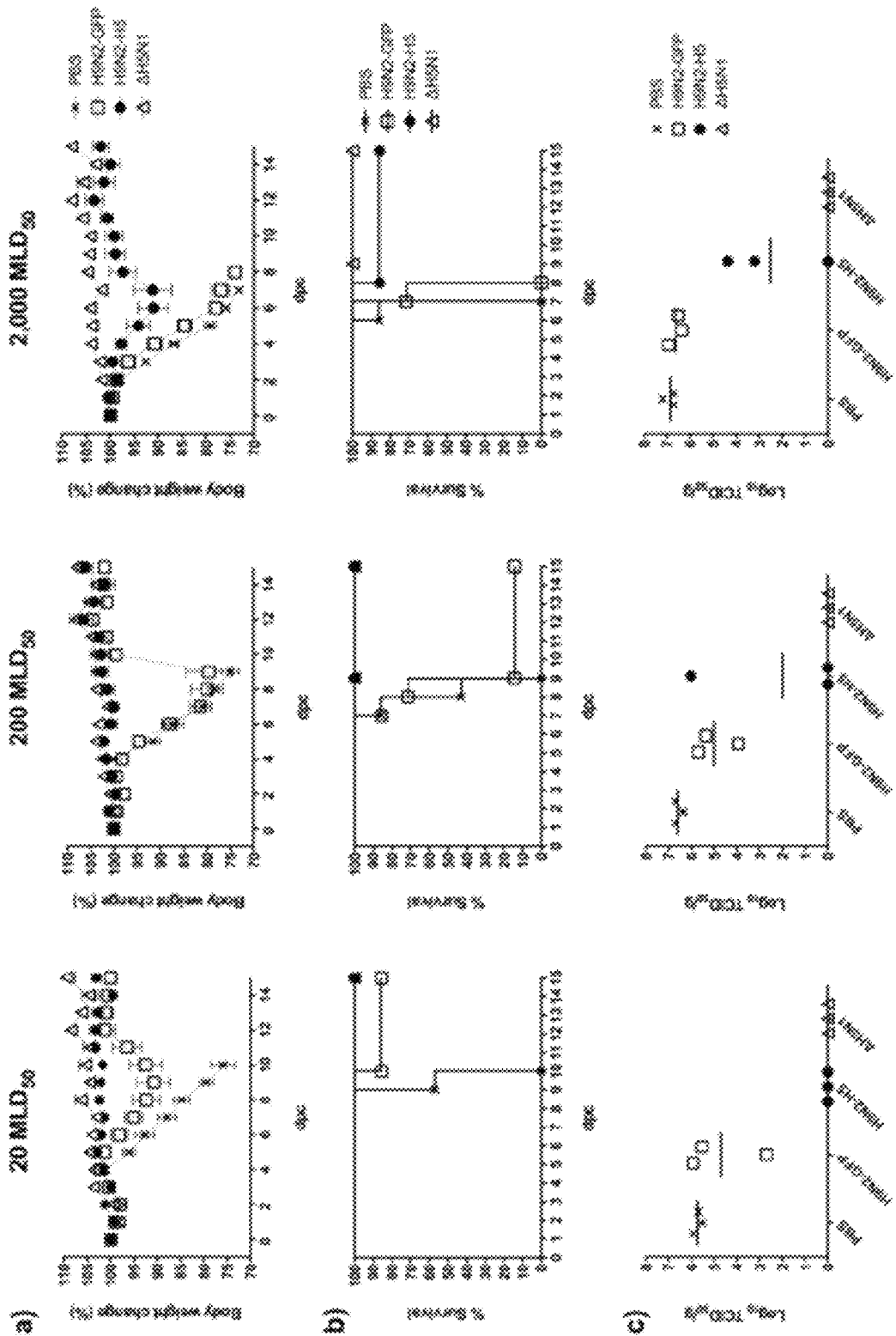
FIGS. 7A-7C show the protective efficacy of the H9N2-H5 rearranged influenza vector against HPAIV H5N1 challenges in mice after a single immunization. BALB/c mice (n=30) were intranasally vaccinated with 105 EID50/mice of the recombinant viruses. At 2 weeks post-vaccination, each treatment group was divided into 3 subgroups (n=10) and challenged with either 20 (left column), 200 (middle column), or 2000 (right column) mouse lethal dose 50% (MLD50) of the virulent A/VietNam/1203/04 (H5N1) strain by the intranasal route. Percent body weight change, n=7 (a), survival, n=7 (b), and virus titers (mean±SEM of log 10 TCID50/gram) in lung homogenates, n=3 (c).

The ability of the rearranged H9N2-H5 virus to induce protective immune responses was assessed in mice and ferrets. BALB/c mice were intranasally vaccinated once (FIG. 7) or twice (FIG. 8) with $10^5$ EID50/animal with the following: a) PBS (negative control); b) H9N2-GFP (vector control); c) H9N2-H5 (test vaccine); and d) ΔH5N1 (positive control for the H5N1 vaccine). At 2 weeks post-vaccination (or 2 weeks post-boost for animals immunized twice), each group (n=30) was divided into 3 subgroups (n=10) and challenged with either 20, 200, or 2,000 mouse lethal dose 50% ($MLD_{50}$) of the A/Vietnam/1203/04 (H5N1) strain. Three mice from each subgroup were euthanized at 5 dpc to evaluate the levels of challenge virus replication and, therefore, were not included in the survival analysis. A single dose of the H9N2-H5 vector provided complete protection from morbidity and mortality following challenges with 20 and 200 $MLD_{50}$ of HPAIV H5N1 (FIG. 7). The subgroup challenged with 2,000 $MLD_{50}$ lost an average of ≤10% of body weight by 7 days post-challenge (dpc), but the animals recovered with the exception of a single mouse that succumbed to infection (FIG. 7a). In contrast, the group singly immunized with the H9N2-GFP vector was not fully protected since all animals developed clinical disease and lost body weight with any challenge dose. The mortality rate in this group was 14%, 86%, and 100% for the 20, 200, or 2,000 $MLD_{50}$ challenge doses, respectively (FIG. 7b). Protection against pulmonary viral replication mirrored the clinical performance of the vaccines (FIG. 7c).

Figures 8A, 8B, 8C:
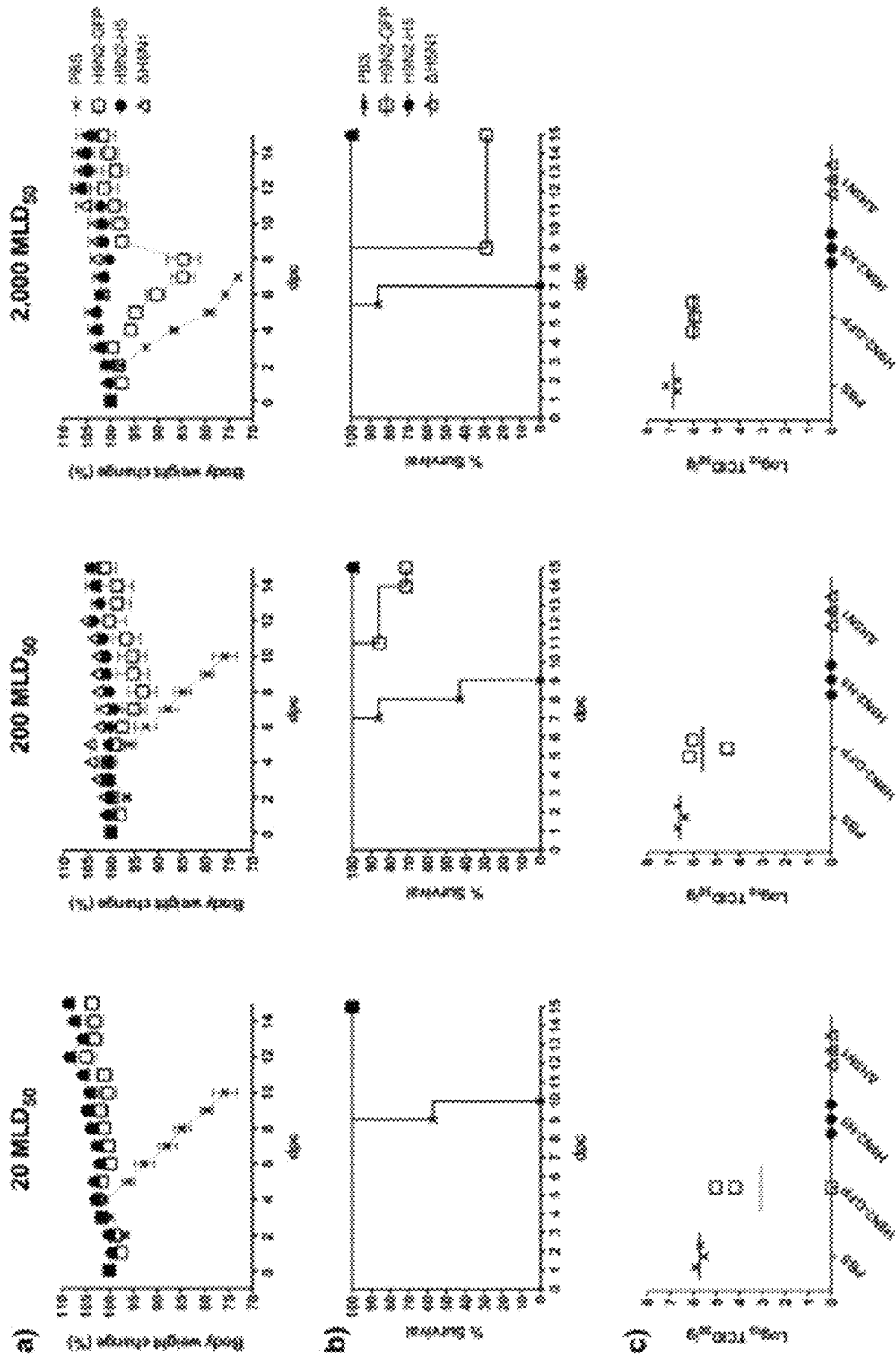
FIGS. 8A-C show the protective efficacy of the H9N2-H5 rearranged influenza vector in mice against HPAIV H5N1 challenges after boost immunization. BALB/c mice (n=30) were intranasally inoculated with 105 EID50/mice of the recombinant viruses and similarly at 2 weeks post-vaccination. At 2 weeks post-boost, each treatment group was divided into 3 subgroups (n=10) and challenged with either 20 (left column), 200 (middle column), or 2000 (right column) mouse lethal dose 50% (MLD50) of the virulent A/VietNam/1203/04 (H5N1) strain by the intranasal route. Percent body weight change, n=7 (a), survival, n=7 (b), and virus titers (mean±SEM of log 10 TCID50/gram) in lung homogenates, n=3 (c).

Importantly, a second dose of H9N2-H5 vaccine resulted in complete clinical protection and sterilizing immunity in all individuals regardless of the challenge dose used (FIG. 8). In the H9N2-GFP group, boost vaccination elicited protection from morbidity against 20 MLD50 challenge. However, these animals had approximately $10^3$ TCID50 of virus/g of lung tissue. Challenge with 200 and 2,000 MLD50 overcame the cross-protective immunity induced by the H9N2-GFP vector as indicated by 29% and 72% mortality rates, respectively, and high levels of replicating challenge virus in the lungs ($10^5$ to $10^6$ TCID50 of virus/g of lung) (FIG. 8c). The H9N2-H5 vaccine also provided sterilizing immunity in mice challenged with a highly transmissible avian H9 virus, a reassortant between a ferret-adapted H9N2 wt HA and the remaining 7 genes from pH1N1(17). Collectively, these results demonstrate that the rearranged H9N2-H5 vector is suitable for prime/boost vaccination protocols and protects against H5 and H9 challenges.

Figure 9A:
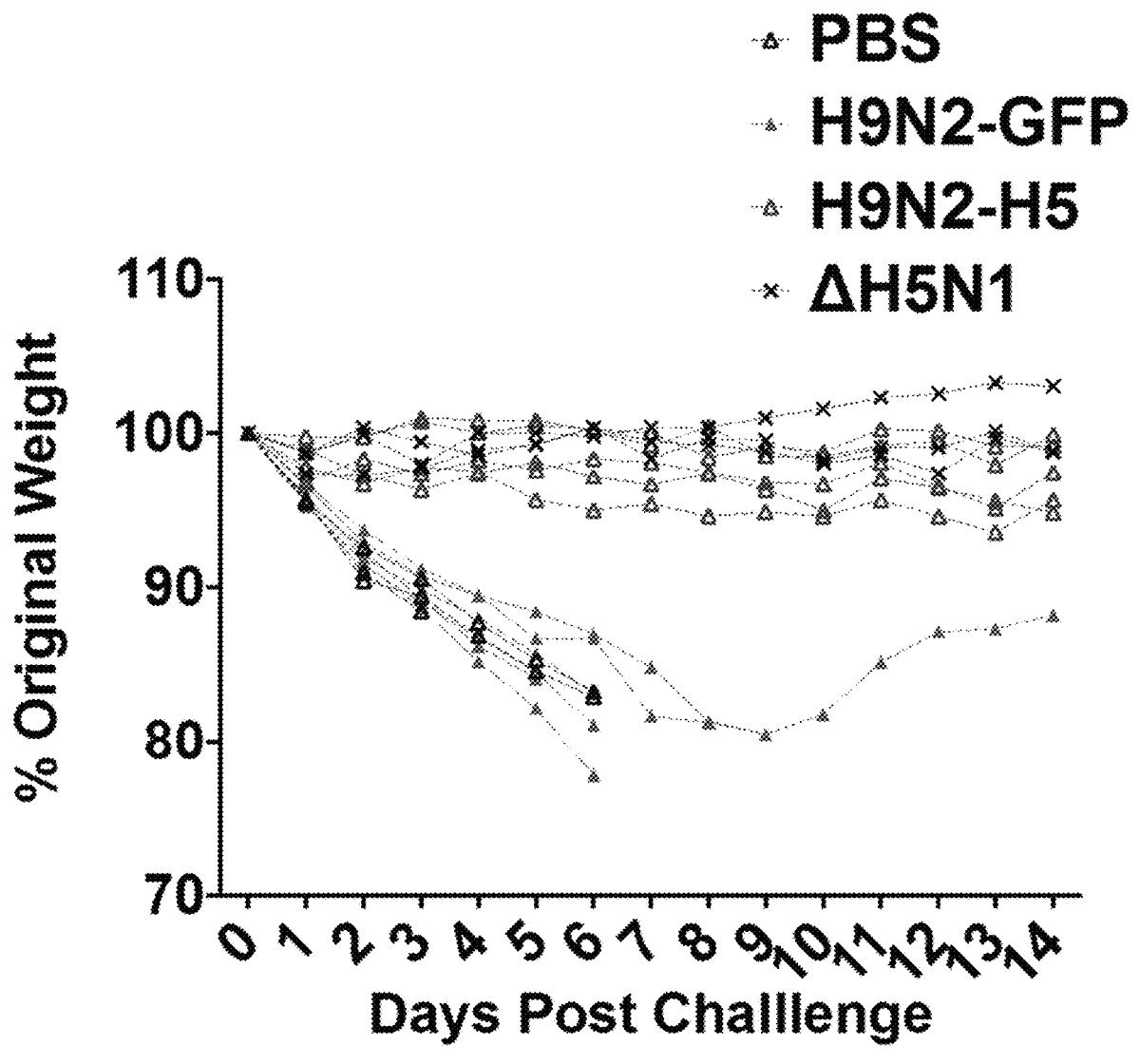
Figure 9B:
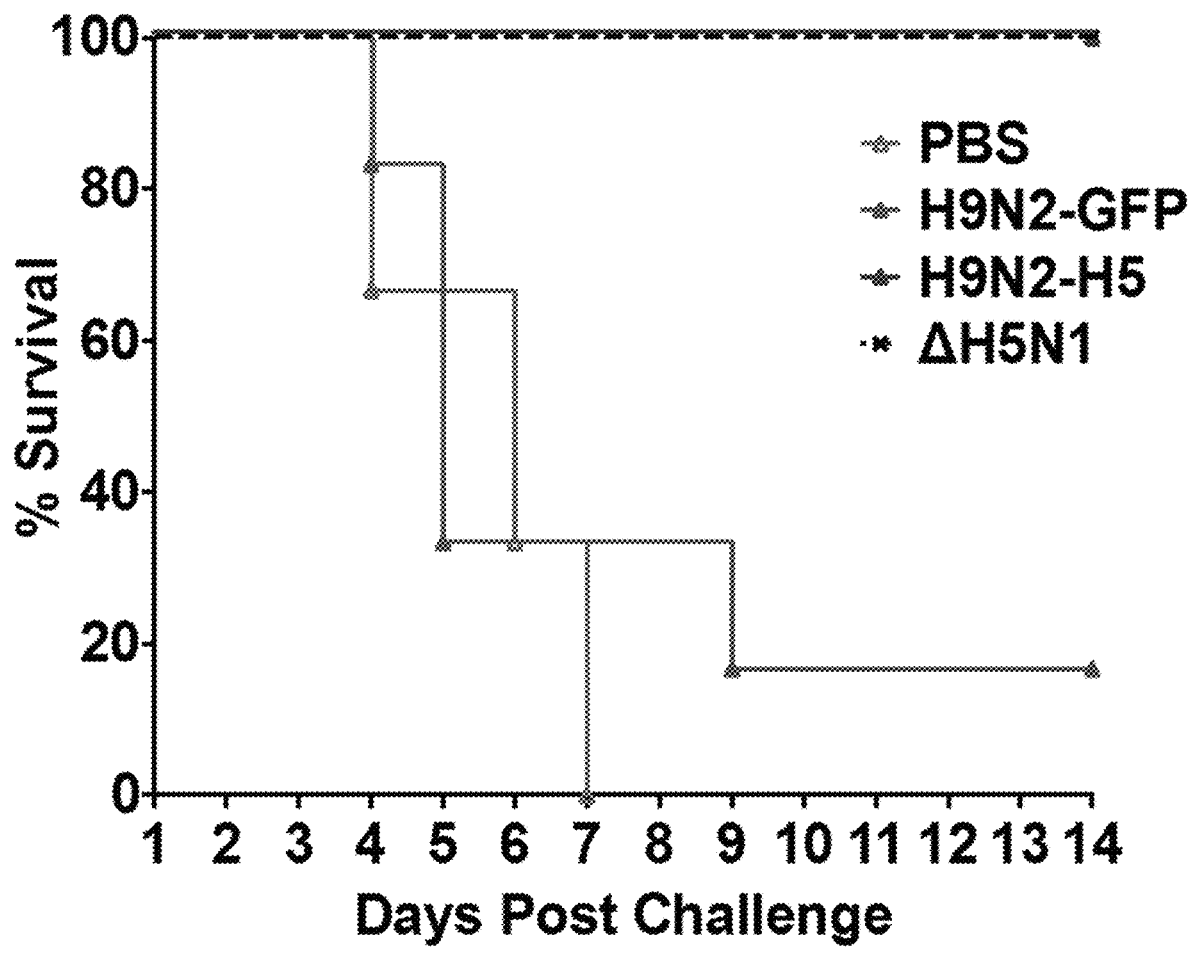
Figure 9C:
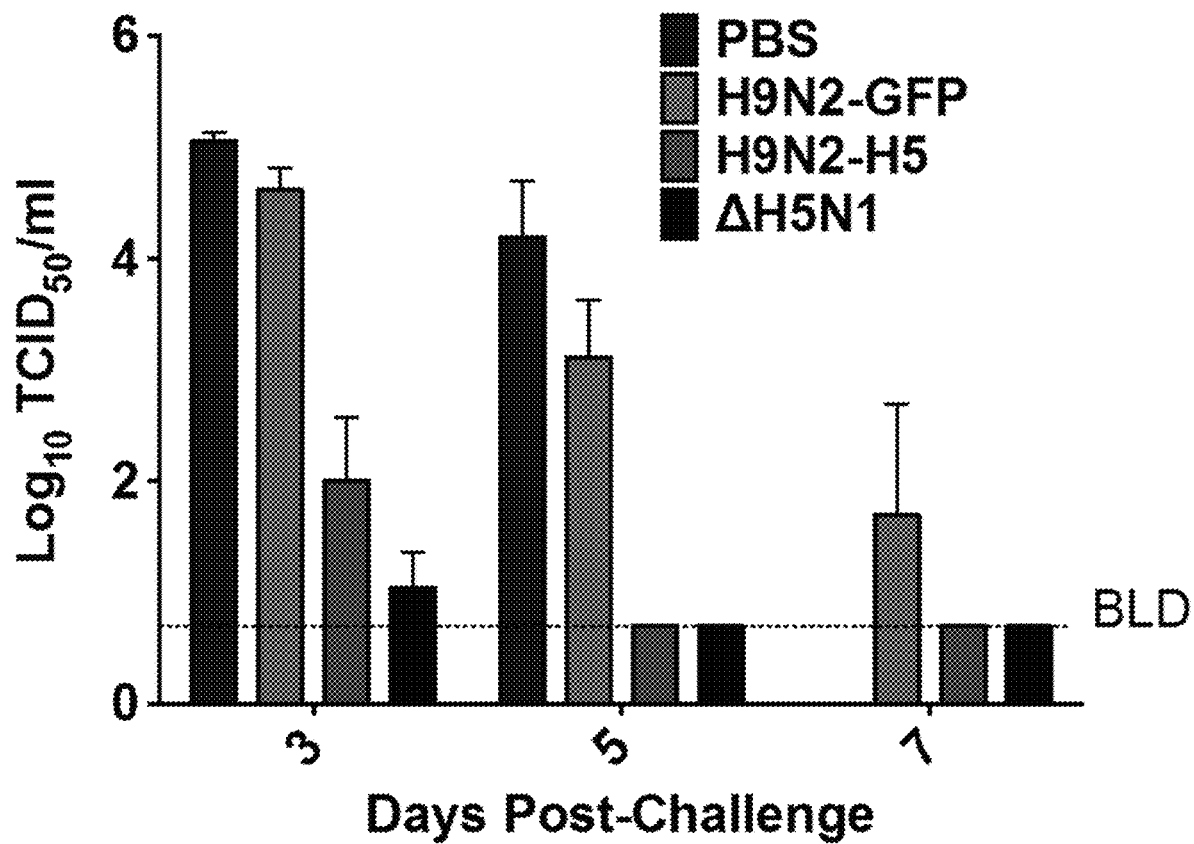

To gain more insight into the efficacy of the H9N2-H5 vector, a vaccine challenge study was conducted in ferrets, an established model of IAV (22) (FIG. 9). Ferrets were vaccinated intranasally twice on days 0 and 14 with $10^6$ EID50 of virus/animal and challenged at 2 weeks post-boost with $10^6$ EID50 of A/Vietnam/1203/2004 (H5N1). This challenge was extremely severe (equivalent to 10,000 ferret lethal dose 50%(20)) and was chosen with the objective to discriminate the protective responses induced by the H9N2-H5 vector from the cross-protection induced by the H9N2-GFP vector control. Following challenge, PBS-vaccinated animals had high levels of viral replication (FIG. 9) and all animals succumbed to infection or were euthanized by day 7 post-challenge. These animals developed severe clinical disease, which was characterized by fever, lethargy, anorexia, severe body weight loss, and diarrhea. The ΔH5N1 vaccinated ferrets did not show clinical signs of disease after challenge, although low levels virus shedding was detected in the nasal wash from one ferret on day 3 (FIG. 9). All ferrets vaccinated with the H9N2-H5 virus were completely protected against death and disease. In contrast, all of the ferrets in the H9N2-GFP group developed severe clinical infection showing weight loss, and viral shedding. Furthermore, 5 of 6 ferrets in the H9N2-GFP group succumbed to the infection. In the H9N2-GFP group, the single ferret that survived challenge shed high amounts of virus and had a maximal body weight loss of 18%. On day 3 pc, the protected H9N2-H5 ferrets had a 100-fold reduction in viral shedding compared to the ferrets in the H9N2-GFP group, and by day 5 none of the H9N2-H5 ferrets were shedding virus. Interestingly, although each ferret vaccinated with either the H9N2-H5, H9N2-GFP, or ΔH5N1 viruses showed sero conversion by ELISA against the viral NP antigen and neutralizing antibodies against H9, it was not possible to correlate protection with the levels of circulating H5 neutralizing antibodies in vaccinated animals (Tables 3 and 4 and data not shown). This finding is not unique to this vaccine study since multiple studies have shown poor humoral responses after vaccination against H5N1 using inactivated, vectored, or live attenuated vaccines (1, 7, 32, 33). Collectively, the mouse and ferrets studies indicate that the rearranged H9N2-H5 vector can elicit efficient protection against avian H5 and H9 viruses.

Table 4 shows that serum was from animals 13 days post-boost vaccination. Serum samples were treated with receptor-destroying enzyme (Accurate Chemical and Scientific Corp., Westbury, NY) to remove nonspecific receptors and the anti-viral antibody titers were evaluated using an Hemagglutination inhibition (HI) assay outlined by the WHO Manual for the laboratory diagnosis and virological surveillance of influenza (31). H9N2 wt and ΔH5N1 were used in these assays. HI titers are given as the reciprocal of the highest dilution of serum that showed activity against the corresponding virus. HI titers for each animal are shown. The limit of the detection of this technique is 10.

3. Discussion

The genome of IAV was rearranged with the goal of expanding its genome coding capacity and improving its stability. Using this strategy, rearranged IAVs carrying up to 1.7 Kb of foreign sequence (H5 ORF) were successfully rescued. Interestingly, sTable 4iruses expressing GFP and GLuc reporters were also recovered, demonstrating that both the cytosolic and secretory pathways can be accessed using this technology.

TABLE 3

NP Blocking ELISA on pre-HPAI H5N1 challenge serum shows all LAIV vaccinated animals were positive for NP antibodies. Serum was from animals 13 days post-boost vaccination. NP ELISA titers were determined using the Flu DETECT ® BE (Avian Influenza Virus Antibody Test Kit, cELISA) from Synbiotics, Co. (College Park, MD, U.S.) using manufacturer's directions. A signal to noise ratio (S/N) of less than 0.6 is considered positive for antibody against influenza.

| Group | Animal No. | NP Blocking ELISA S/N Ratio | Booth (+/−) |
|---|---|---|---|
| H9N2-GFP | 709 | 0.141 | + |
|  | 710 | 0.169 | + |
|  | 711 | 0.134 | + |
|  | 712 | 0.169 | + |
|  | 713 | 0.180 | + |
|  | 714 | 0.190 | + |
| H9N2-H5 | 715 | 0.171 | + |
|  | 716 | 0.191 | + |
|  | 718 | 0.124 | + |
|  | 719 | 0.143 | + |
|  | 720 | 0.138 | + |
| PBS | 721 | 0.651 | − |
|  | 722 | 0.646 | − |
|  | 713 | 0.727 | − |
| ΔH5N1 | 724 | 0.141 | + |
|  | 725 | 0.148 | + |
|  | 726 | 0.131 | + |

TABLE 4

H9 and H5 hemagglutination inhibition (HI) on pre-HPAI H5N1 challenge serum for LAIV vaccinated ferrets.

| Group | Animal No. | H9 HI Titer | H5 HI Titer |
|---|---|---|---|
| H9N2-GFP | 709 | 160 | <10 |
|  | 710 | 320 | <10 |
|  | 711 | 320 | <10 |
|  | 712 | 320 | <10 |
|  | 713 | 160 | <10 |
|  | 714 | 320 | <10 |
| H9N2-H5 | 715 | 80 | <10 |
|  | 716 | 40 | <10 |
|  | 718 | 80 | 10 |
|  | 719 | 80 | 10 |
|  | 720 | 160 | <10 |
| PBS | 721 | <10 | <10 |
|  | 722 | <10 | <10 |
|  | 723 | <10 | <10 |
| ΔH5N1 | 724 | <10 | 40 |
|  | 725 | <10 | 20 |

The impaired growth of the rearranged viruses could be explained mechanistically by lower polymerase activity displayed by the PB1-2A-NEP/NS2 compared to the wt PB1 gene. It was previously shown that incorporating an eight-amino-acid HA tag in the C-terminus of PB1 reduced viral replication and polymerase activity (23, 26). The 18 amino acid long FMDV 2A tag in PB1 can contribute to the attenuated polymerase activity and viral growth. Additionally, expression of NEP/NS2 from a single ORF in segment 2 can alter the levels of transcription and replication of the rearranged virus relative to their wt counterparts. NEP/NS2 has been shown to modulate the relative amounts of influenza cRNA, vRNA, and mRNA (24). Lastly, the exact boundaries of the packaging signals for IAV are not yet properly defined and can be subtype or even strain-specific. In this study, rearranged H9N2 IAV vectors were engineered respecting the length of packaging signals previously reported for H1N1 strains (18). Fine mapping of the optimum cis-acting sequences required for H9N2 vRNA incorporation into influenza virus particles can allow improvements in virus yield and stability of foreign genes.

As a proof of principle for the rearranged influenza-based vector platform, the entire H5 HA ORF was expressed in the eighth segment of rearranged H9N2 IAV vector and tested the safety and the efficacy of this vector in protection against epidemiologically relevant H5 and H9 viruses. The rearranged viruses were innocuous after administration in both mice and ferrets. And the rearrangement itself attenuated an otherwise HPAIV H5N1 virus in chickens. The H9N2-H5 vaccine proved to be very efficacious against robust challenges with HPAIV H5N1 and a transmissible avian H9:pH1N1 reassortant. Unlike LAIV that are currently licensed in the USA, which are based on a few point mutations that are not sufficient to attenuate H9N2 wt (13, 15, 27), genome rearrangement can allow a more stable attenuation phenotype since it involves more dramatic changes in the structure of the IAV genome.

In summary, IAVs are amenable to genome rearrangement and can satisfactorily accommodate large pieces of additional genetic material while preserving replication and immunogenicity. This vaccine is safe, does not require expensive high-containment manufacturing facilities and can be grown in eggs; the substrate of choice for producing IAV vaccines. Development of this technology allows for a novel class of influenza vectors that can provide immunity not only to influenza but also against other diseases.

C. Example 3: Speeding Up Influenza Vaccine Preparation: PCR-Based Reverse Genetics Strategy De novo synthesis of influenza viruses by reverse genetics (RG) requires not only the viral RNA but also the viral protein components (3, 11, 12, 14, 29). Thus, RG systems for influenza rely invariably on a dual promoter concept: one for the synthesis of vRNA segments and another for the synthesis of viral mRNAs (14). Since the termini of influenza vRNAs are crucial for virus replication, plasmids carrying a RNA polymerase I (pol1) or T7 RNA polymerase promoters have been used to generate vRNAs with the exact 3' end, whereas pol1 terminator sequence (t1) or a hepatitis δ ribozyme have been used to generate the exact 5' end. Plasmids carrying typical RNA polymerase II (pol2) promoters (CMV and/or chicken p-actin promoters) have been utilized for the synthesis of influenza mRNAs (4, 9, 16, 28, 31). Although variations to the plasmid-based approach have been developed, they inevitably rely on a cloning step (6,17).

Despite the great advantages of this technology, it proved slow during vaccine seed stock preparation for the 2009 H1N1 pandemic virus (24, 26). Thus, a system that does not rely on cloning, particularly of the surface genes, would be a major step towards speeding up influenza vaccine development. In this report, Flu PCR amplicons, instead of plasmids, are shown to be an efficient and viable alternative to the plasmid-based RG system (FIG. 10).

1. Materials and Methods
i. Viruses and Cells.

The mouse-adapted H1N1pdm virus and WF10 viruses have been previously described (23, 35). The VN1203 virus (H5N1 clade 1) was obtained from the Centers for Disease Control and Prevention, Atlanta, GA (CDC). The influenza PR8 strain was grown from a reverse genetics clone (H1N1) (PR/8). Virus stocks were prepared in specific pathogen free 9-day old embryonated chickens eggs following standard techniques for growth of influenza viruses. MDCK and Vero cells were maintained in Modified Eagle's medium (MEM) (Sigma-Aldrich, St. Louis, MO) containing 5% fetal bovine serum (FBS) (Sigma-Aldrich). Human embryonic kidney cell-line 293T (HEK293T) were cultured in Opti-MEM I (GIBCO, Grand Island, NY) containing 5% FBS.

ii. Plasmids.

The RG 8-plasmid systems for the H1N1pdm and WF10 have been previously described (30, 35). A bidirectional pGD2007 RG vector containing the canine pol1 and t1 sequences was used. The 8 gene segments of VN1203 were subcloned into the pGD2007 vector from clones originally prepared in the pDP2002 vector. The plasmids pcDNA774PB1, pcDNA762PB2, pcDNA787PA and pcDNA693NP have been previously described (18, 22). Also described is the pHW72-EGFP plasmid encoding the influenza EGFP reporter replicon (6).

iii. Preparation of Viral RNA and cDNA.

The vRNAs and cDNAs from wild type and blind passage reassortant viruses were prepared as previously described (8, 35). Briefly, total RNAs were extracted by using the RNeasy kit (Qiagen, Valencia, CA) following manufacturer's instructions. Reverse transcription was carried out with the Uni12 primer (5'-AGCAAAAGCAAGG-3'; SEQ ID NO:4) and avian myeloblastosis virus (AMV) reverse transcriptase (Promega, Madison, WI). The cDNAs were stored at −80° C. until use.

iv. PCR Strategy for Flu EGFP Replicon and Pol2-Driven P and NP Expression PCR Amplicons.

The Flu EGFP replicon was amplified with the primers pTIFragFwd and hpoHRev using pHW-EGFP plasmid DNA as the template. PCR amplicons from pcDNA762 (PB2), pcDNA774 (PB1), pcDNA787 (PA) or pcDNA693 (NP) were generated with the primers pCMVF and pBGHR, and were designated as pol2PB2bgh, pol2PB1bgh, pol2PAbgh and pol2NPbgh, respectively (6, 21, 22). The pol2-based Flu PCR amplicons were flanked by sequences corresponding to the immediate-early human cytomegalovirus (CMV) promoter and bovine growth hormone (bgh) polyadenylation signal. PCR conditions were similar to the overlapping PCR of pol1HApdmt1 and polNApdmt1 amplicons except for the use of 10 pg of the corresponding plasmid DNA template (see below).

Figure 13:
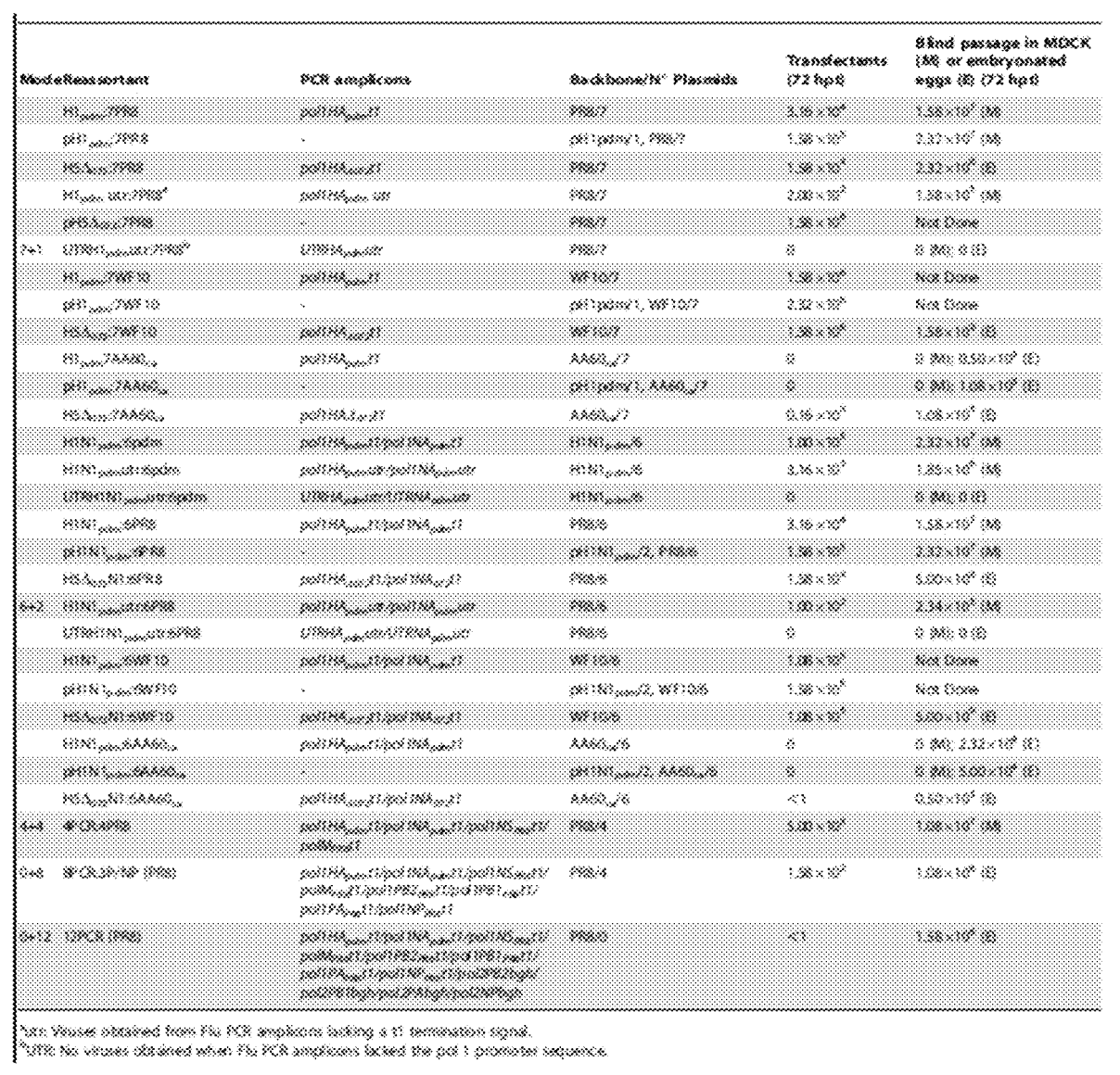

After PCR amplification, two methods were used to demonstrate that PCR products were devoid of spurious plasmid DNA contamination. PCR products were digested with Dpn I (New England Biolabs, Ipswich, MA) for 1 h, and then separated and purified by agarose gel electrophoresis, and subsequently 100 ng of the purified PCR product were used to transform *E. coli* TOP10 cells (Invitrogen, Carlsbad, CA). Alternatively, the primer pairs pCMVF and pTIFragRev, pDP2066-2090F and pDP2392-2416R, and pT1-2F and UTR-H1Rev were used to demonstrate lack of plasmid DNA contamination in purified PCR reactions (FIG. 13). This strategy was also used to demonstrate no plasmid DNA contamination after PCR amplification of the pol1 promoter from the RG vector pDP2002. In all instances, no plasmid DNA contamination was observed by either method.

v. PCR Strategy of Overlapping HA and NA Gene Segments with Human Pol1 Promoter.

Figures 14, 15:
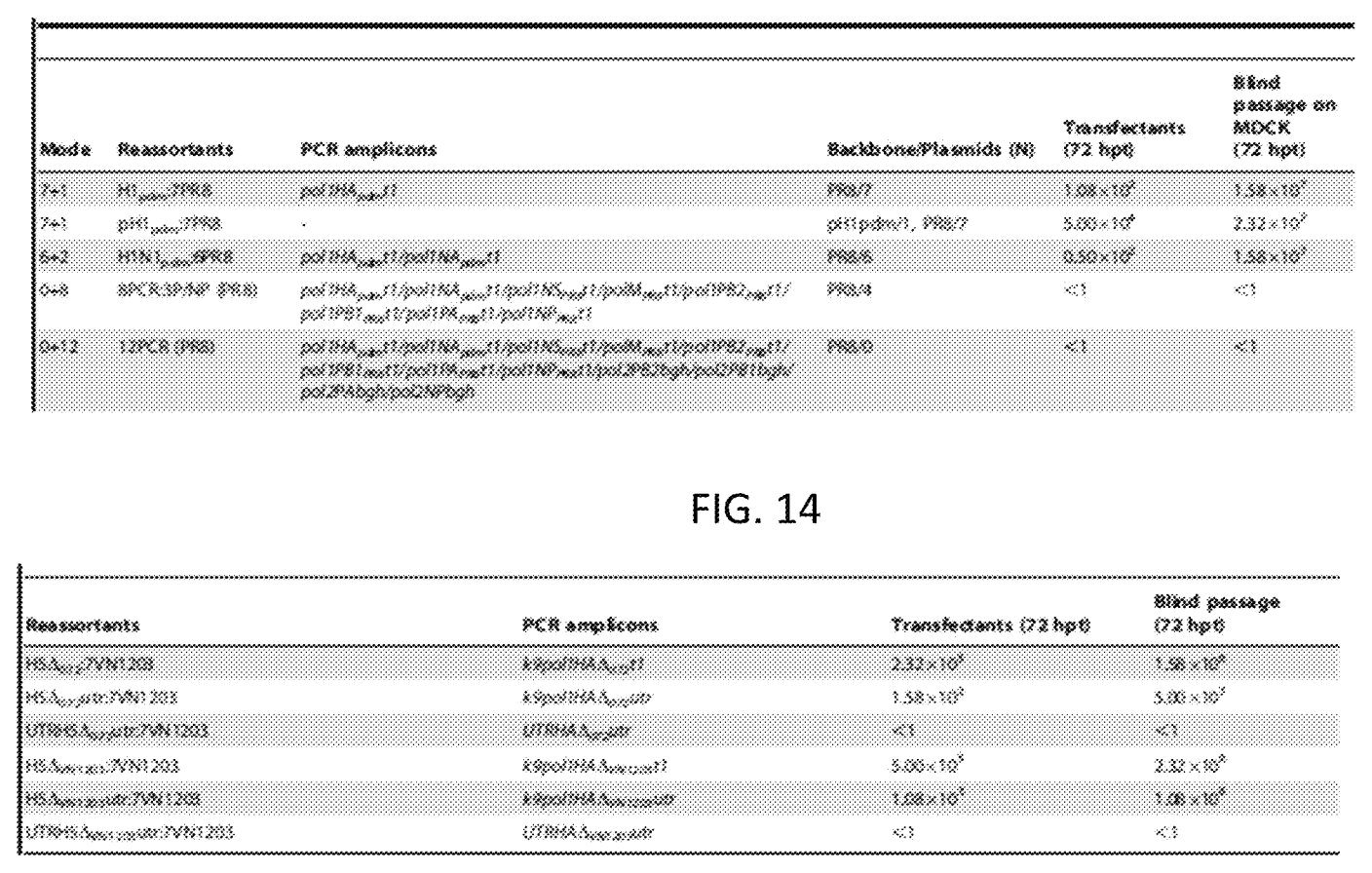

A schematic representation of the overlapping PCR approach is shown in FIG. 11 using the set of primers described in Table 2. Two overlapping PCR fragments were generated for the HApdm gene: The first fragment spans from the primer set pT1FragFwd, which incorporates the t1 signal, and SwHA-931R. The second fragment was amplified with the primer pair SwHA-752F and polFragRev. The human pol1 promoter was PCR amplified using primers polF and hPolIRev and the pDP2002 plasmid vector as template. Details of amplification conditions for each PCR fragment are provided with the supplementary information. The 3 PCR products above were purified by agarose gel electrophoresis and combined in equal proportions to generate a full-length HA PCR amplicon using the primer pair pTIFragFwd and hPol1Rev. The 50 µl PCR reaction mixture contained 10 ng of each PCR product, 25 µl of Master PCR mix, 1.5 µl 100% DMSO, and 50 pmol/µl of each primer. PCR reaction conditions were 98° C. for 30 sec, and then 30 cycles at 98° C. for 8 s, 56° C. for 1 min and 72° C. for 3 min, ending with 72° C. for 10 min. PCR products were amplified using the Phusion high-fidelity PCR master mix with GC Buffer (New England Biolabs, Ipswich, MA). Alternative HA PCR products without t1 signal sequence or lacking both pol1 and t1 elements were generated to serve as controls for PCR-based reverse genetics (FIG. 10 and FIG. 14). PCR products were purified by agarose gel electrophoresis and quantitated after gel purification using Nanodrop 1000 (Nanodrop, Wilmington, DE). Overlapping PCR products were produced for the NApdmgene using the primer pair pTIFragFwd and SwNA-763R and N1-562F and polFragRev, whereas the full length NA PCR amplicon was generated with the primer pair pTIFragFwd and hPol1Rev. Alternative full length NA amplicons were generated using specific primers as noted in FIG. 13.

TABLE 2

Primer set for production of overlapping Flu PCR amplicons

| Name* | Sequences (5'-3') |
|---|---|
| Uni12 | AGCAAAAGCAGG (SEQ ID NO: 4) |
| UTR-H1Fwd | AGCAAAAGCAGGGGATAATTGAATC (SEQ ID NO: 5) |
| UTR-H1Rev | TAGTAGAAACAAGGGTGTTTTTTCCGT (SEQ ID NO: 6) |
| hT1FragFwd | ACCGGAGTACTGGTCGACCTCCGAAGTTGGGGGGAGCAAAAGCAGG (SEQ ID NO: 7) |
| pT1HF | ACCGGAGTACTGGTCGACCTCCGAAGTTGGGGGGAGCAAAAGCAGGGG (SEQ ID NO: 8) |
| SwHA-931R | TCTGAAATGGGAGGCTGGTGTT (SEQ ID NO: 9) |
| SwHA-752F | TAGAGCCGGGAGACAAAATAACAT (SEQ ID NO: 10) |
| polHR | GTCGGCATTTTGGGCCGCCGGGTTATTATAGAAACAAGGGTGTTTT (SEQ ID NO: 11) |
| Pol1FragRev | GTCGGCATTTTGGGCCGCCGGGTTATTAGTAGAAACAAGG (SEQ ID NO: 12) |
| UTR-N1fwd | AGCAAAAGCAGGAGTTTAAAATG (SEQ ID NO: 13) |
| UTR-N1Rev | TAGTAGAAACAAGGAGTTTTTTTCA (SEQ ID NO: 14) |
| hT1N1fwd | ACCGGAGTACTGGTCGACCTCCGAAGTTGGGGGGGAGCAAAAGCAGGAGT (SEQ ID NO: 15) |
| N1-562F | CAAGTGCTTGTCATGATGGCA (SEQ ID NO: 16) |
| SwNA-763R | TTACTTGGTCCATCGGTCATTACA (SEQ ID NO: 17) |
| polN1Rev | GTCGGCATTTTGGGCCGCCGGGTTATTAGTAGAAACAAGGAGTTTTTTCA (SEQ ID NO: 18) |
| indoH5-dvF | ACAGCCCTCAAACTGAAACTAGAGGACTATTTGGAGCTATAG (SEQ ID NO: 19) |
| indoH5-dvR | TCTAGTTTCAGTTTGAGGGCTGTTTCTGAGCC (SEQ ID NO: 20) |
| polF | AATAACCCGGCGGCCCAAAATGCCGAC (SEQ ID NO: 21) |
| hPollRev | ATGCTGACAACGTCCCCGGCCCGGCGCTGCT (SEQ ID NO: 22) |
| K9pol1F | ACCTACCTGGCAACAAAAAATGTT (SEQ ID NO: 23) |
| K9pol1R | GCCTGCCTCCGGAGAACTTTG (SEQ ID NO: 24) |
| kTiUni12F | GCGGGGACAGCTGGTCGACCGGATCCACCAGGAGGGAGCAAAAGCAGG (SEQ ID NO: 25) |
| kPolUTRR | AACATTTTTGTTGCCAGGTAGGTAGTAGAAACAAGG (SEQ ID NO: 26) |
| PB2-1643F | TCAATGATGTGGGAGATTAA (SEQ ID NO: 27) |
| PB2-1811R | AACCCACTGTATIGGCCTCTAATGGC (SEQ ID NO: 28) |
| PB1-1240F | GGAATGATGATGGGCATGTT (SEQ ID NO: 29) |
| PB1-1531R | GGAAGCTCCATGCTGAAATTGGCA (SEQ ID NO: 30) |

TABLE 2-continued

Primer set for production of overlapping Flu PCR amplicons

| Name* | Sequences (5'-3') |
|---|---|
| PA-892 F | TTAAGCATTGAGGACCCAAGTCA (SEQ ID NO: 31) |
| PA-1314R | GGGTCAGTGAGAGAAAACTCCATGCT (SEQ ID NO: 32) |
| HA-760F | TGAACTATTACTGGACCTTGC (SEQ ID NO: 33) |
| HA-1274R | GTTGAATTCTTTACCCACAGC (SEQ ID NO: 34) |
| NP-1116F | GCTTTCCACTAGAGGAGTTC (SEQ ID NO: 35) |
| NP-1441R | GCTCGAAGACTCCCCGCCCCTG (SEQ ID NO: 36) |
| NA-743F | CAAGATCGAAAAGGGGAAGGTTAC (SEQ ID NO: 37) |
| NA-905R | GAACCATGCCAGTTGTCTCTGC (SEQ ID NO: 38) |
| M-741F | CCTATCAGAAACGAATGGGGG (SEQ ID NO: 39) |
| M-915R | CTCCTTCCGTAGAAGGCCCTC (SEQ ID NO: 40) |
| NS-469F | GGGCTTTCACCGAAGAGGGAG (SEQ ID NO: 41) |
| NS-887R | AGAAACAAGGGTGTTTTTTA (SEQ ID NO: 42) |
| pCMVF | AGGGCGACACGGAAATGTTGAA (SEQ ID NO: 43) |
| pBGHR | CAGACAATGCGATGCAATTTCCTC (SEQ ID NO: 44) |
| pT12F | CTAGCAGTTAACCGGAGTACTGGT (SEQ ID NO: 45) |
| hT1FragRev | CCTGCTTTTGCTCCCCCCCAACTTCGGAGGTCGACCAGTACTCCGGT (SEQ ID NO: 46) |
| pDP2066F | ATAATTCTCTTACTGTCATGCCATC (SEQ ID NO: 47) |
| pDP2416R | AACATTTCCGTGTCGCCCTTATTCC (SEQ ID NO: 48) |

*Description on the use of the primer set is found in Materials and Methods and in the Supplementary information.

Similar strategies were used to amplify the HAΔ072 and HAΔVN1203 PCR products in which the polybasic cleavage site sequence were removed using overlapping PCR products spanning sequences from the primer pairs pTIFragFwd and IndoH5-clvR and IndoH5-clvF and polFragRev whereas the full length HA PCR amplicon as generated with the primer set pTIFragFwd and hPollRev. The full length NA gene segment from Indo072 strain was amplified without the generation of internal overlapping fragments using the primer set hTIN1Fwd and polN1Rev rather and then subsequently introduced in a PCR reaction to generate the full-length pol1NA072t1 PCR amplicon carrying the poll promoter (Table 2).

vi. Overlapping PCR for the Internal Gene Segments of PR8.

To set up a reverse genetics system completely using the full PCR amplicons, H1N1pdm surface genes and PR8 virus backbone to provide the 6 internal genes were selected. Here, the internal genes were amplified from the total cDNAs prepared by a PR8 wildtype strain, which has a high titer to $1.58 \times 10^9$ TCID50/mL in MDCK cells after a limited amplification in embryonated eggs.

For overlapping PR8 PB2 with poll and t1 signal, pTIFragFwd and PB2-1811R primers were used to get the N terminal fragment of PB2 (PB2-N), and then used PB2-1643F and polFragRev primers to get the C terminal fragment (PB2-C). Mixed with PB2-N, PB2-C and poll fragments, and the overlapping PCR reaction was driven by the forward primer pTIFragFwd and the reverse primer hPoM Rev. The PCR parameters were similar to those of pol1HApdmt1 and pol1NApdmt1 amplicons described above. The final product is termed as pol1PB2PR8t1. It is similar to all the other segments fused with poll and t1 signal sequence, the internal forward/reverse primers were changed to: PB1-1240F/PB1-1531R, PA-892F/PA-1314R, HA-760F/HA-1274R, NP-1116F/NP-1441R, NA-743F/NA-905R, M-741F/M-915R, or NS-469F/NS-887R primers respectively, which was also described in the context. And the final products were designated as pol1PB1PRat1, pol1PAPRBt1, pol1HAPRat1, pol1NPPR8t1, pol1NAPR8t1, po1MPR8t1, and pol1NSPR8t1, respectively.

vii. Overlapping PCR with Canine Poll Promoter

The generation of the HA PCR amplicon from H5N1 containing the k9poll promoter was performed as follows: The k9poll promoter was amplified from the pGD2007 vector using the primer pair k9pol1F and k9pol1R under these conditions: the initial denaturation at 98° C. for 30 sec, 30 cycles of 98° C. for 8 sec, 60° C. for 30 sec, and 72° C. for 1 min and the final extension at 72° C. for 10 min (Table 2). Overlapping HA fragments, one containing the k9t1 signal was produced with the primer pair kTIUni12F and IndoH5-clvR (H5N1) and the second one with the primer pair IndoH5-clvF (H5N1) and kPolUTRR under the following conditions: pre-PCR treatment at 98° C. for 30 sec, 30 cycles of 98° C. for 8 sec, 56° C. for 30 sec, and 72° C. for 1 min and the final extension at 72° C. for 10 min (Table 2). The overlapping HA PCR products and the k9pol1 amplicon were calculated to be mixed together at a concentration of 10 ng each. A full length HA PCR amplicon was generated with the primer pair k9TIUni12F and k9Pol1R. The thermal profile was: denaturation at 98° C. for 30 sec, 30 cycles of 98° C. for 8 sec, 56° C. for 1 min, and 72° C. for 4 min, and then extension at 72° C. for 10 min. All the PCR products were amplified using the Phusion high-fidelity PCR master mix with GC Buffer.

viii. Generation of Virus by Reverse Genetics Using PCR Amplicons

For partial plasmid-free rescue, the plasmid of choice was replaced with the corresponding Flu PCR amplicon and virus rescue performed essentially as described (7) with minor modifications. Briefly, co-cultured 293T/MDCK cells at a ratio of 500:1 ($5 \times 10^5$ cells per well) was seeded into each well of a 6-well tissue culture plate. The plates were incubated at 37° C. overnight. The following day, 1 ug of each plasmid or Flu PCR amplicons was incubated for 45 min with 16 µl of Transit-L1 transfection reagent (Mirus Bio LLC, Madison, WI) and then the transfection allowed to occur overnight before the media was replaced with fresh serum-free Opti-MEM. At 24 hpt, L-(tosylamido-2-phenyl) ethyl chloromethyl ketone (TPCK)-treated trypsin (1 µg/ml) was added to the cell supernatants.

MDCK and Vero cells were grown to 70% confluency in 75-cm2 flasks and then trypsinized with trypsin-EDTA (Invitrogen) and resuspended in Opti-MEM I containing 5% FBS. Cell suspensions were seeded into 6-well tissue culture plates and incubated at 37° C. overnight before transfection. Transfections and post-transfection steps proceeded as described for the 293-T/MDCK co-cultured cells, except that Vero cells were incubated with 2 µg/ml of TPCK-trypsin.

Supernatant of transfected cells were collected at the times indicated in FIGS. 13-15 and blind passage in either or both MDCK cells or 10-day old embryonated chicken eggs to monitor for the presence of rescued viruses. TCID50 titers were determined in MDCK cells by the Reed and Muench method as described (25). Virus stocks were prepared and frozen at −80° C. until use.

ix. Sequence Analysis

Sequencing of PCR products and viral cDNAs was performed using a combination of universal primers (8) and custom made primers (available upon request) and the Big Dye Terminator v3.1 Cycle Sequencing kit (Applied Biosystems, Foster City, CA) on a 3500 Genetic Analyzer (Applied Biosystems, Foster City, CA) according to the manufacturer's instructions. Sequence analysis was performed using software available through the Lasergene package (DNAstar Inc., Madison, WI)

x. Immunofluorescence Assay

Cells grown in 96-well plates were infected with rescued influenza viruses at a dose of 1 TCID50/well. At 36 hpi, the cells were washed in precooled 0.01 M Phosphate Buffered Saline (PBS) buffer and fixed in neutral formaldehyde for 20 min at room temperature. The cells were then incubated with blocking solution (10% normal goat serum in PBS) for 1 h and probed with a primary antibody for 30 min. Two monoclonal antibodies were used to identify the recombinant influenza viruses: mAb 3B2 is specific for the HA protein of H1N1pdm viruses and which does not react with the HA of PR8 and other subtypes of influenza A viruses (27). mAb DPJY01 is specific for the HA of H5 subtype influenza viruses (34). The antibody-antigen complexes were further incubated with fluorescein isothiocyanate (FITC)-conjugated goat anti-mouse Ig (H+L) (Southernwest Biotech Associates Inc, Birmingham, AL) for 30 min at room temperature. The cells were washed three times with PBS after incubation and then counterstained with propidium iodide (PI) and examined under an Axiophot Photomicroscope produced by Carl Zeiss (AEx of 488/543 nm, AEm of 522/590 nm for 100 ms).

xi. Pol1- and Pol2-Driven PCR Amplicons.

Generation of Flu EGFP replicons from pHW72EGFP was performed. Lane 1, poUEGFPtl amplicon amplified with the primer pair pTIFragFwd hpoMRev. The Flu EGFP amplicon (1103 bp) contained the Flu EGFP replicon (846 bp) flanked by the human pol1 (222 bp) and mouse t1 (35 bp) sequences. Lane 2, poMEGFPutr amplicon (1068 bp, lacking the t1 sequence) produced with the primer pair Bm-M-1F and hpoMRev. Lane 3, UTREGFPutr amplicon (846 bp, lacking the pol1 and t1 sequences) amplified with the primers Bm-M-1 F and Bm-M-1043R. Lane 4, UTREGFPtl amplicon (881 bp, lacking pol1 sequence) generated with the primers pTIFragFwd and poUFragRev. B) Pol2 Flu PCR amplicons produced from pcDNA762 (PB2), pcDNA774 (PB1), pcDNA787 (PA) and pcDNA693 (NP), respectively using the primer pair pCMVF and pBGHR. Each pol2 Flu PCR amplicon contained the cytomegalovirus immediate early promoter sequence (CMV, 659 bp), the bovine growth hormone polyA signal (BGHpA, 228 bp) and additional non coding regions present within the multiple cloning site of pcDNA3 (Invitrogen). Lane 1, pol2PB2bgh (3,386 bp); lane 2, pol2PB1bgh (3,385 bp); lane 3, pol2PAbgh (3,271 bp); and lane 4 pol2NPbgh (2,603 bp). "M" in panels A and B corresponds to DNA molecular weight marker (GeneRuler™ 1 kb Plus DNA Ladder, Fermentas).

xii. Generation of HA and NA Amplicons.

cDNAs from the H1N1pdm and H5N1 072 viruses were prepared as described in the main text. M, 1 kb plus DNA molecular weight marker. Lane 1, unspecific PCR products obtained using one-step RT-PCR to generate the full length of HApdm gene (1,840 bp) with the primers pT1HF and polHR. Lane 2, the N terminus of HApdm specific PCR product (998 bp) obtained using the primer pair pTIFragFwd, which incorporates the t1 signal, and SwHA-931 R. Lane 3, the C terminus of overlapping HApdm specific PCR product (1,022 bp) using the primer pair SwHA-752F and polFragRev. Lane 4, the N terminus of NApdm specific PCR product (799 bp) obtained using the primer pair pTIFragFwd and SwNA-763R. Lane 5, the C terminus of NApdm specific PCR product (924 bp) from N1-562F and polFragRev primer set. Lane 6, the first HAΔ072 specific PCR fragment (1,090 bp) obtained with the primers pTIFragFwd and IndoH5-clvR. Lane 7, the second HAΔ072 specific PCR fragment (762 bp) obtained with the primers pair IndoH5-clvF and poUFragRev. Lane 8, the full-length NAΔ072 amplicon (1,460 bp) generated with the primer set hTIN1Fwd and polN1Rev. The 25 µl PCR reaction mixture contained 10 ng of cDNAs, 12.5 µl of Master PCR mix, 0.6 µl 100% DMSO, and 10 pmol/µl of each primer. The PCR reaction conditions were 98° C. for 30 sec, and then 30 cycles at 98° C. for 8 s, 56° C. for 1 sec and 72° C. for 2 min, ending with 72° C. for 10 min. PCR products were amplified using the Phusion high-fidelity PCR master mix with GC Buffer.

xiii. Full-Length PCR Amplicons from PR8 Virus Gene Segments.

A) The PR8 virus gene segments were amplified as two overlapping PCR fragments, which were performed as follows: Lane 1, amplification of the N terminal fragment of PB2PR8 (1,846 bp) with primer pair pTIFragFwd and PB2-1811R. Lane 2, amplification of the C terminal fragment of PB2PR8 (741 bp, yellow arrow) with primer pair PB2-1643F and polFragRev. Lane 3, amplification of the N terminal fragment of PB1PR8 (1,566 bp) with primer pair pTIFragFwd and PB1-1531R. Lane 4, amplification of the C terminal fragment of PB1PR8 (1,128 bp) with primer pair PB1-1240F and polFragRev. Lane 5, amplification of the N terminal fragment of PAPR8 (1,349 bp) with primer pair pTIFragFwd and PA-1314R. Lane 6, amplification of the C terminal fragment of PAPR8 (1,368 bp) with primer pair PA-892F and polFragRev. Lane 7, amplification of the N terminal fragment of HAPR8 (1,309 bp) with primer pair pTIFragFwd and HA1274R. Lane 8, amplification of the C terminal fragment of HAPR8 (1,042 bp) with primer pair HA-760F and polFragRev. Lane 9, amplification of the N terminal fragment of NP (1,476 bp, yellow arrow) with primer pair pTIFragFwd and NP-1441R. Lane 10, amplification of the C terminal fragment of NP (476 bp) with primer pair NP-1116F and polFragRev. Lane 11, amplification of the N terminal fragment of NAPR8 (940 bp) with primer pair pTIFragFwd and NA 905R. Lane 12, amplification of the C terminal fragment of NAPR8 (697 bp) with primer pair NA 743F and polFragRev. Lane 13, amplification of the N terminal fragment of MPR8 (950 bp) with primer pair pTIFragFwd and M-915R. Lane 14, amplification of the C terminal fragment of MPR8 (313 bp) with primer pair M-741F and polFragRev. Lane 15, amplification of the N terminal fragment of NSPR8 (923 bp) with primer pair pTIFragFwd and NS-887R. Lane 16 amplification of the C terminal fragment of NSPR8 (468 bp) with primer pair NS-469F and polFragRev. PCR conditions were similar to those described in FIG. 2. B) Overlapping PCR products generated in A) were mixed at a concentration of 10 ng (each product) and amplified with the forward primer pTIFragFwd and the reverse primer hPol1Rev as described in the main text. The thermal profile was: denaturation at 98° C. for 30 sec, 30 cycles of 98° C. for 8 sec, 56° C. for 2 min, and 72° C. for 4 min, and then extension at 72° C. for 10 min. All the PCR products were amplified using the Phusion high-fidelity PCR master mix with GC Buffer. The final overlapping PCR amplicons were designated as pol1PB2PR8t1 (2,598 bp, lane 1), pol1PAPR8t1 (2,490 bp, lane 2), pol1NPPR8t1 (1,822 bp, lane 3), pol1NAPR8t1 (1,670 bp, lane 4), po1MPR8t1 (1,284 bp, lane 5), and pol1NSPR8t1 (1,147 bp, lane 6), pol1PB1PR8t1 (2,598 bp, lane 7), and pol1HAPR8t1 (2,032 bp, lane 8). M, 1 kb plus DNA molecular weight marker.

xiv. HA PCR Amplicons Flanked with k9pol1 Promoter.

Two produce overlapping PCR products for HAΔ072 and HAΔVN1203 gene segments. PCR conditions used were similar to those described in FIG. 2 and in the main text. Lane 1, the k9pol1 promoter (351 bp) was amplified from the pGD2007 vector using the primer pair k9pol1F and k9pol1R. Lane 2, PCR fragment containing the N-terminus of HAΔ072 and the k9t1 signal (36 bp) was produced with the primer pair kTIUni12F and lndoH5-clvR with a size of 1,091 bp. Lane 3, PCR fragment containing the C-terminus of HAΔ072 (760 bp) produced with the primer pair lndoH5-clvF and kPolUTRR. Lane 4, PCR fragment containing the N-terminus of HAΔVN1203 (1,091 bp) amplified as in lane 2. Lane 5 PCR fragment containing the C-terminus of HAΔVN1203 (760 bp) produced as in lane 3. Lane 6, the two overlapping HAΔ072 PCR products and the k9pol1 PCR fragment were mixed at a concentration of 10 ng (each product) to generate the full length of k9pol1 HAΔ072t1 PCR amplicon (2,144 bp) using the primer pair kTIUni12F and k9pol1R. Lane 7, the two overlapping HAΔVN1203 PCR products and the k9pol1 PCR fragment were mixed at a concentration of 10 ng each and amplified to generate the full length k9pol1HAΔVN1203t1 amplicon (2,144 bp) using the primer pair kTIUni12F and k9pol1R. Lane 8, same as in lane 6, except that k9pol1HAΔ072utr (2, 109 bp) lacks the k9t1 signal after amplification with the primer pair Bm-HA-1F and k9pol1R. Lane 9, same as in lane 7, except that k9pol1HAΔVN1203utr (2,109 bp) lacks the k9t1 signal after amplification. M, 1 kb plus DNA molecular weight marker.

2. Results i. A Flu Reporter PCR Amplicon Results in Reporter Activity

Figures 10A, 10B:
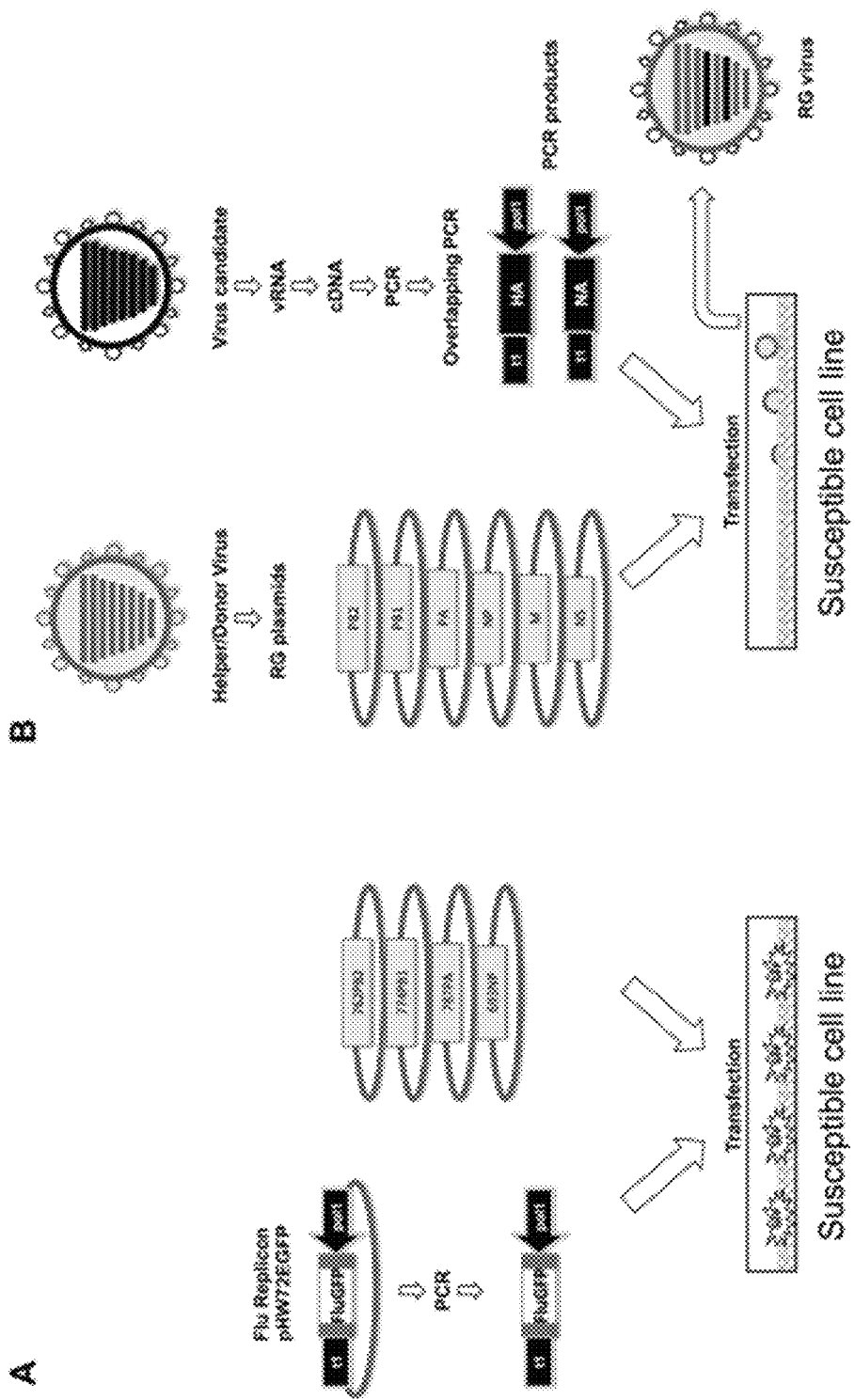
FIGS. 10A and 10B show PCR-based reverse genetics. A) PCR-based Flu reporter replicon encoding GFP: PCR amplification was performed using primers spanning the pol1 to t1 sequences and pHW72EGFP. After agarose gel purification and testing to show that the PCR product is devoid of plasmid DNA contamination, the Flu GFP amplicon is transfected into 293T cells along with four expression plasmids encoding the polymerase complex of influenza virus. Expression of GFP reflects influenza polymerase activity on a vRNA Flu GFP replicon generated from pol1 transcription of the Flu GFP amplicon. Variations to this these are described in the main text. B) Starting with a influenza virus candidate, vRNA, cDNA and reconstitution of a full-length Flu PCR amplicon (in this case, the HA and NA PCR amplicons are depicted) is performed. Transfection of Flu PCR amplicons along with appropriate complementary RG plasmids into susceptible cells leads to the generation of recombinant influenza viruses with the desired gene constellation. The strategy speeds up the reverse genetics process by obviating a classical cloning step, which is currently part of the plasmid-based RG system.

Flu GFP PCR amplicons were derived from pHW72-EGFP (6). In order to determine whether a Flu PCR amplicon could be transfected into cells and be amplified by the influenza polymerase complex, a PCR product encoding the GFP reporter gene in negative orientation flanked by the influenza segment 7 untranslated regions (UTRs) and further flanked by the human pol1 promoter and the mouse t1 signal, pol1EGFPt1 was produced (FIG. 10A, Table 2). Co-transfection of the pol1lEGFPH amplicon along with 4 protein expression plasmids encoding the influenza virus polymerase complex (3P) and NP into 293T cells resulted in efficient amplification of the reporter replicon and detection of green fluorescence signal. The proportion of green cells observed was comparable to those observed in the positive control cells co-transfected with pHW72-EGFP and the 3P and NP expression plasmids. The fluorescence signal of another amplicon, pol1EGFPutr, which lacks the t1 signal, was present in fewer cells compared to the pol1EGFPT1 amplicon indicating that run off transcription by the RNA poll complex can result in vRNA fragments with incorrect and/or incomplete influenza sequences. As expected, no fluorescence signal appeared when cells were transfected with a Flu GFP PCR amplicon lacking the poll and t1 elements (UTREGFPutr) or by removing the PB1 plasmid in co-transfected cells with either PCR amplicons or pHW72-EGFP plasmid.

The studies were expanded in order to test whether PCR amplicons containing RNA polymerase II (pol2) and poly-adenylation sequences flanking an appropriate ORF would result in gene expression. Thus, the 3P and NP genes were PCR amplified using a set of primers spanning the cytomegalovirus promoter (CMV) and bovine growth hormone (bgh) polyA elements. Co-transfection of the pol2PB2bgh, pol2PB1bgh, pol2PAbgh, and pol2NPbgh, along with pHW72-EGFP, resulted in efficient reporter replicon expression indicating that PCR amplicons with either pol1 or pol2 transcription elements are appropriately transcribed by the corresponding transcription complexes.

ii. Generation of Flu PCR Amplicons by Overlapping PCR

Figures 11A, 11B, 11C, 11D:
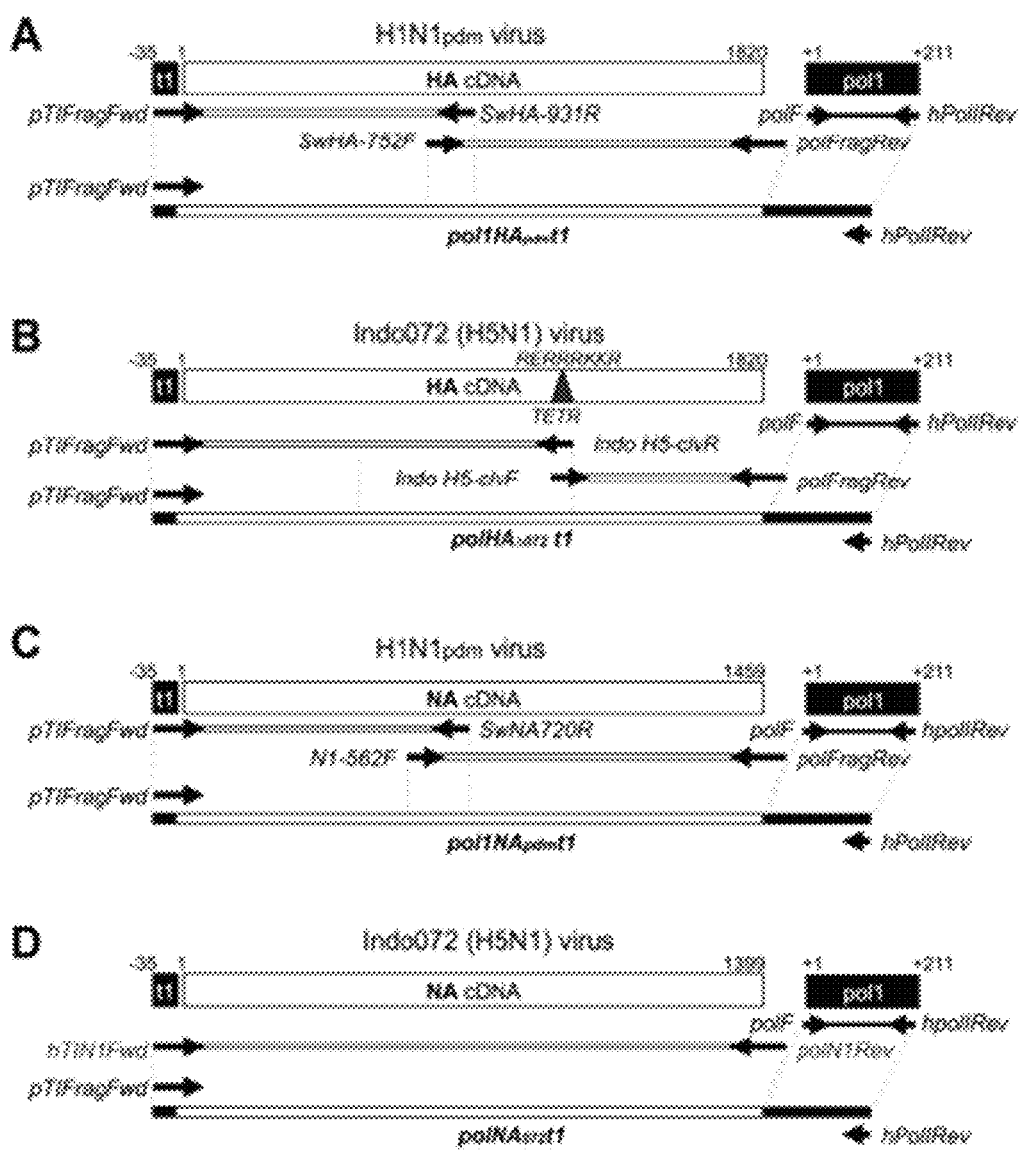
FIGS. 11A-11D show the overlapping PCR strategy and reconstitution of HA and NA PCR amplicons. The strategy to produce full-length HA and NA PCR amplicons was based on amplification of the pol1 promoter from the pDP2002 vector, subtype specific internal primers for HA and NA and, depending on the product, primers containing a t1 termination signal. A) The HApdm was amplified with the following overlapping fragments: 1, fragment spanning the primer set pT1FragFwd and SwHA-931R (which incorporates the t1 signal), 2, fragment spanning from the SwHA-752F and polFragRev, and 3, pol1 promoter fragment amplified using polF and hPol1Rev primers. The three PCR products above were purified by agarose gel electrophoresis and combined in equal proportions (10 ng each) to create the full length pol1HApdmt1 PCR amplicon using the primer pair pT1FragFwd and hPol1Rev. B) An overlapping PCR strategy to produce an H5 HA segment in which the polybasic cleavage site from the chicken/North Sumatra strain was removed and replaced by the sequence of low pathogenic virus following the strategy described above. C) and D) Depict the strategies used for generation of full length N1 PCR products from the H1N1pdm and 072 H5N1 strains.

In order to demonstrate whether Flu PCR amplicons could be used to replace plasmids in the RG system, the strains mouse-adapted A/California/04/2009 (H1N1) (35) and A/chicken/North Sumatra/072/2010 (H5N1)—herein referred to as H1N1pdm and 072, respectively—were used as donors for the HA and NA genes (FIG. 10B and FIG. 11). A specific set of internal primers designed within conserved regions of these gene segments were then developed in order to maximize gene amplification from viral cDNA preparations and to assemble the appropriate HA and NA PCR amplicons (FIG. 11). The pol1HApdmt1 PCR amplicon carried a full-length copy of the HA gene from the H1N1pdm strain flanked by the poll and t1 signals. With respect to the 072 HA gene, the internal primers were designed to delete (A) the polybasic amino acid signal sequence (RERRKRRR; SEQ ID NO:49) and replace it with one carrying a monobasic cleavage site (TETR) (FIG. 11B). Similar strategies were followed to create the NA amplicons pol1NApdmt1 and polNA072t1 from viral cDNAs (FIGS. 11C and D). Full-length pol1HApdmt1 and pol1NApdm1 PCR amplicons were obtained and confirmed by sequencing results. In addition, full-length HA and NA PCR amplicons lacking either the t1 sequence or both the poll and t1 sequences were generated, which serve as controls for efficiency of virus rescue as described below. Sequencing results confirmed the amplification of an overlapping ΔH5 HA amplicon, pol1HAΔ072T1, with a deleted polybasic cleavage site and the full-length amplification of the polNA072t1.

iii. Efficient Influenza Virus Rescue Using Flu PCR Amplicons in Either "1+7" or "2+6" Modes.

Figure 12:
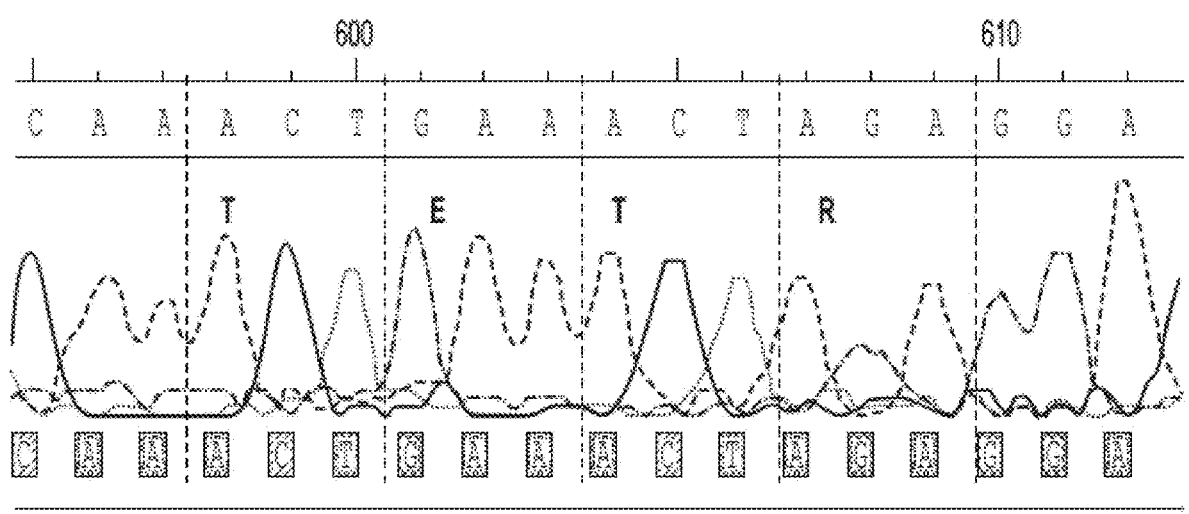
FIG. 12 shows the sequence of HA cleavage site of H5D072N1:6PR8 virus indicates the presence of a low pathogenic pattern (TETR), which was created by overlapping PCR as indicated in the materials and methods and FIG. 11B.

The pol1HApdmt1 or pol1HAΔ072t1 HA PCR amplicons (FIG. 13) were co-transfected into co-cultured 293T/MDCK cells in a "1+7" mode along with 7 RG plasmids encoding the corresponding additional gene segments from the influenza A/Puerto Rico/8/1934 (H1N1) strain (PR8). At 48 h and 72 h post-transfection (hpt) cells co-transfected with the pol1HApdmt1 PCR amplicon plus 7 RG PR8 plasmids (H1pdm:7PR8) showed typical virus-induced cytopathic effect (CPE). H1pdm:7PR8 virus titers at 72 hpt reached $3.16 \times 10^4$ TCID50/ml, which was 5 times lower than the one obtained using the corresponding pH1pdm RG plasmid (pH1pdm:7PR8, $1.58 \times 10^5$ TCID50/ml) (FIG. 13). After a subsequent blind passage in MDCK cells or 9 day-old embryonated chicken eggs, virus titers increased >$10^7$ TCID50/ml with either the pol1HApdmt1 PCR amplicon or the whole plasmid-based RG system. Likewise, the ΔH5N1 virus could be rescued using the pol1HAΔ072t1 HA PCR amplicon and 7 RG PR8 plasmids (H5Δ072:7PR8, Table 1). At 72 hpt, H5Δ072PCR:7PR8 virus titer in transfected cells was $1.58 \times 10^4$ TCID50/ml, and increased to $2.32 \times 10^8$ TCID50/ml when passaged in eggs (FIG. 13). The identity of the 1+7 reassortants was further confirmed by sequencing and immunofluorescence assay (IFA) (FIG. 12). As expected, no CPE and no virus was detected after transfection of cells with 7 RG PR8 plasmids and in which the plasmid encoding the HA segment was omitted.

Because the PR8 virus is a fully laboratory adapted strain and can be recovered very efficiently by RG, whether the pol1HApdmt1 or pol1HAΔ072t1 PCR amplicons could be recovered in the background of other RG systems including the A/guinea fowl/Hong Kong/WF10/1999 (H9N2) (23) and the cold-adapted A/Ann Arbor/6/1960 (H2N2) (13) strains, herein referred to as WF10 and AA60ca, respectively were tested (FIG. 13). In addition, virus rescue was performed in the context of the H1N1pdm background (FIG. 13). Regardless of the RG virus background used, virus rescued was possible. This was particularly the case using the WF10 background in which high virus titers ($1.58 \times 10^6$ TCID50/ml) in the initial co-transfected cells were obtained with either pol1HApdmt1 or pol1HAΔ072t1 HA PCR amplicons (H1pdmPCR:7WF10 and H5Δ072PCR:7WF10, respectively, FIG. 13). When passaged into eggs, virus titers increased significantly, about 1,000 fold for the H5Δ072PCR:7WF10 virus. Virus titers below or just at the limit of detection were observed in cells co-transfected in the context of 7 RG plasmids from the AA60ca strain carrying either the pol1HApdmt1 (H1pdmPCR:7AA60ca) or pol1HAΔ072t1 (H5Δ072PCR:AA60ca) HA PCR amplicons or the control plasmid pH1pdm (pH1pdm:7AA60ca). However, a >1,000 fold increase in virus titers were observed after blind passage in eggs of supernatants of the AA60ca-based co-transfected cells from these reassortant groups (FIG. 13).

In the 2+6 mode, efficient virus rescue was also obtained. No statistical differences were observed in rescue efficiency between the Flu HA PCR amplicon plus 7 PR8 RG plasmids (H1pdm:7PR8) compared to the HA and NA amplicons and 6 PR8 RG plasmids (H1N1pdm:6PR8). If the WF10 background was used, co-transfection of the HA and NA amplicons resulted in approximately 10 fold less virus (H1N1pdm:6WF10) in the supernatant of transfected cells compared to using the HA amplicon alone (HApdm:7WF10). A similar trend was observed when the AA60ca background was used (compare reassortants H1N1pdm:6AA60ca with HApdm:7AA60ca). ΔH5N1 viruses could also be rescued from the 072 strain using the amplicons pol1HAΔ072t1 and pol1NA072t1 co-transfected with either the PR8, WF10, or AA60ca backgrounds with efficiencies similar to those obtained using the HA and NA amplicons from the H1N1pdm strain. It must be noted that reassortant viruses carrying 7 gene segments from either WF10 or AA60ca encode a N2 NA subtype, which may have affected the rescue efficiency of the H1pdm or ΔH5 HA gene segments. Nevertheless, the results showed that either the 1+7 or 2+6 strategies using Flu PCR amplicons is a suitable method to speed up the recovery of influenza viruses by RG.

iv. Low Efficiency of Virus Rescue Using Flu PCR Amplicons Lacking the t1 Signal.

Since the PCR strategy was initially developed with pol1 and t1 signals, whether amplicons lacking the t1 signal could be better substrates for the generation and subsequent amplification of vRNA segments was determined. PCR amplicons were prepared and designated as pol1HApdmutr or pol1NApdmutr using the overlapping PCR method mentioned above, and in which the t1 signal was omitted. Similarly, PCR amplicons for HA and NA lacking both the poll and t1 signals were prepared and used as controls. Using either the PR8 or H1N1pdm virus backgrounds, virus rescue was possible with HA and NA PCR amplicons lacking the t1 signal, although the rescue efficiency was 100~200 fold lower than using the same amplicon with the t1 signal. After passage in MDCK cells, virus titers of these reassortants (HApmdutr:7PR8, HAPdmUtr:7pdm, H1N1pdmutr:6PR8, and H1N1pdmutr:7pdm) were increased although they were 10-30 fold lower than those obtained with the full-length t1 signal-containing amplicons (HApmd:7PR8, HApdm:7pdm, H1N1pdm:6PR8, and H1N1pdm:7pdm, FIG. 13). These results are consistent with previous observations using the Flu GFP amplicon lacking the t1 signal, which indicates that the presence of the t1 signal helps generate optimal full-length Flu PCR amplicons v. Plasmid-Free Reverse Genetics Using PCR Amplicons.

The use of PCR amplicons was expanded to a suitable surrogate system to recover influenza viruses without the use of plasmids. Thus, each virus segment was amplified to generate a full set of Flu PCR amplicons encoding each one of the viral segments (data provided in Chen et al. PLOS ONE vol 7, issue 9, September 2012, which is incorporated by reference herein). The optimal cocktail of eight PCR amplicons, based on the HA and NA genes of the H1N1pdm and 6 other amplicons from the PR8 strain, consisted of polPB1PR8t1 (1 µg), polPB2PR8t1 (1 µg), polPAPR8t1 (1 µg), polNPPR8t1 (1 µg), polHApdmt1 (0.5 µg), polNApdmt1 (0.5 µg), polMPR8t1 (0.5 µg), and polNSPR8t1 (0.3 µg), along with the 3P (1 µg each) and NP (1 µg) expression helper plasmids. The mixture was transfected into co-cultured 293T/MDCK cells with a ratio of 500/1 and at a density of 5×105 cells. It resulted in low efficiency virus rescue with a titer of 1.58×102 TCID50 after 72 hpt with no detectable HA titer (FIG. 13, 8PCR:3P/NP (PR8) virus). Blind passage in MDCK cells, resulted in virus titers in the order of 1×106 TCID50/ml with an HA titer of 128. These studies were further expanded to include a full set of PCR products in which the 3P and NP expression plasmids were replaced by the corresponding pol2PB2bgh, pol2PB1bgh, pol2PAbgh, and pol2NPbgh amplicons in a reaction including 12 PCR amplicons and no plasmids (Table 2, 12PCR (PR8) virus). Here again virus rescue was possible albeit at reduced levels and only detected after blind passage in MDCK cells. Variations to this theme in which 4 PCR amplicons were used to replace the corresponding plasmids (FIG. 13, 4PCR:4PR8 virus), resulted also in efficient virus rescue indicating that the PCR-based strategy is not limited to just the viral surface genes and it could be easily applied to other gene segments that can be reluctant to cloning.

vi. Virus Rescue by PCR Amplicons in Vero and MDCK Cells.

Because Vero and MDCK cells have been approved for influenza vaccine production, whether Flu PCR amplicon rescue, either in 1+7 or 2+6 modes, was possible in these cells was investigated. Vero cells co-transfected with the Flu HA (alone or in combination with the NA) PCR amplicon from the H1N1pdm strains and 7 (or 6) PR8 RG plasmids resulted in virus rescue that was observed at 120 hpt (~$10^2$ TCID50/ml) with about 500 fold lower efficiency compared to the whole plasmid-based system (FIG. 14). Blind passage of supernatants of Vero cells at 72 hpt into MDCK cells resulted in virus titers similar to those obtained using the whole plasmid RG system (around $10^7$ TCID50/ml).

Using the 1+7 approach, virus rescue was also possible in MDCK cells with HA PCR amplicons from two H5N1 strains, 072 and A/Viet Nam/1203/2004 (VN1203) (FIG. 15). In this case, HA PCR amplicons were prepared carrying the canine poll promoter (k9pol1) and termination signals (k9t1). Both HA genes were amplified using overlapping PCRs that removed the gene's polybasic cleavage site sequences. Co-transfections of the HA PCR amplicons and 7 k9pol1-driven RG plasmids from the VN1203 strain in MDCK cells resulted in virus rescue with titers of ~105 TCID50/ml at 120 hpt and 108 TCID50/ml after blind passage in MDCK cells (FIG. 15, reassortant viruses HAΔ072:7VN1203 and HAΔVN1203:7VN1203). Like in the previous transfection studies, removing the k9t1 signal from the PCR products resulted in impaired virus rescue (reassortant viruses HAΔ072utr:7VN1203 and HAΔVN1203utr:7VN1203), and removing both the k9pol1 and k9t1 sequences resulted in no virus rescue.

3. Discussion

In this report, a significant modification was introduced to the plasmid-based reverse genetics system (5, 7, 19) for influenza based on PCR amplicons. In order to optimize and maximize amplification of the genes of interest, a strategy involving overlapping PCR fragments for each segment was designed and used in conjunction with a high fidelity polymerase and corresponding buffer, Phusion high-fidelity PCR master mix with GC Buffer (New England Biolabs). This enzyme performed the best, compared to seven other commercially available DNA polymerases (Supplementary materials and methods), The synthesis of full length Flu PCR amplicons implies producing from overlapping PCR fragments with distinct differences in GC-versus AT-rich regions. The human and canine poll promoters are approximately 75% GC-rich whereas the HA segment is approximately 60% AT-rich (data not shown). Overlapping PCR amplicons were produced for the HA and NA segments from different subtypes, including H1N1pdm, H5N1, or H9N2 (not shown) and from the 6 internal gene segments of the PR8 strain by designing overlapping primers and optimizing the PCR conditions. The amount obtained in each reaction for full length Flu PCR amplicons was in the order of 1-5 g, which is sufficient for transfection and virus rescue and comparable to the amount of plasmid DNA used for transfection in the conventional plasmid-based RG system (FIG. 13). For the H5N1 vaccine candidates, the polybasic cleavage site (RERRRKKR; SEQ ID NO:50) in highly pathogenic strains was easily removed and replaced by a low pathogenic sequence (TETR) by virtue of adequate set of primers and overlapping PCR (Table 2, FIG. 11).

It was important to determine whether run off poll transcription or the presence of an appropriate t1 signal would make a difference in virus rescue efficiency. The presence of the t1 signal at the 3' end of the Flu PCR amplicon greatly improved virus rescue efficiency, approximately 100-200 fold (FIG. 13 and FIG. 15). This observation was consistent throughout the studies since omitting the t1 signal resulted in less efficient amplification of the Flu GFP replicon and significantly less virus rescue in both human and canine cells.

With respect to the constant vaccine reformulation due to the inherent nature of influenza viruses with perpetual antigenic drift, this approach obviates a crucial step which is the cloning of the HA and NA genes of the vaccine candidate. By providing the appropriate promoter signals, the HA and NA PCR amplicons can be used instead of plasmids, either in a 1+7 or 2+6 combination (FIG. 13). The HA and NA PCR amplicons were shown to produce virus efficiently in the background of not only the laboratory adapted strain PR8 but also in other strains like the AA60ca live attenuated vaccine strain or the WF10 and H1N1pdm wild type strains (FIG. 13). Furthermore, it was shown that the approach is not limited to production of virus from transfected 293T or co-cultured 293T/MDCK cells, which are not approved for vaccine seed preparation. Transfection of Vero cells in a 1+7 and 2+6 mode also resulted in virus rescue (FIG. 14). The ΔH5N1 1+7 virus was rescued in MDCK cells, with the attenuated HA PCR amplicons carrying the k9pol1 and k9t1 signals (FIG. 15).

The boundaries of the system were extended by showing that a complete set of 8 Flu PCR amplicons can be effectively recovered by RG in the context of 4 expression plasmids encoding the influenza polymerase complex (FIG. 13). More importantly, an expression competent PCR version of the 3P and NP was also effective in rescuing the virus in a transfection reaction that contained no plasmids (FIG. 13).

Although it can be argued that rescue efficiency was lower than using a plasmid-based approach, further optimization of the PCR-based system can be achieved by manipulating the amount and proportion of each amplicon in the transfection. Such analysis is beyond the scope of the present report. It could also be argued that the PCR-based system can produce a more variable virus population than the one that is obtained using the plasmid-based system. However, it is an inherent nature of influenza viruses to evolve through point mutations and therefore no reverse genetics system is error free. However, the sequencing of reassortants produced in this study does not show mutations that would alter the antigenicity of the HA surface proteins. In this regard, for vaccine development, as long as the vaccine seed stock is antigenically identical to the vaccine candidate, other mutations would be irrelevant. In fact, influenza vaccines prepared by classical reassortment have only two pre-requisites: 1) HA surface gene derived from the vaccine candidate and 2) high growth in eggs. Full genome sequencing of vaccine viruses is not a pre-requisite for approval of the vaccine by the FDA.

Overall, the implications of this approach for RG development are highly significant. Using a combination of PCR amplicons and plasmids, it would be possible to streamline the study of gene variants for one or more gene segments and determine fitness, pathogenesis or any other biological aspect of the virus. Several mutant viruses with mutations in one or more genes could be produced without having to prepare individual clones. The fact that viruses could be recovered entirely from PCR products implies that other viral systems could be amenable to a similar strategy. This could be particularly important for viruses with genomes larger than the influenza virus that are occasionally associated with cloning difficulties or plasmid instability. In summary, a RG system for influenza was developed that does not require a cloning step for recovery of viruses and has profound implications for vaccine development, pandemic preparedness, and for the study of influenza viruses.

REFERENCES

Banner, D., and A. A. Kelvin. 2012. The current state of H5N1 vaccines and the use of the ferret model for influenza therapeutic and prophylactic development. J Infect Dev Ctries 6:465-469.
2. Basler, C. F., and P. V. Aguilar. 2008. Progress in identifying virulence determinants of the 1918 H1N1 and the Southeast Asian H5N1 influenza A viruses. Antiviral Res 79:166-178.
3. Belshe, R. B., K. M. Edwards, T. Vesikari, S. V. Black, R. E. Walker, M. Hultquist, G. Kemble, E. M. Connor, and C.-T. C. E. S. Group. 2007. Live attenuated versus inactivated influenza vaccine in infants and young children. N Engl J Med 356:685-696.
4. Belshe, R. B., P. M. Mendelman, J. Treanor, J. King, W. C. Gruber, P. Piedra, D. I. Bernstein, F. G. Hayden, K. Kotloff, K. Zangwill, D. Iacuzio, and M. Wolff. 1998. The efficacy of live attenuated, cold-adapted, trivalent, intranasal influenza virus vaccine in children. N Engl J Med 338:1405-1412.
5. de Felipe, P. 2004. Skipping the co-expression problem: the new 2A "CHYSEL" technology. Genet Vaccines Ther 2:13.
6. Draper, S. J., and J. L. Heeney. 2010. Viruses as vaccine vectors for infectious diseases and cancer. Nature reviews. Microbiology 8:62-73.
7. El Sahly, H. M., and W. A. Keitel. 2008. Pandemic H5N1 influenza vaccine development: an update. Expert Rev Vaccines 7:241-247.
8. Fouchier, R. A., V. Munster, A. Wallensten, T. M. Bestebroer, S. Herfst, D. Smith, G. F. Rimmelzwaan, B. Olsen, and A. D. Osterhaus. 2005. Characterization of a novel influenza A virus hemagglutinin subtype (H16) obtained from black-headed gulls. J Virol 79:2814-2822.
9. Fujii, K., Y. Fujii, T. Noda, Y. Muramoto, T. Watanabe, A. Takada, H. Goto, T. Horimoto, and Y. Kawaoka. 2005. Importance of both the coding and the segment specific noncoding regions of the influenza A virus NS segment for its efficient incorporation into virions. J Virol 79:3766-3774.
10. Gao, Q., A. C. Lowen, T. T. Wang, and P. Palese. 2010. A nine-segment influenza a virus carrying subtype H1 and H3 hemagglutinins. J Virol 84:8062-8071.
11. Gao, Q., and P. Palese. 2009. Rewiring the RNAs of influenza virus to prevent reassortment. Proc Natl Acad Sci USA 106:15891-15896. Garulli, B., Y. Kawaoka, and M. R. Castrucci. 2004. Mucosal and systemic immune responses to a human immunodeficiency virus type 1 epitope induced upon vaginal infection with a recombinant influenza A virus. J Virol 78:1020-1025.
13. Golde, W. T., P. Gollobin, and L. L. Rodriguez. 2005. A rapid, simple, and humane method for submandibular bleeding of mice using a lancet. Lab Anim (NY) 34:39-43.
14. Hickman, D., M. J. Hossain, H. Song, Y. Araya, A. Solorzano, and D. R. Perez. 2008. An avian live attenuated master backbone for potential use in epidemic and pandemic influenza vaccines. J Gen Virol 89:2682-2690.
15. Hoffmann, E., G. Neumann, Y. Kawaoka, G. Hobom, and R. G. Webster. 2000. A DNA transfection system for generation of influenza A virus from eight plasmids. Proc Natl Acad Sci USA 97:6108-6113.
16. Jin, H., B. Lu, H. Zhou, C. Ma, J. Zhao, C. F. Yang, G. Kemble, and H. Greenberg. 2003. Multiple amino acid residues confer temperature sensitivity to human influenza virus vaccine strains (FluMist) derived from cold-adapted A/Ann Arbor/6/60. Virology 306:18-24.
17. Johnson, P. R., Jr., S. Feldman, J. M. Thompson, J. D. Mahoney, and P. F. Wright. 1985. Comparison of long-term systemic and secretory antibody responses in children given live, attenuated, or inactivated influenza A vaccine. J Med Virol 17:325-335.
18. Kimble, J. B., E. Sorrell, H. Shao, P. L. Martin, and D. R. Perez. 2011. Compatibility of H9N2 avian influenza surface genes and 2009 pandemic H1N1 internal genes for transmission in the ferret model. Proc Natl Acad Sci USA 108:12084-12088.
19. Liang, Y., Y. Hong, and T. G. Parslow. 2005. cis-Acting packaging signals in the influenza virus PB1, PB2, and PA genomic RNA segments. J Virol 79:10348-10355.
20. Mahmood, K., R. A. Bright, N. Mytle, D. M. Carter, C. J. Crevar, J. E. Achenbach, P. M. Heaton, T. M. Tumpey, and T. M. Ross. 2008. H5N1 VLP vaccine induced protection in ferrets against lethal challenge with highly pathogenic H5N1 influenza viruses. Vaccine 26:5393-5399.
21. Martínez-Sobrido, L., and A. Garcia-Sastre. 2007. Recombinant influenza virus vectors. Future Virology 2:401-416.
22. Matsuoka, Y., E. W. Lamirande, and K. Subbarao. 2009. The ferret model for influenza. Curr Protoc Microbiol Chapter 15: Unit 15G 12.
23. Neumann, G., M. T. Hughes, and Y. Kawaoka. 2000. Influenza A virus NS2 protein mediates vRNP nuclear export through NES-independent interaction with hCRM1. Embo J 19:6751-6758.
12. Garulli, B., Y. Kawaoka, and M. R. Castrucci. 2004. Mucosal and systemic immune responses to a human immunodeficiency virus type 1 epitope induced upon vaginal infection with a recombinant influenza A virus. J Virol 78:1020-1025.
13. Golde, W. T., P. Gollobin, and L. L. Rodriguez. 2005. A rapid, simple, and humane method for submandibular bleeding of mice using a lancet. Lab Anim (NY) 34:39-43.
14. Hickman, D., M. J. Hossain, H. Song, Y. Araya, A. Solorzano, and D. R. Perez. 2008. An avian live attenuated master backbone for potential use in epidemic and pandemic influenza vaccines. J Gen Virol 89:2682-2690.

15. Hoffmann, E., G. Neumann, Y. Kawaoka, G. Hobom, and R. G. Webster. 2000. A DNA transfection system for generation of influenza A virus from eight plasmids. Proc Natl Acad Sci USA 97:6108-6113.
16. Jin, H., B. Lu, H. Zhou, C. Ma, J. Zhao, C. F. Yang, G. Kemble, and H. Greenberg. 2003. Multiple amino acid residues confer temperature sensitivity to human influenza virus vaccine strains (FluMist) derived from cold-adapted A/Ann Arbor/6/60. Virology 306:18-24.
17. Johnson, P. R., Jr., S. Feldman, J. M. Thompson, J. D. Mahoney, and P. F. Wright. 1985. Comparison of long-term systemic and secretory antibody responses in children given live, attenuated, or inactivated influenza A vaccine. J Med Virol 17:325-335.
18. Kimble, J. B., E. Sorrell, H. Shao, P. L. Martin, and D. R. Perez. 2011. Compatibility of H9N2 avian influenza surface genes and 2009 pandemic H1N1 internal genes for transmission in the ferret model. Proc Natl Acad Sci USA 108:12084-12088.
19. Liang, Y., Y. Hong, and T. G. Parslow. 2005. cis-Acting packaging signals in the influenza virus PB1, PB2, and PA genomic RNA segments. J Virol 79:10348-10355.
20. Mahmood, K., R. A. Bright, N. Mytle, D. M. Carter, C. J. Crevar, J. E. Achenbach, P. M. Heaton, T. M. Tumpey, and T. M. Ross. 2008. H5N1 VLP vaccine induced protection in ferrets against lethal challenge with highly pathogenic H5N1 influenza viruses. Vaccine 26:5393-5399.
21. Martínez-Sobrido, L., and A. Garcia-Sastre. 2007. Recombinant influenza virus vectors. Future Virology 2:401-416.
22. Matsuoka, Y., E. W. Lamirande, and K. Subbarao. 2009. The ferret model for influenza. Curr Protoc Microbiol Chapter 15: Unit 15G 12.
23. Neumann, G., M. T. Hughes, and Y. Kawaoka. 2000. Influenza A virus NS2 protein mediates vRNP nuclear export through NES-independent interaction with hCRM1. Embo J 19:6751-6758.
24. Pena, L., A. L. Vincent, J. Ye, J. R. Ciacci-Zanella, M. Angel, A. Lorusso, P. C. Gauger, B. H. Janke, C. L. Loving, and D. R. Perez. 2011. Modifications in the polymerase genes of a swine-like triple-reassortant influenza virus to generate live attenuated vaccines against 2009 pandemic H1N1 viruses. J Virol 85:456-469.
25. Robb, N. C., M. Smith, F. T. Vreede, and E. Fodor. 2009. NS2/NEP protein regulates transcription and replication of the influenza virus RNA genome. J Gen Virol 90:1398-1407.
26. Solorzano, A., J. Ye, and D. R. Perez. 2010. Alternative live-attenuated influenza vaccines based on modifications in the polymerase genes protect against epidemic and pandemic flu. J Virol 84:4587-4596.
27. Song, H., G. R. Nieto, and D. R. Perez. 2007. A new generation of modified live attenuated avian influenza viruses using a two-strategy combination as potential vaccine candidates. J Virol 81:9238-9248.
28. Suguitan, A. L., Jr., J. McAuliffe, K. L. Mills, H. Jin, G. Duke, B. Lu, C. J. Luke, B. Murphy, D. E. Swayne, G. Kemble, and K. Subbarao. 2006. Live, attenuated influenza H5N1 candidate vaccines provide broad cross-protection in mice and ferrets. PLoS A Med 3:e360.
29. Treanor, J. J., J. D. Campbell, K. M. Zangwill, T. Rowe, and M. Wolff. 2006. Safety and immunogenicity of an inactivated subvirion influenza A (H5N1) vaccine. N Engl J Med 354:1343-1351.
30. WHO 2010, posting date. Antigenic and genetic characteristics of influenza A (H5N1) and influenza A (H9N2) viruses and candidate vaccine viruses developed for potential use in human vaccines. [Online.]
31. WHO 2011, posting date. Manual for the laboratory diagnosis and virological surveillance of influenza [Online.]
32. Zhang, J. 2012. Advances and future challenges in recombinant adenoviral vectored H5N1 influenza vaccines. Viruses 4:2711-2735.
33. Zheng, D., Y. Yi, and Z. Chen. 2012. Development of live-attenuated against outbreaks of H5N1 influenza. Viruses 4:3589-3605.
1. Arias, C. F., M. Escalera-Zamudio, L. Soto-Del Rio Mde, A. G. Cobian-Guemes, P. Isa, and S. Lopez. 2009. Molecular anatomy of 2009 influenza virus A (H1N1). Archives of medical research 40:643-654.
2. Chen, W., P. A. Calvo, D. Malide, J. Gibbs, U. Schubert, I. Bacik, S. Basta, R. O'Neill, J. Schickli, P. Palese, P. Henklein, J. R. Bennink, and J. W. Yewdell. 2001. A novel influenza A virus mitochondrial protein that induces cell death. Nat Med 7:1306-1312.
3. Deng, T., F. T. Vreede, and G. G. Brownlee. 2006. Different de novo initiation strategies are used by influenza virus RNA polymerase on its cRNA and viral RNA promoters during viral RNA replication. Journal of virology 80:2337-2348.
4. Feng, L., F. Li, X. Zheng, W. Pan, K. Zhou, Y. Liu, H. He, and L. Chen. 2009. The mouse Pol I terminator is more efficient than the hepatitis delta virus ribozyme in generating influenza-virus-like RNAs with precise 3' ends in a plasmid-only-based virus rescue system. Archives of virology 154:1151-1156.
5. Fodor, E., L. Devenish, O. G. Engelhardt, P. Palese, G. G. Brownlee, and A. Garcia-Sastre. 1999. Rescue of influenza A virus from recombinant DNA. J. Virol. 73:9679-9682.
6. Hoffmann, E., G. Neumann, G. Hobom, R. G. Webster, and Y. Kawaoka. 2000. "Ambisense" approach for the generation of influenza A virus: vRNA and mRNA synthesis from one template. Virology 267:310-317.
7. Hoffmann, E., G. Neumann, Y. Kawaoka, G. Hobom, and R. G. Webster. 2000. A DNA transfection system for generation of influenza A virus from eight plasmids. Proc. Natl. Acad. Sci. US A. 97:6108-6113.
8. Hoffmann, E., J. Stech, Y. Guan, R. G. Webster, and D. R. Perez. 2001. Universal primer set for the full-length amplification of all influenza A viruses. Arch Virol 146: 2275-2289.
9. Hoffmann, E., and R. G. Webster. 2000. Unidirectional RNA polymerase 1-polymerase II transcription system for the generation of influenza A virus from eight plasmids. J Gen Virol 81:2843-2847.
10. Honda, A., and A. Ishihama. 1997. The molecular anatomy of influenza virus RNA polymerase. Biological chemistry 378:483-488.
11. Honda, A., K. Mizumoto, and A. Ishihama. 2002. Minimum molecular architectures for transcription and replication of the influenza virus. Proc Natl Acad Sci USA 99:13166-13171.
12. Huang, Y. W., L. Li, and L. Yu. 2004. [The reverse genetics systems for human and animal RNA viruses]. Sheng wu gong cheng xue bao=Chinese journal of biotechnology 20:311-318.
13. Jin, H., B. Lu, H. Zhou, C. Ma, J. Zhao, C. F. Yang, G. Kemble, and H. Greenberg. 2003. Multiple amino acid residues confer temperature sensitivity to human influenza virus vaccine strains (FluMist) derived from cold-adapted A/Ann Arbor/6/60. Virology 306:18-24.

14. Kawaguchi, A., and K. Nagata. 2007. De novo replication of the influenza virus RNA genome is regulated by DNA replicative helicase, MCM. The EMBO journal 26:4566-4575.
15. Lopez-Turiso, J. A., C. Martinez, T. Tanaka, and J. Ortin. 1990. The synthesis of influenza virus negative-strand RNA takes place in insoluble complexes present in the nuclear matrix fraction. Virus research 16:325-337.
16. Massin, P., P. Rodrigues, M. Marasescu, S. van der Werf, and N. Naffakh. 2005. Cloning of the chicken RNA polymerase I promoter and use for reverse genetics of influenza A viruses in avian cells. Journal of virology 79:13811-13816.
17. Neumann, G., T. Watanabe, H. Ito, S. Watanabe, H. Goto, P. Gao, M. Hughes, D. R. Perez, R. Donis, E. Hoffmann, G. Hobom, and Y. Kawaoka. 1999. Generation of influenza A viruses entirely from cloned cDNAs. Proceedings of the National Academy of Sciences of the United States of America 96:9345-9350.
18. Neumann, G., T. Watanabe, H. Ito, S. Watanabe, H. Goto, P. Gao, M. Hughes, D. R. Perez, R. Donis, E. Hoffmann, G. Hobom, and Y. Kawaoka. 1999. Generation of influenza A viruses entirely from cloned cDNAs. Proceedings of the National Academy of Sciences of the United States of America 96:9345-9350.
19. Neumann, G., T. Watanabe, H. Ito, S. Watanabe, H. Goto, P. Gao, M. Hughes, D. R. Perez, R. Donis, E. Hoffmann, G. Hobom, and Y. Kawaoka. 1999. Generation of influenza A viruses entirely from cloned cDNAs. Proc. Natl. Acad. Sci. USA. 96:9345-9350.
20. Perales, B., and J. Ortin. 1997. The influenza A virus PB2 polymerase subunit is required for the replication of viral RNA. J Virol 71:1381-1385.
21. Perez, D. R., and R. O. Donis. 2001. Functional analysis of PA binding by influenza a virus PB1: effects on polymerase activity and viral infectivity. Journal of virology 75:8127-8136.
22. Perez, D. R., and R. O. Donis. 1998. The matrix 1 protein of influenza A virus inhibits the transcriptase activity of a model influenza reporter genome in vivo. Virology 249:52-61.
23. Perez, D. R., W. Lim, J. P. Seiler, G. Yi, M. Peiris, K. F. Shortridge, and R. G. Webster. 2003. Role of quail in the interspecies transmission of H9 influenza A viruses: molecular changes on HA that correspond to adaptation from ducks to chickens. J Virol 77:3148-3156.
24. Petrovsky, N. Lessons learned from the H1N1 2009 pandemic. Human vaccines 6:780-783.
25. Reed, L. J., and H. Muench. 1938. A simple method for estimating fifty percent endpoints. Am. J. Hyg. 27:493-497.
26. Robertson, J. S., C. Nicolson, R. Harvey, R. Johnson, D. Major, K. Guilfoyle, S. Roseby, R. Newman, R. Collin, C. Wallis, O. G. Engelhardt, J. M. Wood, J. Le, R. Manojkumar, B. A. Pokorny, J. Silverman, R. Devis, D. Bucher, E. Verity, C. Agius, S. Camuglia, C. Ong, S. Rockman, A. Curtis, P. Schoofs, O. Zoueva, H. Xie, X. Li, Z. Lin, Z. Ye, L. M. Chen, E. O'Neill, A. Balish, A. S. Lipatov, Z. Guo, I. Isakova, C. T. Davis, P. Rivailler, K. M. Gustin, J. A. Belser, T. R. Maines, T. M. Tumpey, X. Xu, J. M. Katz, A. Klimov, N. J. Cox, and R. O. Donis. The development of vaccine viruses against pandemic A (H1N1) influenza. Vaccine 29:1836-1843.
27. Shao, H., J. Ye, A. L. Vincent, N. Edworthy, A. Ferrero, A. Qin, and D. R. Perez. 2011. A novel monoclonal antibody effective against lethal challenge with swine-lineage and 2009 pandemic H1N1 influenza viruses in mice. Virology.
28. Suphaphiphat, P., B. Keiner, H. Trusheim, S. Crotta, A. B. Tuccino, P. Zhang, P. R. Dormitzer, P. W. Mason, and M. Franti. Human RNA polymerase 1-driven reverse genetics for influenza a virus in canine cells. Journal of virology 84:3721-3725.
29. Vreede, F. T., and G. G. Brownlee. 2007. Influenza virion-derived viral ribonucleoproteins synthesize both mRNA and cRNA in vitro. Journal of virology 81:2196-2204.
30. Wan, H., E. M. Sorrell, H. Song, M. J. Hossain, G. Ramirez-Nieto, I. Monne, J. Stevens, G. Cattoli, I. Capua, L. M. Chen, R. O. Donis, J. Busch, J. C. Paulson, C. Brockwell, R. Webby, J. Blanco, M. Q. Al-Natour, and D. R. Perez. 2008. Replication and transmission of H9N2 influenza viruses in ferrets: evaluation of pandemic potential. PLoS One 3:e2923.
31. Wang, Z., and G. M. Duke. 2007. Cloning of the canine RNA polymerase I promoter and establishment of reverse genetics for influenza A and B in MDCK cells. Virology journal 4:102.
32. Webby, R. J., R. G. Webster, and J. A. Richt. 2007. Influenza viruses in animal wildlife populations. Current topics in microbiology and immunology 315:67-83.
33. Yamanaka, K., N. Ogasawara, H. Yoshikawa, A. Ishihama, and K. Nagata. 1991. In vivo analysis of the promoter structure of the influenza virus RNA genome using a transfection system with an engineered RNA. Proc Natl Acad Sci USA 88:5369-5373.
34. Ye, J., H. Shao, O. Hickman, M. Angel, K. Xu, Y. Cai, H. Song, R. A. Fouchier, A. Qin, and D. R. Perez. 2010. Intranasal delivery of an IgA monoclonal antibody effective against sublethal H5N1 influenza virus infection in mice. Clin Vaccine Immunol 17:1363-1370.
35. Ye, J., E. M. Sorrell, Y. Cai, H. Shao, K. Xu, L. Pena, D. Hickman, H. Song, M. Angel, R. A. Medina, B. Manicassamy, A. Garcia-Sastre, and D. R. Perez. 2010. Variations in the hemagglutinin of the 2009 H1N1 pandemic virus: potential for strains with altered virulence phenotype? PLoS Pathog 6:e1001145.
36. Zell, R., A. Krumbholz, and P. Wutzler. 2006. Influenza A virus PB1-F2 gene. Emerging infectious diseases 12:1607-1608; author reply 1608-1609.

What is claimed is:

1. A method for producing an influenza virus, comprising: administering to a cell:
   a) a first plasmid comprising a nucleic acid sequence comprising a rearranged influenza type A viral genome segment 2, wherein the rearranged influenza type A viral genome segment 2 comprises:
      i) a first influenza type A viral genome segment, wherein the first influenza type A viral genome segment is influenza type A viral genome segment 2 which comprises a nucleic acid sequence that encodes PB1, and
      ii) a portion of a second influenza type A viral genome segment, wherein the portion of the second influenza type A viral genome segment comprises the portion of influenza type A viral genome segment 8 comprising a nucleic acid sequence that encodes the influenza type A viral protein, NS2, wherein the NS2 nucleic acid sequence is downstream of the nucleic acid sequence that encodes PB1, and
   b) one or more second plasmids comprising remaining viral genes to produce the influenza virus;
   and culturing the cell under conditions for viral replication.

2. The method of claim 1, wherein a cleavage site is present between the nucleic acid sequence that encodes PB1 and the NS2 nucleic acid sequence.

3. The method of claim 2, wherein the cleavage site is a 2A-like-cis-acting hydrolase element (CHYSEL) site.

4. The method of claim 3, wherein the CHYSEL site is a foot-and-mouth disease virus (FMDV) 2A cleavage site.

5. The method of claim 1, wherein the nucleic acid sequence that encodes the PB1 and the NS2 nucleic acid sequence are co-translatable.

6. The method of claim 1, wherein the remaining viral genes required to produce the influenza virus are hemagglutinin, neuraminidase, matrix, nucleocapsid, PB2, PA, and NS1.

7. The method of claim 6, wherein one of the one or more second plasmids comprise a second rearranged influenza type A viral genome segment comprising a portion of influenza type A viral genome segment 8 comprising at least a portion of a nucleic acid sequence that encodes NS1 and is operably linked to an exogenous sequence-wherein the NS2 nucleic acid sequence is removed from the segment 8.

8. The method of claim 7, wherein the exogenous sequence is a therapeutic or reporter gene.

9. The method of claim 1, further comprising harvesting the influenza virus from the cell culture.

10. The method of claim 1, wherein at least a portion of the influenza virus is from influenza A virus subtype H1N1, H5N1, or H9N2.

* * * * *